(12) United States Patent
Kodama

(10) Patent No.: US 7,510,822 B2
(45) Date of Patent: *Mar. 31, 2009

(54) STIMULATION SENSITIVE COMPOSITION AND COMPOUND

(75) Inventor: Kunihiko Kodama, Shizuoka (JP)

(73) Assignee: FUJIFILM Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/409,100

(22) Filed: Apr. 9, 2003

(65) Prior Publication Data

US 2003/0224288 A1 Dec. 4, 2003

(30) Foreign Application Priority Data

Apr. 10, 2002 (JP) ............... P.2002-108104
Aug. 21, 2002 (JP) ............... P.2002-240661

(51) Int. Cl.
G03C 1/73 (2006.01)
G03F 7/039 (2006.01)
G03F 7/038 (2006.01)
C07C 381/12 (2006.01)

(52) U.S. Cl. .............. 430/921; 430/920; 430/922; 430/923; 430/270.1; 430/326; 430/325; 430/905; 430/907; 568/42

(58) Field of Classification Search ............. 430/270.1; 549/29, 14
See application file for complete search history.

(56) References Cited

U.S. PATENT DOCUMENTS

| | | | | |
|---|---|---|---|---|
| 4,103,023 A * | 7/1978 | Aldridge et al. | ............ | 514/470 |
| 5,965,319 A | 10/1999 | Kobayashi | | |
| 6,004,721 A | 12/1999 | Tan et al. | | |
| 6,031,014 A * | 2/2000 | Crivello | .............. | 522/31 |
| 6,280,897 B1 * | 8/2001 | Asakawa et al. | ......... | 430/270.1 |
| 6,326,131 B1 * | 12/2001 | Schell et al. | ............... | 430/505 |
| 6,528,232 B1 * | 3/2003 | Maeda et al. | ........... | 430/270.1 |
| 6,692,884 B2 * | 2/2004 | Fujimori et al. | ............ | 430/170 |
| 6,733,951 B2 * | 5/2004 | Kodama | .............. | 430/270.1 |
| 6,808,862 B2 * | 10/2004 | Kodama | .............. | 430/270.1 |
| 6,852,468 B2 * | 2/2005 | Sato | ................. | 430/270.1 |
| 6,858,370 B2 * | 2/2005 | Kodama et al. | ......... | 430/270.1 |
| 6,900,250 B2 * | 5/2005 | Uesugi et al. | ............... | 522/31 |
| 6,927,009 B2 * | 8/2005 | Kodama et al. | ......... | 430/270.1 |
| 7,122,589 B2 * | 10/2006 | Nishiyama et al. | ......... | 524/155 |
| 2001/0008739 A1 | 7/2001 | Nishiyama et al. | | |
| 2003/0075708 A1 * | 4/2003 | Kodama | ................. | 252/582 |
| 2003/0077540 A1 * | 4/2003 | Kodama et al. | ......... | 430/270.1 |
| 2003/0165776 A1 * | 9/2003 | Yasunami et al. | ........ | 430/280.1 |
| 2003/0170562 A1 * | 9/2003 | Uenishi et al. | ............ | 430/270.1 |
| 2003/0194650 A1 * | 10/2003 | Kanna et al. | ............. | 430/285.1 |
| 2003/0224285 A1 * | 12/2003 | Nakao et al. | ............. | 430/270.1 |
| 2004/0063827 A1 * | 4/2004 | Nishiyama et al. | ......... | 524/155 |

FOREIGN PATENT DOCUMENTS

| | | |
|---|---|---|
| DE | 100 54 550 A1 | 5/2001 |
| EP | 1 260 864 A1 | 11/2002 |
| JP | 2000-292917 A | 10/2000 |
| JP | 2001-294570 A | 10/2001 |
| TW | 565748 | 12/2003 |

OTHER PUBLICATIONS

Chem. Abstract 1984:120601—Dossena et al (Journal of the Chemical Society, Chemical Communications (1983), (21), p. 1196-7.*
Chem. Abstract 1969:523826—Schmidt et al (Tetrahedron Letters (1969), (39), p. 3445-8.*
Crivello et al ("Structural and Mechanistic Studies on the Photolysis of Dialkylphenacylsulfonium Salt Cationic Photoinitiators", Macromolecules, 1983 vol. 16, p. 864-870).*
XP-001161271, James V. Crivello et al, "Structural and Mechanistic Studies on the Photolysis of Dialkylphenacylsulfonium Salt Cationic Photoinitiators", vol. 16, No. 6 (1983) pp. 864-870.
XP-002249096—Abstract (2000).
Partial European Search Report dated Aug. 6, 2003.
Supplemental European Search Report dated Sep. 30, 2003.
Taiwanese Office Action dated Sep. 19, 2008.

* cited by examiner

Primary Examiner—Sin J. Lee
(74) Attorney, Agent, or Firm—Sughrue Mion, PLLC

(57) ABSTRACT

A stimulation sensitive composition comprising:
(A) a compound represented by the specific formula which is capable of generating an acid or a radical by stimulation from the external.

21 Claims, No Drawings

STIMULATION SENSITIVE COMPOSITION AND COMPOUND

FIELD OF THE INVENTION

The present invention relates to a stimulation sensitive composition and the like which is used for a semiconductor production process such as IC, a liquid crystal, the production of a circuit substrate such as a thermal head, further, other photo application system, lithographic printing, an acid curing composition, a radical curing composition and the like.

BACKGROUND OF THE INVENTION

A stimulation sensitive composition is a composition which generates an acid or a radical by stimulation from the external and changes the physical property of a site to which stimulation was provided by reaction thereby, and more preferably a pattern forming material which changes solubility for a irradiated portion of actinic ray and a non irradiated portion and forms a pattern on a substrate.

As one of the stimulation sensitive composition, there is mentioned a chemical amplification resist composition containing an oxygen generating agent which generates an acid by irradiation of actinic ray.

In Japanese Patent Application Laid-Open No. 2000-292917 (hereinafter, referred to as JP-A-2000-292917), there is described a photosensitive composition using a mixture of a triarylsulfonium salt-base acid generating agent and a phenacylsulfonium salt-base acid generating agent.

Further, in JP-A-2001-294570, there is described a photosensitive composition containing a phenacylsulfonium salt-base.

However, it has been desired for a conventional photosensitive composition that the suppression of particles which are generated in the composition during preservation, and sensitivity, the profile of a line and pitch dependency are improved.

SUMMARY OF THE INVENTION

Accordingly, it is the purpose of the present invention to provide a composition excellent in the storage stability and the sensitivity, in particular, to provide a stimulation sensitive composition in which particles which are generated during preservation are suppressed, and the sensitivity, the profile of a line and pitch dependency were improved, and a compound suitable for a stimulation sensitive composition and the like.

The present invention is a constitution described below, and the above-mentioned purposes of the present invention are attained thereby.

(1) A stimulation sensitive composition comprising:

(A) a compound represented by formula (I) which is capable of generating an acid or a radical by stimulation from the external:

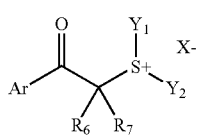

(I)

wherein Ar represents an aryl group or an aromatic group containing a hetero atom, $R_6$ represents a hydrogen atom, a cyano group, an alkyl group or an aryl group, $R_7$ represents a monovalent organic group $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of and $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of formula (I), $X^-$ represents a non-nucleophilic anion.

(2) A photosensitive or heat sensitive composition comprising:

(A) a compound represented by formula (I) which is capable of generating an acid by irradiation of actinic ray or heat:

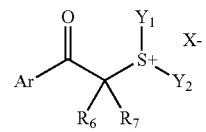

(I)

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of formula (I), $X^-$ represents a non-nucleophilic anion.

(3) A compound represented by formula (I):

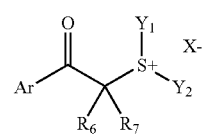

(I)

wherein Ar represents an aryl group or an aromatic group containing a hetero atom, $R_6$ represents a hydrogen atom, a cyano group, an alkyl group or an aryl group, $R_7$ represents a monovalent organic group $Y_1$ and $Y_2$ maybe the same or different, and represents an alkyl group, an aryl group, an aralkyl group or an aromatic group containing a hetero atom. $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of formula (I), $X^-$ represents a non-nucleophilic anion.

(4) A positive type photosensitive or heat sensitive composition comprising:

(A) a compound represented by formula (I) which is capable of generating an acid by irradiation of actinic ray or by heat, and (B) a resin increasing the solubility in an alkali developing solution by the action of an acid:

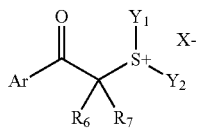

(I)

wherein Ar represents an aryl group or an aromatic group containing a hetero atom, $R_6$ represents a hydrogen atom, a cyano group, an alkyl group or an aryl group, $R_7$ represents a monovalent organic group $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of and $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of formula (I), $X^-$ represents a non-nucleophilic anion.

(5) The positive type photosensitive or heat sensitive composition, according to (4), wherein the resin (B) has a hydroxystyrene structural unit.

(6) The positive type photosensitive or heat sensitive composition, according to (4), wherein the resin (B) has a monocyclic or polycyclic alicyclic hydrocarbon structure.

(7) The positive type photosensitive or heat sensitive composition, according to (6), wherein the resin (B) has further a repeating unit having a lactone structure.

(8) The positive type photosensitive or heat sensitive composition, according to (4), wherein the resin (B) has a fluorine atom.

(9) The positive type photosensitive or heat sensitive composition, according to (4), wherein the resin (B) has a silicon atom.

(10) The positive type photosensitive or heat sensitive composition, according to (4), further comprising (C) a compound having a molecular weight of not more than 3000 which is capable of decomposing by the action of acid to increase solubility in an alkali developing solution.

(11) A positive type photosensitive or heat sensitive composition comprising:

(A) a compound represented by formula (I) which is capable of generating an acid by irradiation of actinic ray or by heat, (D) a resin which is soluble in an alkali developing solution, and (C) a compound having a molecular weight of not more than 3000 which is capable of decomposing by the action of acid to increase solubility in an alkali developing solution:

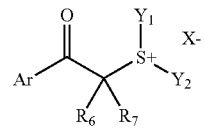

(I)

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of and $Y_1$ and $Y_2$ may be bonded to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of formula (I), $X^-$ represents a non-nucleophilic anion.

(12) A negative type photosensitive or heat sensitive composition comprising:

(A) a compound represented by formula (I) which is capable of generating an acid by irradiation of actinic ray or by heat, (D) a resin which is soluble in an alkali developing solution, and (E) a crosslinking agent which is capable of crosslinking with the alkali-soluble resin by the action of an acid:

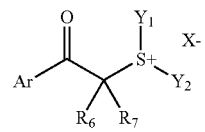

(I)

wherein Ar represents an aryl group or an aromatic group containing a hetero atom, $R_6$ represents a hydrogen atom, a cyano group, an alkyl group or an aryl group, $R_7$ represents a monovalent organic group $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one Ar and $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ is bonded at any one position through a linking group, so that the component (A) may have 2 or more of the structures of the general formula (I), $X^-$ represents a non-nucleophilic anion.

(13) The composition according to (1) and (4), further comprising (F) a basic compound and/or (G) a surfactant containing at least one of a group consisting of a fluorine atom and a silicone atom.

(14) The composition according to (11), wherein the compound (F) is a compound having a structure selected from the group consisting of an imidazole structure, a diazabicyclo structure, an oniumhydroxy structure, an oniumcarboxylate structure, a trialkylamine structure, an aniline structure and a pyridine structure, or an alkylamine derivative having a hydroxy group and/or an ether bond, or an aniline derivative having a hydroxy group and/or an ether bond.

DETAILED DESCRIPTION OF THE INVENTION

As the stimulation sensitive composition and preferably the photosensitive or heat sensitive composition of the present invention, a positive type photosensitive or heat sensitive composition and a negative type photosensitive or heat sensitive composition can be mentioned.

The positive type photosensitive or heat sensitive composition of the present invention, more preferably the positive type resist composition, contains (A) a compound represented by formula (I) (B) a resin increasing the solubility in an alkali developing solution by the action of an acid, and if necessary, contains (C) a compound having a molecular weight of not more than 3000 which is capable of decomposing by the action of acid to increase solubility in an alkali developing solution, alternatively, (A) a compound represented by formula (I), (D) an alkali-soluble resin, and (C) a compound having a molecular weight of not more than 3000 which is capable of decomposing by the action of acid to increase solubility in an alkali developing solution.

The negative type photosensitive or heat sensitive composition of the present invention, more preferably the negative type resist composition, contains (A) a compound represented by formula (I), (D) an alkali-soluble resin, and (E) a crosslinking agent which is capable of crosslinking with the alkali-soluble resin by the action of an acid.

The present invention is specifically illustrated below.

(1) (A) Compound Represented by Formula (I) which is Capable of Generating an Acid or Radical by Stimulation from the External The compound which is capable of generating an acid or radical by stimulation from the external is a compound which is capable of generating an acid or radical by stimulations from the external such as actinic rays such as infrared ray, visible light, ultraviolet rays, far ultraviolet rays, X-rays and electron beam, heat, and ultra sonic.

In formula (I), Ar represents an aryl group or an aromatic group containing a hetero atom. $R_6$ represents a hydrogen atom, a cyano group, an alkyl group or an aryl group. $R_7$ represents a monovalent organic group. $Y_1$ and $Y_2$ may be the same or different, and represents an alkyl group, an aryl group, an aralkyl group or an aromatic group containing a hetero atom. $Y_1$ and $Y_2$ may be bonded to each other to form a ring. Ar and at least one of $Y_1$ and $Y_2$ may be bonded to each other to form a ring. Ar and $R_6$ may be bonded to each other to form a ring. $R_6$ and $R_7$ may be bonded to each other to form a ring. Further, it may have 2 or more of the structures of formula (I) being bonded through a linking group at any one position of Ar, $R_6$, $R_7$, $Y_1$ or $Y_2$. $X^-$ represents a non-nucleophilic anion.

The aryl group of Ar is preferably an aryl group having 6 to 18 carbon atoms, and for example, a phenyl group, a naphthyl group, an anthracenyl group and the like can be mentioned. Among them, a phenyl group and a naphthyl group are preferable, and a phenyl group is more preferable.

The aromatic group containing an hetero atom of Ar is preferably a group having a hetero atom, for example, a nitrogen atom, an oxygen atom, a sulfur atom and the like in the aromatic group such as an aryl group having 6 to 18 carbon atoms.

$R_7$ in the compound represented by formula (I) in the present invention is a monovalent organic group and not a hydrogen atom.

The monovalent organic group of $R_7$ is preferably an alkyl group, an aryl group, a cyano group, alkoxy group, an alkylthio group, an alkoxycarbonyl group and an oxoalkyl group. Among them, an alkyl group and an aryl group are more preferable.

The alkyl group in the alkyl group of $R_6$ and $R_7$ is preferably an alkyl group having 1 to 20 carbon atoms, and for example, there can be mentioned linear chain, branched and cyclic alkyl groups such as a methyl group, an ethyl group, a propyl group, a n-butyl group, a sec-butyl group, a tert-butyl group, a cyclobutyl group, a pentyl group, a neopentyl group, a cyclopentyl group, a hexyl group, a cyclohexyl group, a heptyl group, an octyl group, a nonyl group and a decyl group.

The aryl group of $R_6$ and $R_7$ is preferably an aryl group having 6 to 14 carbon atoms, and for example, a phenyl group, a tolyl group, a naphthyl group and the like can be mentioned.

The alkyl group of $Y_1$ and $Y_2$ is preferably an alkyl group having 1 to 30 carbon atoms, and for example, there can be mentioned linear chain or branched alkyl groups such as a methyl group, an ethyl group, a propyl group, an n-butyl group, a sec-butyl group, a tert-butyl group, n-hexyl group, n-octyl group, n-dodecyl group and cyclic alkyl groups such as a cyclopropyl group, a cyclopentyl group, a cyclohexyl group, an adamantyl group, a norbornyl group, a bornyl group and the like.

The aryl group of $Y_1$ and $Y_2$ is preferably an aryl group having 6 to 14 carbon atoms, and for example, a phenyl group, a tolyl group, a naphthyl group and the like can be mentioned.

The aralkyl group of $Y_1$ and $Y_2$ is preferably an aralkyl group having 7 to 12 carbon atoms, and for example, a benzyl group, a phenethyl group, a cumyl group and the like can be mentioned.

The aromatic group containing a hetero atom of $Y_1$ and $Y_2$ is preferably a group having a hetero atom, for example, a nitrogen atom, an oxygen atom, a sulfur atom and the like in the aromatic group such as an aryl group having 6 to 14 carbon atoms, and for example, heterocyclic aromatic hydrocarbon groups such as furan, thiophene, pyrrole, pyridine and indole can be mentioned.

Ar has 2 or more of substituents and at least 2 of substituents among them may be bonded to each other to form a ring.

In this case, a group which is formed by bonding at least 2 of substituents is preferably a alkylene group having 4 to 10 carbon atoms, and for example, a butylene group, a pentylene group, a hexylene group can and the like be mentioned.

$Y_1$ and $Y_2$ may be bonded to each other to form a ring together with $S^+$ in the general formula (I).

In this case, as the group which is formed by bonding $Y_1$ and $Y_2$, for example, there can be mentioned an alkylene group having 4 to 10 carbon atoms, preferably a butylene group, a pentylene group, a hexylene group, and in particular, preferably a butylene group and a pentylene group. As the group which is formed by bonding $Y_1$ and $Y_2$, a butylenes group is most preferable, and heat stability of the compound is improved by forming a five-membered ring with $S^+$.

Further, a hetero atom may be contained in a ring in which $Y_1$ and $Y_2$ were bonded to form together with $S^+$ in the general formula (I).

Each group of Ar, $R_6$, $R_7$, $Y_1$ and $Y_2$ may not have a substituent, and may have a substituent. As the substituent, for example, there can be mentioned a nitro group, a halogen atom, a carboxyl group, a hydroxyl group, an amino group, a cyano group, an alkoxy group (preferably, having 1 to 5 carbon atoms), an alkyl group (preferably, having 1 to 20 carbon atoms), an aryl group (preferably, having 6 to 14 carbon atoms), an alkyloxycarbonyl group (preferably, having 2 to 7 carbon atoms) and the like.

As the substituent of the alkyl group as $R_6$, $R_7$, $Y_1$ and $Y_2$, a halogen atom is preferable, and a fluorine atom is preferable in particular.

Ar and at least one of $Y_1$ or $Y_2$ may be bonded to each other to form a ring, or Ar and $R_6$ may be bonded to each other to form a ring.

In this case, as the group which is obtained by bonding Ar and at least one of $Y_1$ or $Y_2$ and as the group which is obtained by bonding Ar and $R_6$, an alkylene group having 1 to 10 carbon atoms is preferable, and for example, there can be mentioned a methylene group, an ethylene group, a propylene group, a butylene group, a pentylene group, a hexylene group, and the like. Further, as the group which is obtained by bonding Ar and $R_6$, a carbonyl group is also preferable.

$R_6$ and $R_7$ may be bonded to each other to form a ring. As the group which is obtained by bonding $R_6$ and $R_7$, an alkylene group having 2 to 10 carbon atoms is preferable, and for example, there can be mentioned an ethylene group, a propylene group, a butylene group, a pentylene group, a hexylene group, and the like.

Further, a hetero atom such as an oxygen atom may be contained in a ring in which $R_6$ and $R_7$ were bonded to form.

It may have 2 or more of the structures of the general formula (I) being bonded through a linking group at any one position of Ar, $R_6$, $R_7$, $Y_1$ or $Y_2$.

The component (A) has not a hydrogen atom at $R_7$, therefore photo degradation capability is improved and sensitivity is improved.

The component (A) is preferably that both of $R_6$ and $R_7$ are linear, branched or cyclic alkyl groups having 1 to 20 carbon atoms, or $R_6$ is a hydrogen atom and $R_7$ is a linear, branched or cyclic alkyl group having 2 to 20 carbon atoms.

When both of $R_6$ and $R_7$ are linear, branched or cyclic alkyl groups having 1 to 20 carbon atoms, it is more_preferable that both of $R_6$ and $R_7$ are linear, branched or cyclic alkyl groups having 1 to 8 carbon atoms. $R_6$ and $R_7$ may be same or different, they are preferably the same. Most preferably, both $R_6$ and $R_7$ are methyl groups, ethyl groups or propyl groups.

When $R_6$ is a hydrogen atom and $R_7$ is a linear, branched or cyclic alkyl group having 2 to 20 carbon atoms, $R_7$ is preferably a linear, branched or cyclic alkyl groups having 4 to 20 carbon atoms, more preferably a n-butyl group, an isobutyl group, a pentyl group, a neopentyl group, an actyl group and a dodecyl group.

As the non nucleophilic anion of $X^-$, for example, there can be mentioned sulfonic acid anion, carboxylic acid anion, sulfonyl imide anion, bis(alkylsulfonyl)imide anion, tris(alkylsulfonyl)methyl anion and the like.

The non-nucleophilic anion is an anion having remarkably low capability of provoking a nucleophilic reaction, and an anion which can suppress an elapsing decomposition by an intramolecular nucleophilic reaction. The elapsing stability can be improved thereby.

As the sulfonic acid anion, for example, there are mentioned alkylsulfonic acid anion, arylsulfonic acid anion, camphorsulfonic acid anion, and the like.

As carboxylic acid anion, there are mentioned alkylcarboxylic acid anion, arylcarboxylic acid anion, aralkylcarboxylic acid anion and the like.

As the alkyl group in alkylsulfonic acid anion, there can be mentioned the alkyl group having 1 to 30 carbons, for example, a methyl group, an ethyl group, a propyl group, an isopropyl group, a n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a cyclopropyl group, a cyclopentyl group, a cyclohexyl group, an adamantyl group, a norbonyl group, a bornyl group and the like.

As the aryl group in arylsulfonic acid anion, there can be preferably mentioned aryl groups having 6 to 14 carbon atoms, for example, a phenyl group, a tolyl group, a naphthyl group and the like.

The alkyl group and aryl group in the above-mentioned alkylsulfonic acid anion and arylsulfonic acid anion may have a substituent.

As the substituent, a halogen atom, an alkyl group, an alkoxy group, an alkylthio group and the like can be mentioned.

As the halogen atom, for example, there can be mentioned a fluorine atom, a chlorine atom, a bromine atom, an iodine atom and the like.

As the alkyl group, there can be mentioned the alkyl group having 1 to 15 carbon atoms, for example, a methyl group, an ethyl group, a propyl group, an isopropyl group, a n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group and the like.

As the alkoxy group, there can be mentioned the alkoxy group having 1 to 5 carbon atoms, for example, a methoxy group, an ethoxy group, a propoxy group, a butoxy group and the like.

As the alkylthio group, there can be mentioned the alkylthio group having 1 to 15 carbon atoms, for example, a methylthio group, an ethylthio group, a propylthio group, an isopropylthio group, a n-butylthio group, an isobutylthio group, a sec-butylthio group, a pentylthio group, a neopentylthio group, a hexylthio group, a heptylthio group, an octylthio group, a nonylthio group, a decylthio group, an undecylthio group, a dodecylthio group, a tridecylthio group, a tetradecylthio group, a pentadecylthio group, a hexadecylthio group, a heptadecylthio group, an octadecylthio group, a nonadecylthio group, an icosylthio group and the like. Further, the alkyl group, alkoxy group and alkylthio group may be substituted with a halogen atom (preferably, a fluorine atom).

As the alkyl group in alkylcarboxylic acid anion, there can be mentioned those which are similar as the alkyl group in alkylsulfonic acid anion.

As the aryl group in arylcarboxylic acid anion, there can be mentioned those which are similar as the aryl group in arylsulfonic acid anion.

As the aralkyl group in aralkylcarboxylic acid anion, there can be preferably mentioned aralkyl groups having 6 to 12 carbon atoms, for example, a benzyl group, a phenethyl group, a naphthylmethyl group, a naphthylethyl group, a naphthylmethyl group and the like.

The alkyl group, aryl group and aralkyl group in the above-mentioned alkylcarboxylic acid anion, arylcarboxylic acid anion and aralkylcarboxylic acid anion may have a substituent, and as the substituent, for example, there can be mentioned a halogen atom, an alkyl group, an alkoxy group, an alkylthio group and the like in like manner as in the arylsulfonic acid anion.

As the sulfonylimide anion, for example, saccharine anion can be mentioned.

The alkyl group in bis(alkylsulfonyl)imide anion and tris(alkylsulfonyl)methyl anion includes a linear and branched alkyl group, and the examples thereof preferably include the alkyl group having 1 to 5 carbon atoms, for example, a methyl group, an ethyl group, a propyl group, an isopropyl group, a n-butyl group, an isobutyl group, a sec-butyl group, a pentyl group, a neopentyl group and the like. These alkyl groups may have a substituent and as the substituent, there can be mentioned a halogen atom, an alkoxy group, an alkylthio group and the like, and among them, a fluorine atom is preferable.

As other non-nucleophilic anion, for example, phosphorous fluoride, boron fluoride, antimony fluoride and the like can be mentioned.

As the non-nucleophilic anion of $X^-$, there are preferable a sulfonic acid anion obtained by substituting the α position of a sulfonic acid with a fluorine atom, an arylsulfonic acid anion which was substituted with a fluorine atom or a group having a fluorine atom, a bis(alkylsulfonyl)imide anion in which the alkyl group was substituted with a fluorine atom, and a tris (alkylsulfonyl)methyl anion in which the alkyl group was substituted with a fluorine atom. As the non-nucleophilic anion of $X^-$, a perfluoroalkanesulfonic acid anion having 1 to 8 carbon atoms is preferable in particular, and nonafluorobutanesulfonic acid anion and perfluorooctanesulfonic acid anion are most preferable.

The compound represented by formula (I) is preferably a compound represented by formula (Ia).

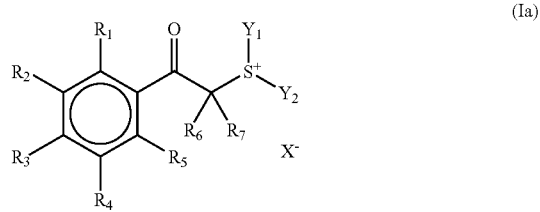

(Ia)

In the general formula (Ia), $R_1$ to $R_5$ may be the same or different, and represents a hydrogen atom, a nitro group, a halogen atom, an alkyl group, an alkoxy group, an alkoxycarbonyl group, an aryl group or an acylamino group. At least 2 of $R_1$ to $R_5$ may be bonded to each other to form a ring.

At least one of $R_1$ to $R_5$ and at least one of $Y_1$ and $Y_2$ may be bonded to each other to form a ring. At least one of $R_1$ to $R_5$ and $R_6$ may be bonded to each other to form a ring. $R_6$ and $R_7$ may be bonded to each other to form a ring. Further, it may have 2 or more of the structures of the general formula (Ia) being bonded through a linking group at any one position of $R_1$ to $R_7$, $Y_1$ or $Y_2$.

$R_6$, $R_7$, $Y_1$, $Y_2$ and $X^-$ in the formula (Ia) have the same meaning as described in the formula (I).

The alkyl group in the alkyl group and acylamino group of $R_1$ to $R_5$ is preferably an alkyl group having 1 to 20 carbon atoms, and for example, there can be mentioned linear chain, branched and cyclic alkyl groups such as a methyl group, an ethyl group, a propyl group, an n-butyl group, a sec-butyl group, a tert-butyl group, a cyclobutyl group, a pentyl group, a neopentyl group, a cyclopentyl group, a hexyl group, a cyclohexyl group, a heptyl group, an octyl group, a nonyl group and a decyl group.

The alkoxy group in an alkoxy group, an alkyloxycarbonyl group of $R_1$ to $R_5$ is preferably an alkoxy group having 1 to 10 carbon atoms, and for example, there can be mentioned a methoxy group, an ethoxy group, a propoxy group, a butoxy group, an isobutoxy group, a sec-butoxy group, a tert-butoxy group, a pentyloxy group, a hexyloxy group, a cyclohexyloxy group, a heptyloxy group, an octyloxy group, a nonyloxy group, a decyloxy group and the like.

The aryl group of $R_1$ to $R_5$ is preferably an aryl group having 6 to 14 carbon atoms, and for example, a phenyl group, a tolyl group, a naphthyl group and the like can be mentioned.

As the halogen atom of $R_1$ to $R_5$, there can be mentioned a fluorine atom, a chlorine atom, a bromine atom, an iodine atom and the like.

At least two of $R_1$ to $R_5$ may be bonded to each other to form a ring structure.

In this case, the group which is formed by bonding at least 2 among $R_1$ to $R_5$ is preferably a alkylene group having 4 to 10 carbon atoms, and for example, a butylene group, a pentylene group, a hexylene group and the like can be mentioned.

Each group of $R_1$ to $R_5$ may not have a substituent, and may have a substituent. As the substituent for example, there can be mentioned a nitro group, a halogen atom, a carboxyl group, a hydroxyl group, an amino group, a cyano group, an alkoxy group (preferably, having 1 to 5 carbon atoms), an alkyl group (preferably, having 1 to 20 carbon atoms), an aryl group (preferably, having 6 to 14 carbon atoms), an alkyloxycarbonyl group (preferably, having 2 to 7 carbon atoms) and the like.

As the substituent of the alkyl group as $R_1$ to $R_5$, a halogen atom is preferable, and a fluorine atom is preferable in particular.

At least one of $R_1$ to $R_5$ and at least one of $Y_1$ or $Y_2$ may be bonded to each other to form a ring and at least one of $R_1$ to $R_5$ and $R_6$ may be bonded to each other to form a ring.

In this case, as the group which is obtained by bonding at least one of $R_1$ to $R_5$ and at least one of $Y_1$ or $Y_2$ and as the group which is obtained by bonding at least one of $R_1$ to $R_5$ and $R_6$, an alkylene group having 1 to 10 carbon atoms is preferable, and for example, there can be mentioned a methylene group, an ethylene group, a propylene group, a butylene group, a pentylene group, a hexylene group, and the like. Further, as the group which is obtained by bonding at least one of $R_1$ to $R_5$ and $R_6$, a carbonyl group is also preferable.

When a ring is formed by bonding $R_5$ and $R_6$, it is preferable that $R_7$ is an alkyl group having 1 to 20 carbon atoms.

In the general formula (Ia), any one of $R_1$ to $R_5$ is preferably an alkyl group, more preferably a linear, branched or cyclic alkyl group having 1 to 12 carbon atoms, further preferably a branched or cyclic alkyl group having 3 to 8 carbon atoms, and most preferably an isopropyl group, a t-butyl group, a cyclopentyl group and a cyclohexyl group.

It may have 2 or more of the structures of the general formula (Ia) being bonded through a linking group at any one position of $R_1$ to $R_5$, $R_6$, $R_7$, $Y_1$ or $Y_2$.

The preferably specific examples of the compound represented by the above-mentioned general formula (I) of the present invention are illustrated below, but the present invention is not limited to these.

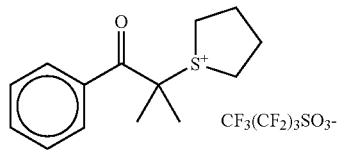 (I-1)
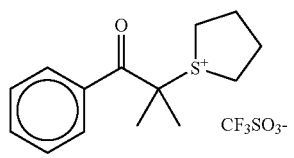 (I-2)
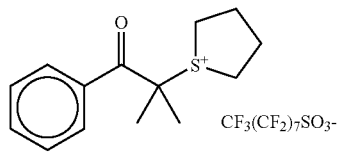 (I-3)
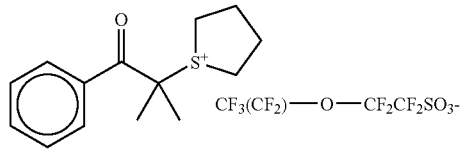 (I-4)
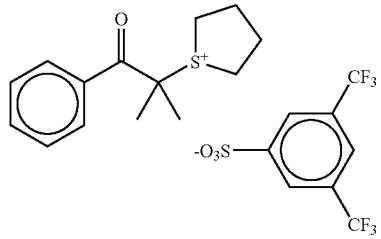 (I-5)
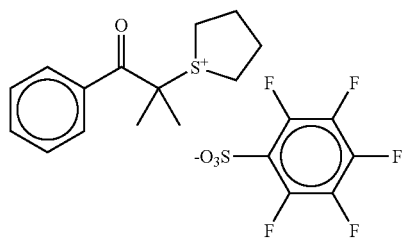 (I-6)
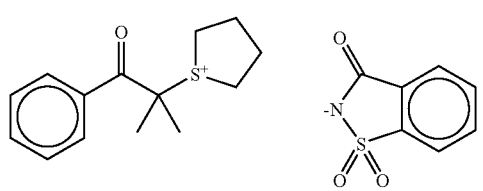 (I-7)
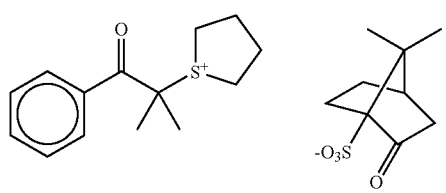 (I-8)
-continued
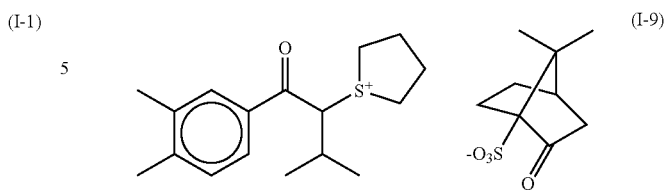 (I-9)
 (I-10)
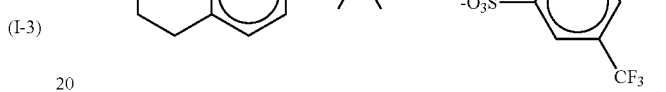 (I-11)
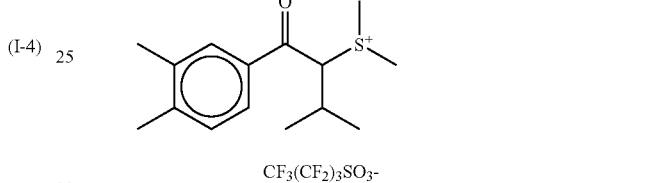 (I-12)
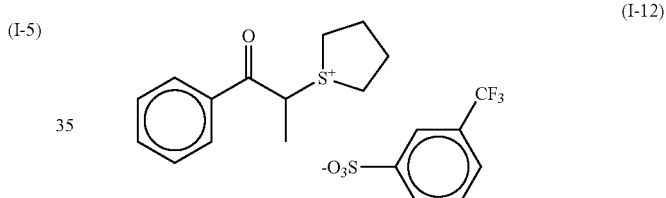 (I-13)
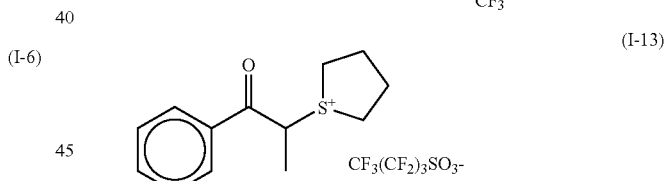 (I-14)
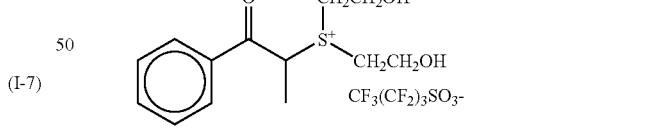 (I-15)
 (I-16)

-continued
(I-17)
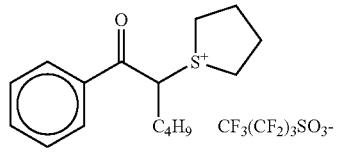
(I-18)
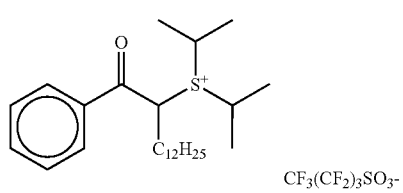
(I-19)
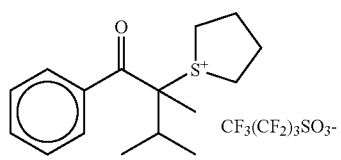
(I-20)
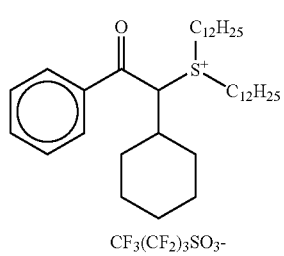
(I-21)
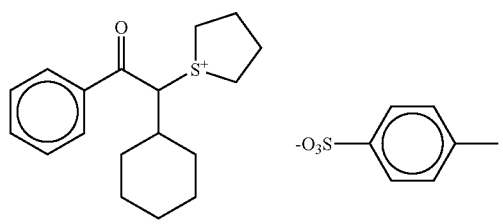
(I-22)
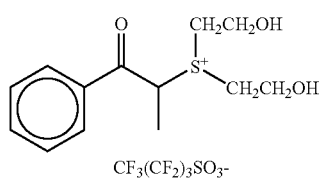
(I-23)
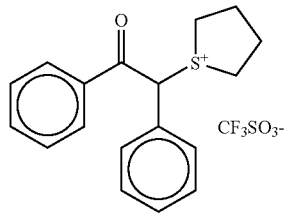
-continued
(I-24)
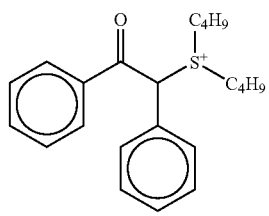
(I-25)
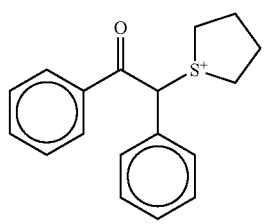
(I-26)
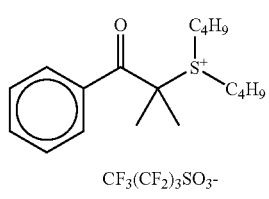
(I-27)
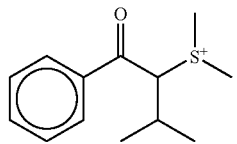
(I-28)
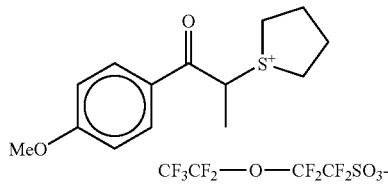
(I-29)
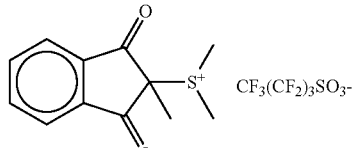
(I-30)
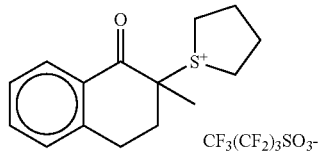

-continued
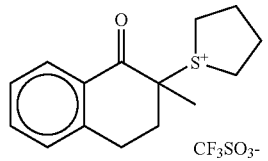
(I-31)
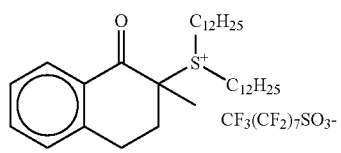
(I-32)
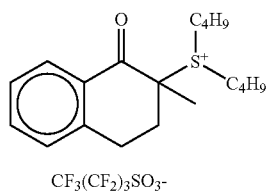
(I-33)
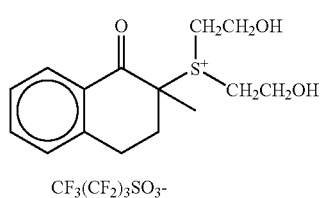
(I-34)
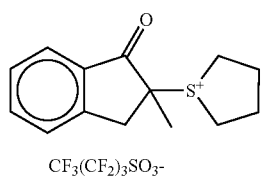
(I-35)
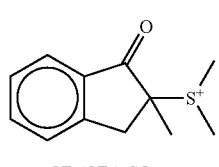
(I-36)
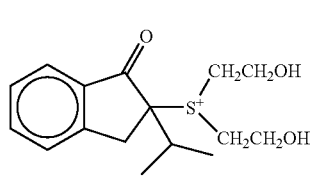
(I-37)
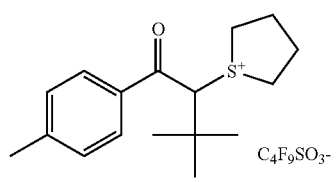
(I-38)
-continued
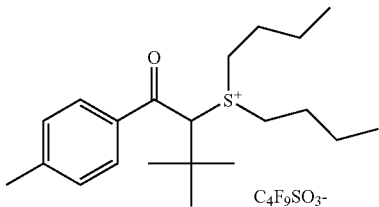
(I-39)
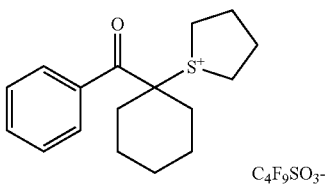
(I-40)
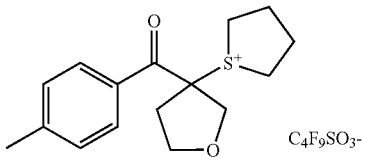
(I-41)
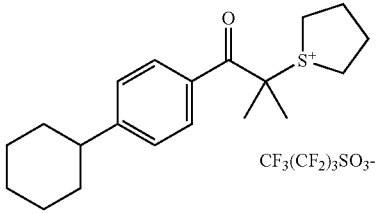
(I-42)
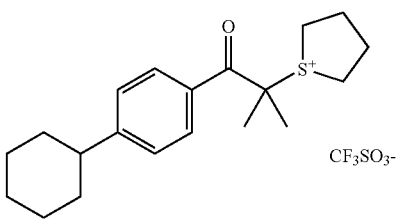
(I-43)
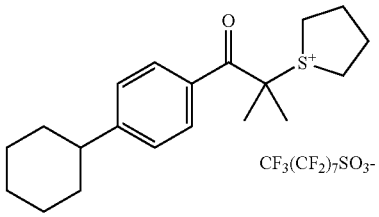
(I-44)
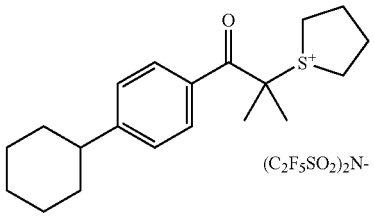
(I-45)

-continued
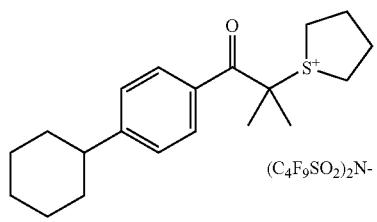
(I-46)
(C4F9SO2)2N-
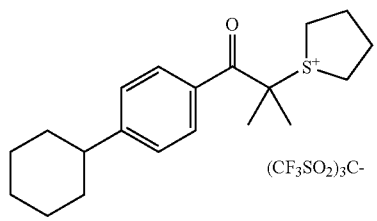
(I-47)
(CF3SO2)3C-
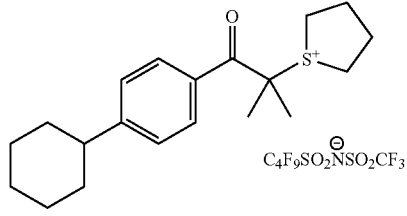
(I-48)
C4F9SO2NSO2CF3
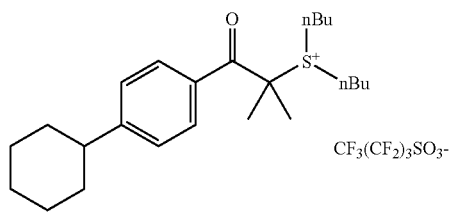
(I-49)
CF3(CF2)3SO3-
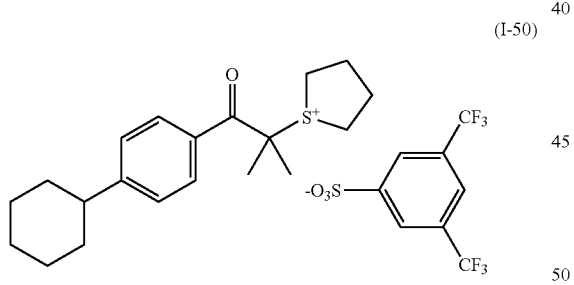
(I-50)
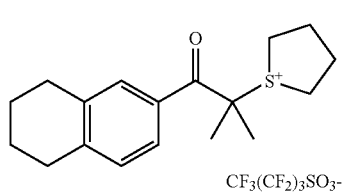
(I-51)
CF3(CF2)3SO3-
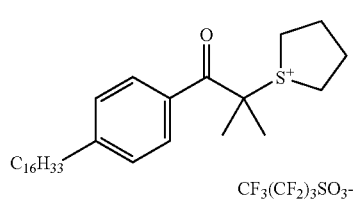
(I-52)
CF3(CF2)3SO3-
-continued
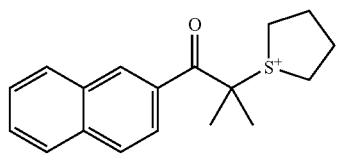
(I-53)
CF3(CF2)3SO3-
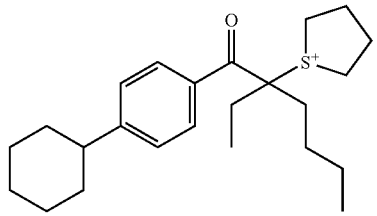
(I-54)
CF3(CF2)3SO3-
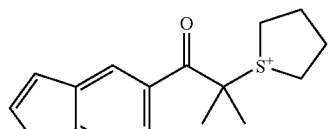
(I-55)
CF3(CF2)3SO3-
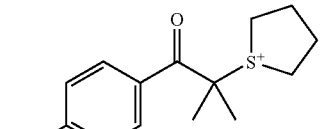
(I-56)
CF3(CF2)3SO3-
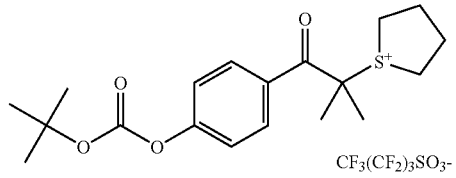
(I-57)
CF3(CF2)3SO3-
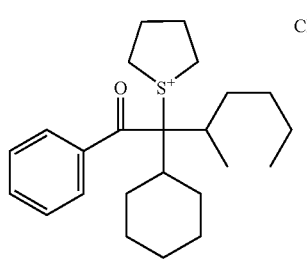
(I-58)
CF3(CF2)3SO3-
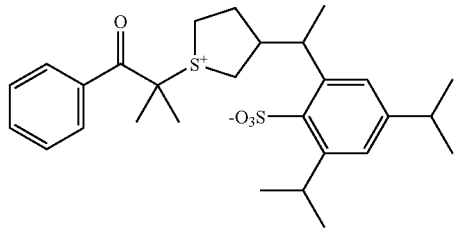
(I-59)

-continued (I-60)
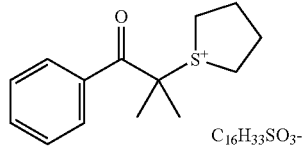
C₁₆H₃₃SO₃⁻

(I-61)
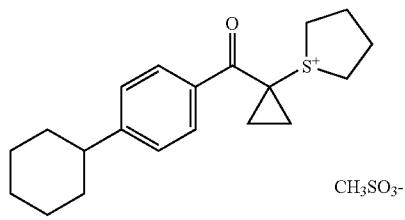
CH₃SO₃⁻

(I-62)
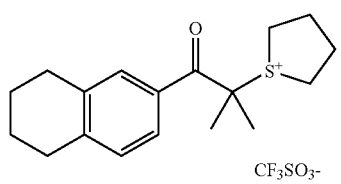
CF₃SO₃⁻

(I-63)
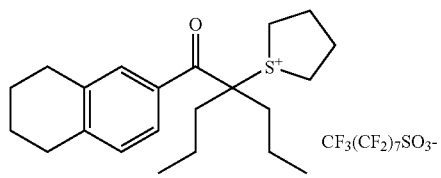
CF₃(CF₂)₇SO₃⁻

(I-64)
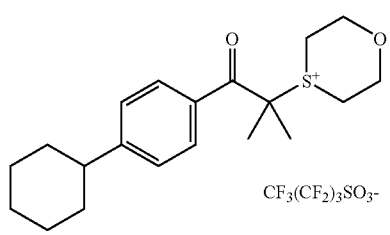
CF₃(CF₂)₃SO₃⁻

(I-65)
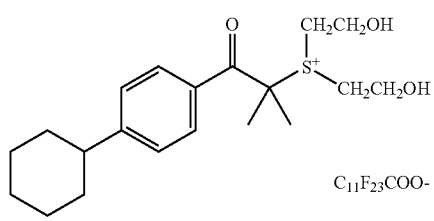
C₁₁F₂₃COO⁻

(I-66)
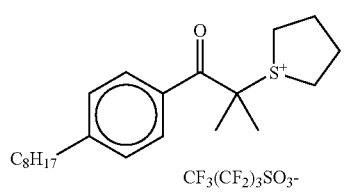
CF₃(CF₂)₃SO₃⁻

(I-67)
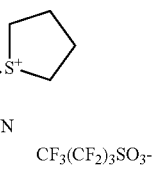
CF₃(CF₂)₃SO₃⁻

-continued (I-68)
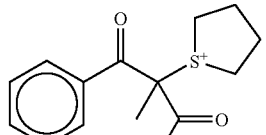
CF₃(CF₂)₃SO₃⁻

(I-69)
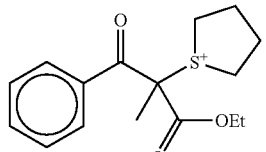
CF₃(CF₂)₃SO₃⁻

(I-70)
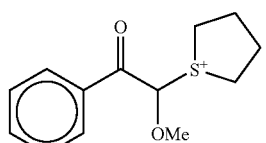
CF₃(CF₂)₇SO₃⁻

The compound of the general formula (I) can be used alone or a combination of 2 or more can be used.

The compound indicated by the general formula (I) can be obtained by reacting a corresponding acylbenzene derivative with trialkylsilyl halogenide under a basic condition to prepare silylenol ether, reacting this with sulfoxide to synthesize a sulfonium skeleton and carrying out the salt exchange of this with a corresponding anion. As an alternative synthesis method, there can be mentioned a method of reacting a corresponding phenacyl halogenide with a sulfide compound in the absence or presence of a silver catalyst to synthesize a sulfonium skeleton and carrying out the salt exchange of this with a corresponding anion.

The content of the compound of the component (A) in the stimulation sensitive composition of the present invention is preferably 0.1 to 20% by weight based on the solid content of the composition, more preferably 0.5 to 10% by weight and further preferably 1 to 7% by weight.

Compound Capable of Generating an Acid which can be Used in Combination other than Component (A)

In the present invention, a compound capable of generating an acid by the irradiation of actinic ray (hereinafter referred to as photo-acid generator) may be further used in combination other than component (A).

The amount of the photo-acid generator capable of being used in combination with the component (A) of the present invention is usually 100/0 to 20/80 by a molar ratio (component (A)/other photo-acid generator), preferably 100/0 to 40/60 and further preferably 100/0 to 50/50.

As the photo-acid generator capable of being used in combination, the optical initiator of optical cation polymerization, the optical initiator of optical radical polymerization, the optical quencher of dyes, an optical alterant, or known compounds which are used for a micro resist and the like and generates an acid by the irradiation of actinic ray, and a mixture thereof are appropriately selected to able to be used.

For example, a diazonium salt, a phosphonium salt, an iodonium salt, imide sulfonate, oxime sulfonate, diazosulfone, disulfone and o-nitrobenzylsulfonate can be mentioned.

Further, there can be used a compound in which a group or a compound generating an acid by the irradiation of actinic ray was introduced, for example, compounds which are described in U.S. Pat. No. 3,849,137, German Patent 3914407, JP-A-63-26653, JP-A-55-164824, JP-A-62-69263, JP-A-63-146038, JP-A-63-163452, JP-A-62-153853, JP-A-63-146029 and the like.

Further, there can be also used compounds generating an acid by the irradiation of beam which are described in U.S. Pat. No. 3,779,778, EP 126712 and the like.

As preferable compounds in particular among the compounds capable of generating an acid by the irradiation of actinic ray which may be used in combination, compounds represented by the under-mentioned general formula (ZI), (ZII) and (ZIII) can be mentioned.

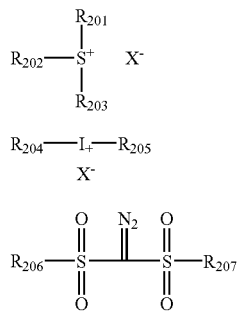

In the above-mentioned general formula (ZI) each of $R_{201}$, $R_{202}$ and $R_{203}$ independently represents an organic group.

$X^-$ represents a non-nucleophilic anion, and there can be mentioned those similar as the non-nucleophilic anion of $X^-$ in the general formula (I).

The carbon number of the organic group as $R_{201}$, $R_{202}$ and $R_{203}$ is usually 1 to 30 and preferably 1 to 20.

Further, 2 of $R_{201}$, $R_{202}$ and $R_{203}$ may be bonded to each other to form a ring structure, and an oxygen atom, a sulfur atom, an ester bond, an amide bond and a carbonyl group may be contained therein.

As the group which is formed by bonding 2 of $R_{201}$, $R_{202}$ and $R_{203}$, an alkylene group (for example, a butylene group, a pentylene group) is mentioned.

As the specific example of the organic group as $R_{201}$, $R_{202}$ and $R_{203}$, a group corresponding in the compounds (ZI-1), (ZI-2) and (ZI-3) which are described later can be mentioned.

Further, they may be a compound having a plural number of structures represented by the general formula (ZI). For example, they may be a compound having a structure in which at least one of $R_{201}$, $R_{202}$ and $R_{203}$ of the compound represented by the general formula (ZI) was bonded with at least one of $R_{201}$, $R_{202}$ and $R_{203}$ of the another compound represented by the general formula (ZI).

As the further preferable component (ZI), there can be mentioned compounds (ZI-1), (ZI-2) and (ZI-3) which are illustrated below.

The compound (ZI-1) is an arylsulfonium compound in which at least one of $R_{201}$, $R_{202}$ and $R_{203}$ of the above-mentioned general formula (ZI) is an aryl group, namely, a compound in which arylsulfonium is cation.

With respect to the arylsulfonium compound, all of $R_{201}$, $R_{202}$ and $R_{203}$ may be aryl groups, and the portion of $R_{201}$, $R_{202}$ and $R_{203}$ is an aryl group and the residue may be an alkyl group.

As the arylsulfonium compound, for example, there can be mentioned a triarylsulfonium compound, a diarylsulfonium compound and an aryldialkylsulfonium compound.

As the aryl group of the arylsulfonium compound, a phenyl group and a naphthyl group are preferable, and a phenyl group is more preferable. When the arylsulfonium compound has 2 or more of aryl groups, 2 or more of aryl groups may be the same or different.

The alkyl group which the arylsulfonium compound may optionally have is preferably a linear chain, branched or cyclic alkyl group having 1 to 15 carbon atoms, and for example, a methyl group, an ethyl group, a propyl group, a n-butyl group, a sec-butyl group, a tert-butyl group, a cyclopropyl group, a cyclobutyl group, a cyclohexyl group, and the like.

The aryl group and alkyl group of $R_{201}$, $R_{202}$ and $R_{203}$ may have an alkyl group (for example, 1 to 15 carbon atoms), an aryl group (for example, 6 to 14 carbon atoms), an alkoxy group (for example, 1 to 15 carbon atoms), a halogen atom, a hydroxy group and a phenylthio group as a substituent. Preferable substituent is a linear chain, branched or cyclic alkyl group having 1 to 12 carbon atoms and a linear chain, branched or cyclic alkoxy group having 1 to 12 carbon atoms, and most referable substituent is an alkyl group having 1 to 4 carbon atoms and an alkoxy group having 1 to 4 carbon atoms. The substituent may be substituted to any one of three of $R_{201}$, $R_{202}$ and $R_{203}$, and may be substituted to all of three. Further, when $R_{201}$, $R_{202}$ and $R_{203}$ are aryl groups, it is preferable that the substituent is substituted to the p-position of the aryl group.

Then, the compound (ZI-2) is illustrated.

The compound (ZI-2) is a compound when each of $R_{201}$, $R_{202}$ and $R_{203}$ in the formula (ZI) independently represents an organic group not containing an aromatic ring. Hereat, the aromatic ring includes an aromatic ring containing a hetero atom.

The organic group not containing an aromatic ring as $R_{201}$, $R_{202}$ and $R_{203}$ is generally 1 to 30 carbon atoms and preferably 1 to 20 carbon atoms.

Each of $R_{201}$ to $R_{203}$ in the formula (ZI) independently is preferably an alkyl group, a 2-oxoalkyl group, an alkoxycarbonylmethyl group, an allyl group and a vinyl group, more preferably a linear chain, branched or cyclic 2-oxoalkyl group, alkoxycarbonylmethyl group, and most preferably a linear chain, branched 2-oxoalkyl group.

The alkyl group as $R_{201}$ to $R_{203}$ may be any one of a linear chain, a branched or a cyclic group, and there can be mentioned preferably a linear chain or branched alkyl group having 1 to 10 carbon atoms (for example, a methyl group, an ethyl group, a propyl group, a butyl group and a pentyl group), and a cyclic alkyl group having 3 to 10 carbon atoms (a cyclopentyl group, a cyclohexyl group and a norbornyl group).

The 2-oxoalkyl group as $R_{201}$ to $R_{203}$ may be any one of a linear chain, a branched or a cyclic group, and there can be mentioned preferably a group having >C=O at 2-position of the above-mentioned alkyl group.

As the alkoxy group in the alkoxycarbonylmethyl group as $R_{201}$ to $R_{203}$, there can be mentioned preferably an alkyl group having 1 to 5 carbon atoms (for example, a methyl group, an ethyl group, a propyl group, a butyl group and a pentyl group).

$R_{201}$ to $R_{203}$ may be further substituted with a halogen atom, an alkoxy group (for example, 1 to 5 carbon atoms), a hydroxy group, a cyano group, and a nitro group.

Two of $R_{201}$ to $R_{203}$ may be bonded to form a ring structure, and may contain an oxygen atom, a sulfur atom, an ester bond, an amide bond and a carbonyl group in a ring. As the group which is formed by bonding two of $R_{201}$ to $R_{203}$, an alkylene group (for example, a butylene group and a pentylene group) can be mentioned.

The compound (ZI-3) is a compound represented by the general formula (ZI-3) below, and a compound having a phenacylsulfonium salt structure.

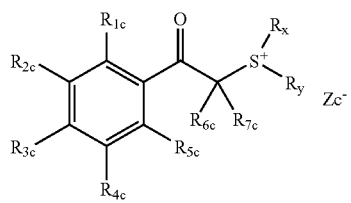

Each of $R_{1c}$ to $R_{5c}$ independently represents a hydrogen atom, an alkyl group, an alkoxy group or a halogen atom.

$R_{6c}$ and $R_{7c}$ represent a hydrogen atom.

Each of Rx and Ry independently represents an alkyl group, a 2-oxoalkyl group, an alkyloxycarbonylmethyl group, an allyl group or a vinyl group.

At least 2 or more of $R_{1c}$ to $R_{5c}$ and Rx and Ry may be respectively bonded to form a ring, and the ring structure may contain an oxygen atom, a sulfur atom, an ester bond and an amide bond.

$Z_c^-$ represents a non-nucleophilic anion, and there can be mentioned those similar as the non-nucleophilic anion of $X^-$ in the general formula (I).

The alkyl group as $R_{1c}$ to $R_{5c}$ may be any one of a linear chain, a branched or a cyclic group, and, for example, there can be mentioned an alkyl group having 1 to 10 carbon atoms, preferably a linear chain or branched alkyl group having 1 to 5 carbon atoms (for example, a methyl group, an ethyl group, a linear chain or branched propyl group, a linear chain or branched butyl group and a linear chain or branched pentyl group), and a cyclic alkyl group having 3 to 8 carbons (for example, a cyclopentyl group and a cyclohexyl group).

As the alkoxy group as $R_{1c}$ to $R_{5c}$ may be any one of a linear chain, a branched or a cyclic group, and, for example, there can be mentioned an alkoxy group having 1 to 10 carbon atoms, preferably a linear chain or branched alkoxy group having 1 to 5 carbon atoms (for example, a methoxy group, an ethoxy group, a linear chain or branched propoxy group, a linear chain or branched butoxy group and a linear chain or branched pentoxy group), and a cyclic alkoxy group having 3 to 8 carbons (for example, a cyclopentyloxy group and a cyclohexyloxy group).

Any one of $R_{1c}$ to $R_{5c}$ is preferably a linear chain, branched or cyclic alkyl group, or a linear chain, branched or cyclic alkoxy group, and the sum of carbon number of $R_{1c}$ to $R_{5c}$ is further preferably 2 to 15. Thus, the solubility to a solvent is improved and the generation of particles at preservation is suppressed.

As the alkyl group as Rx and Ry, those similar as the alkyl group as $R_{1c}$ to $R_{5c}$ can be mentioned.

As the 2-oxoalkyl group, a group having >C=O at 2-position of the alkyl group as $R_{1c}$ to $R_{5c}$ can be mentioned.

As the alkoxy group in the alkoxycarbonylmethyl group, those similar as the alkoxy group as $R_{1c}$ to $R_{5c}$ can be mentioned.

As the group which Rx and Ry are bonded to form, a butylene group, a pentylene group and the like can be mentioned.

In the formula (Z1-3), it is preferable that both Rx and Ry are alkyl groups having 4 to 12 carbon atoms, or alkyl groups having a hydroxy group.

Each of $R_{204}$ to $R_{207}$ in the general formulae (ZII) and (ZIII) independently represents an aryl group which may optionally have a substituent, or an alkyl group which may optionally have a substituent.

The aryl group of $R_{204}$ to $R_{207}$ is preferably a phenyl group and a naphthyl group and more preferably a phenyl group.

The alkyl group as $R_{204}$ to $R_{207}$ may be any one of a linear chain, a branched or a cyclic group, and, for example, there can be mentioned preferably a linear chain or branched alkyl group having 1 to 10 carbons (for example, a methyl group, an ethyl group, a propyl group, a butyl group and a pentyl group), and a cyclic alkyl group having 3 to 10 carbons (a cyclopentyl group, a cyclohexyl group and a norbornyl group).

As the substituent which $R_{204}$ to $R_{207}$ have, for example, there can be mentioned an alkyl group (for example, 1 to 15 carbon atoms), an aryl group (for example, 6 to 15 carbon atoms), an alkoxy group (for example, 1 to 15 carbon atoms), a halogen atom, a hydroxy group, a phenylthio group and the like.

$X^-$ represents a non-nucleophilic anion, and there can be mentioned those similar as the non-nucleophilic anion of $X^-$ in the general formula (I).

As preferable compounds in particular among the compounds capable of generating an acid by the irradiation of actinic ray or radiation which may be used in combination, compounds represented by the under-mentioned general formula (ZIV), (ZV) and (ZVI) can be further mentioned.

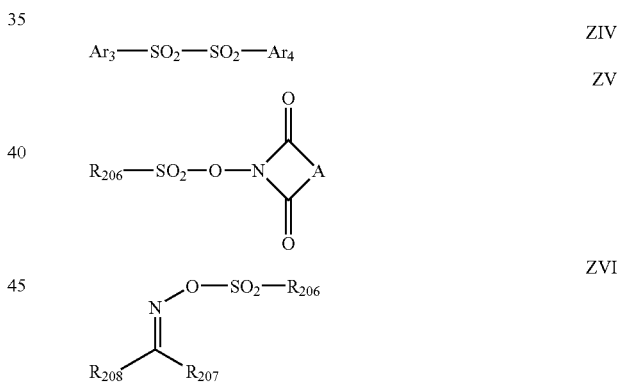

In the formulae (ZIV) to (ZVI), $Ar_3$ and $Ar_4$ independentlly represents a substituted or unsubstituted aryl group.

$R_{206}$, $R_{207}$ and $R_{208}$, which may be same or different, represent substituted or unsubstituted alkyl group, or substituted or unsubstituted aryl group.

A represents substituted or unsubstituted alkylene group, substituted or unsubstituted alkenylene group, or substituted or unsubstituted arylene group.

Among the compounds capable of generating an acid by the irradiation of actinic ray or radiation which may be used in combination, compounds represented by the general formula (ZI) to (ZIII) are more preferable.

Hereinafter, preferable examples in particular are mentioned among compounds capable of generating an acid by irradiation of actinic ray or radiation which may be used in combination.

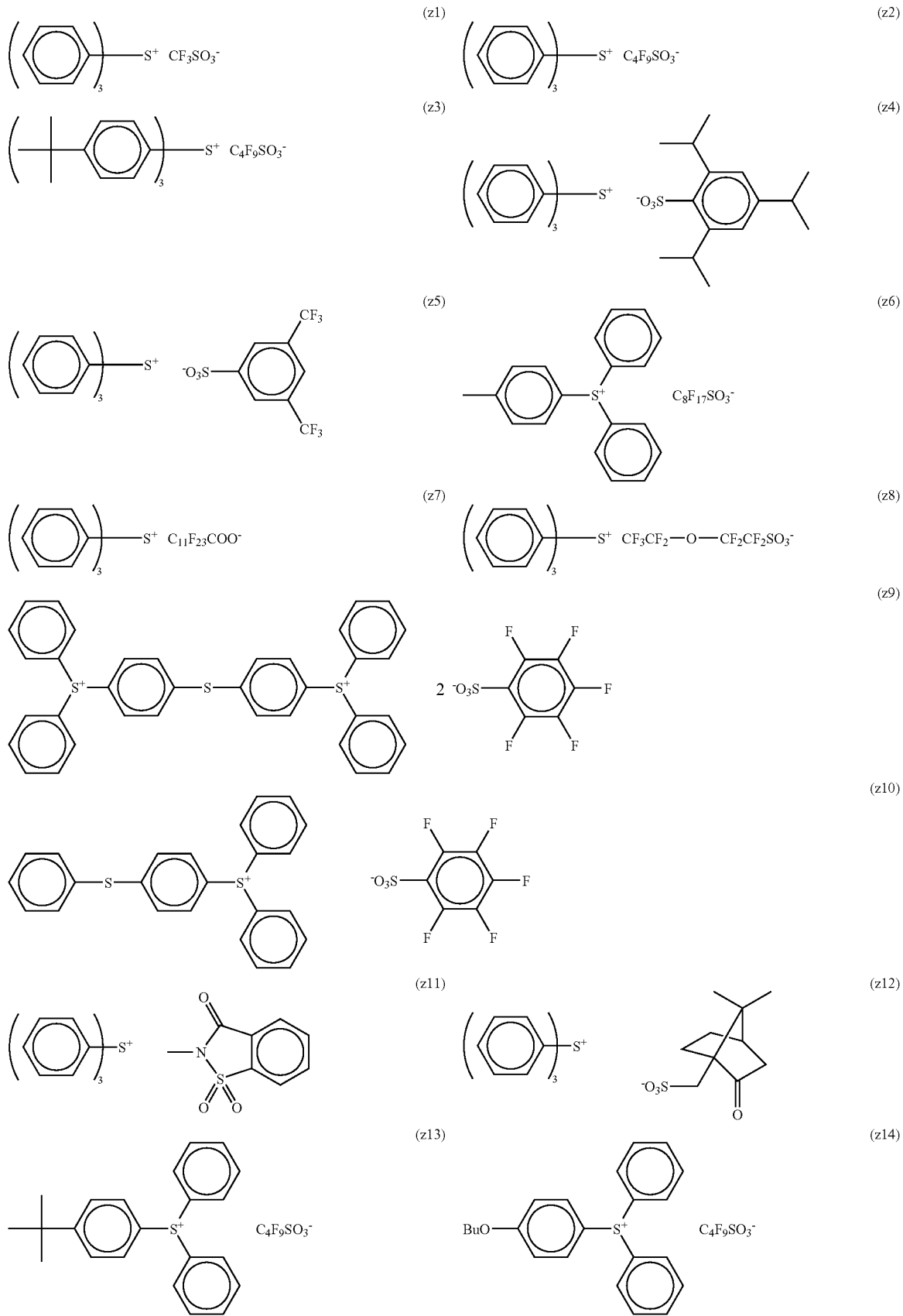

-continued
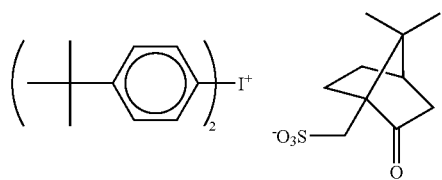 (z15)
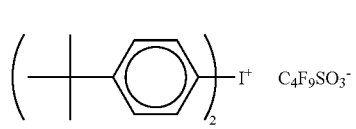 (z16)
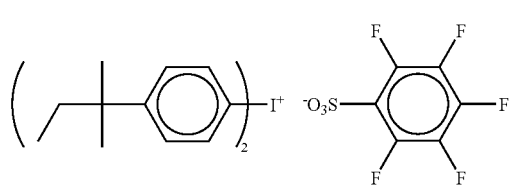 (z17)
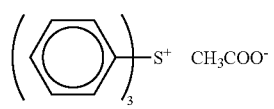 (z18)
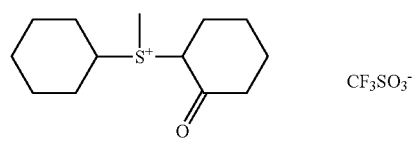 (z19)
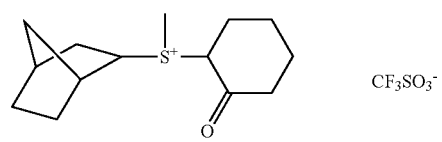 (z20)
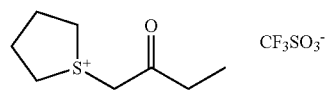 (z21)
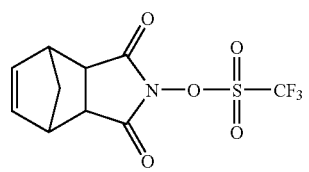 (z22)
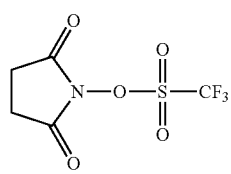 (z23)
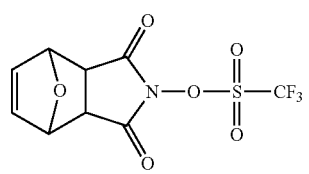 (z24)
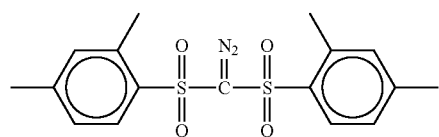 (z25)
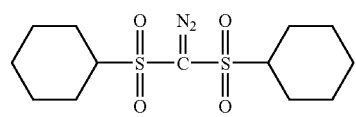 (z26)
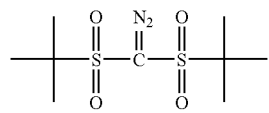 (z27)
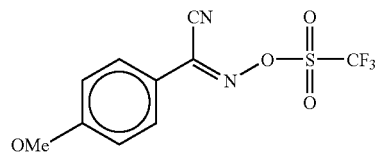 (z28)
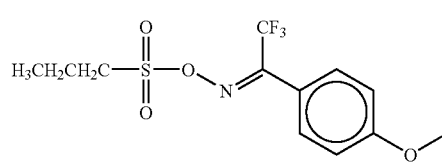 (z29)
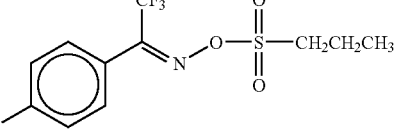 (z30)
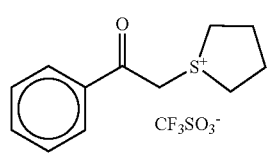 (z31)

-continued
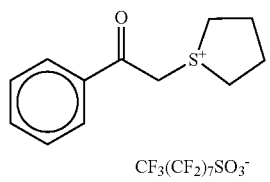
(z32)
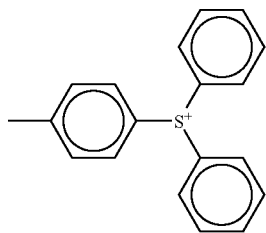
(z33)
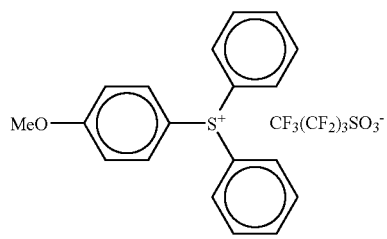
(z34)
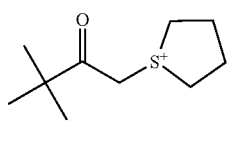
(z35)
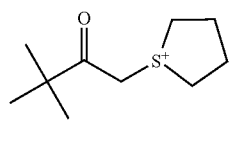
(z36)
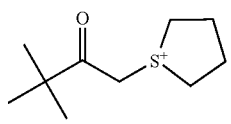
(z37)
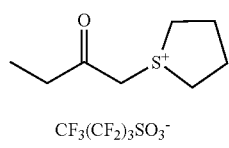
(z38)
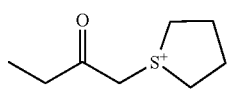
(z39)
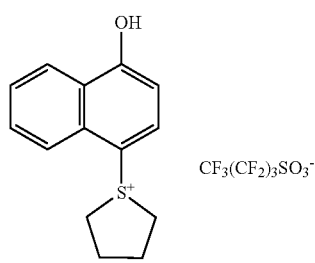
(z40)
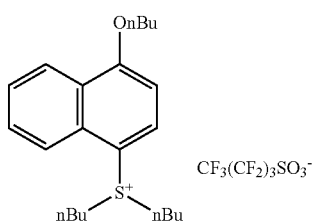
(z41)
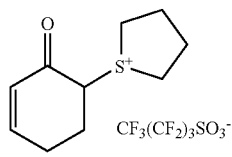
(z42)
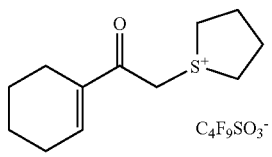
(z43)
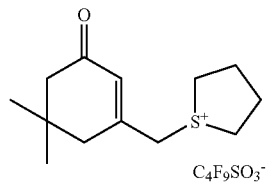
(z44)
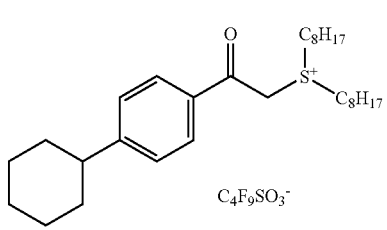
(z45)

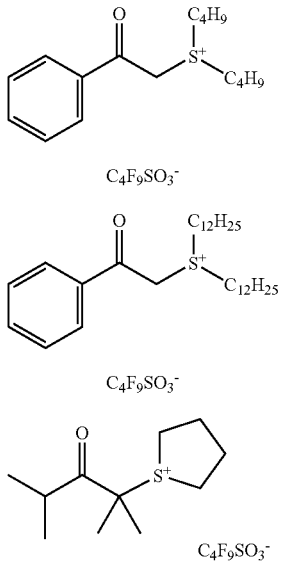
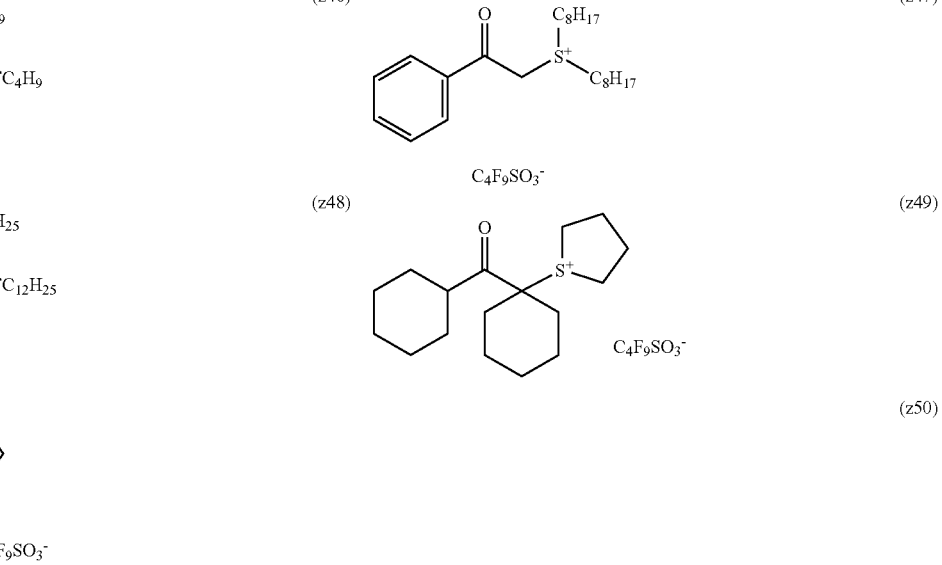

(2) (B) Resin Increasing the Solubility in Alkali Developing Solution by the Action of an Acid (Hereinafter, Referred to as the Component B)

The resin increasing the solubility in alkali developing solution by the action of an acid which is used for the positive type stimulation sensitive composition of the present invention is a resin having a group which can be decomposed by an acid (hereinafter, referred to as the "acid-decomposable group") at the main chain or side chain of the resin or both sides of the main chain or side chain. Among these, a resin having a group which can be decomposed by an acid at the side chain is preferable.

Preferable group as the group which can be decomposed by an acid is a group in which the hydrogen atom of a —COOH group or an —OH group was substituted with a group being eliminated by an acid.

The acid-decomposable group is preferably a silyl ether group, a cumylester group, an acetal group, a tetrahydropyranyl group, an enol ether group, an enolester a tert-alkyl ether group, a tert-alkylester group, a tert-alkylcarbonate group and the like. A tert-alkylester group, a tert-alkylcarbonate group, a cumylester group, an acetal group and a tetrahydropyranyl group are further referable.

The mother body resin when the group which can be decomposed by an acid is bonded as a side chain is an alkali soluble resin having a —COOH or —OH group at a side chain. For example, an alkali soluble resin described later can be mentioned.

The alkali dissolving speed of these alkali soluble resins is preferably 170 A/sec or more which was measured (23° C.) by 0.261N tetramethylammonium hydroxide (TMAH) 330 A/sec or more is preferable in particular.

From the viewpoint, the preferable alkali soluble resin in particular is alkali soluble resins having a hydroxy styrene structure such as o-, m- and p-poly(hydroxy styrene)s and a copolymer thereof, a hydrogenated poly(hydroxy styrene), a halogen or alkyl substituted poly(hydroxy styrene), an o-alkylated polymer or o-acylated polymer of the portion of poly(hydroxy styrene), a styrene-hydroxy styrene copolymer, an α-methylstyrene-hydroxy styrene copolymer, and a hydrogenated novolac resin.

As the repeating unit having the preferable acid-decomposable group in the present invention, for example, tert-butoxycarbonyloxystyrene, 1-alkoxyethoxystyrene, (meth) acrylic acid tert-alkylester and the like can be mentioned.

As disclosed in EP 254853, JP-A-2-25850, JP-A-3-223860, JP-A-4-251259 and the like, the component (B) used for the present invention can be obtained by reacting the alkali soluble resin with the precursor of the group which can be decomposed by an acid, or by polymerizing an alkali soluble resin monomer to which the group which can be decomposed by an acid was bonded, with various monomers.

The specific example of the component (B) used for the present invention is illustrated below, but is not limited these.
P-t-butoxystyrene/p-hydroxystyrene copolymer,
P-(t-butoxycarbonyloxy)styrene/p-hydroxystyrene copolymer,
P-(t-butoxycarbonylmethyloxy)styrene/p-hydroxystyrene copolymer,
P-(t-butoxycarbonylmethyloxy)-3-methylstyrene/4-hydroxy-3-methylstyrene copolymer,
P-(t-butoxycarbonylmethyloxy)styrene/p-hydroxystyren e (10% hydrogenated product) copolymer,
M-(t-butoxycarbonylmethyloxy)styrene/m-hydroxystyrene copolymer,
O-(t-butoxycarbonylmethyloxy)styrene/o-hydroxystyrene copolymer,
P-(cumyloxycarbonylmethyloxy)styrene/p-hydroxystyrene copolymer,
Cumyl methacrylate/methyl methacrylate copolymer,
4-T-butoxycarbonylstyrene/dimethyl maleate copolymer,
Benzyl methacrylate/tetrahydropyranyl methacrylate copolymer,
P-(t-butoxycarbonylmethyloxy)styrene/p-hydroxystyrene/styrene copolymer,
P-t-butoxystyrene/p-hydroxystyrene/fumaronitrile copolymer, T-butoxystyrene/p-hydroxystyrene/hydroxyethyl methacrylate copolymer,
Styrene/N-(4-hydroxyphenyl)maleiimide/N-(4-t-butoxycarbonyloxyphenyl)maleimide copolymer,
P-hydroxystyrene/t-butyl methacrylate copolymer,
Styrene/p-hydroxystyrene/t-butyl methacrylate copolymer,
P-hydroxystyrene/t-butyl acrylate copolymer,
Styrene/p-hydroxystyrene/t-butyl acrylate copolymer,
P-(t-butoxycarbonylmethyloxy)styrene/p-hydroxystyrene/N-methylmaleimide copolymer,
T-butyl methacrylate/1-adamantyl copolymer,
P-hydroxystyrene/t-butyl acrylate/p-acetoxystyrene copolymer,
P-hydroxystyrene/t-butyl acrylate/p-(t-butoxycarbonyloxy)styrene copolymer,
P-hydroxystyrene/t-butyl acrylate/p-(t-butoxycarbonylmethyloxy)styrene copolymer,

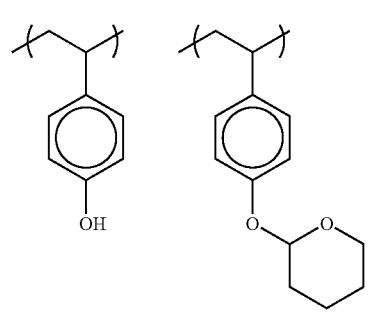
(R-1)

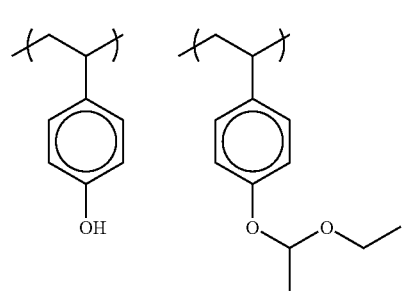
(R-2)

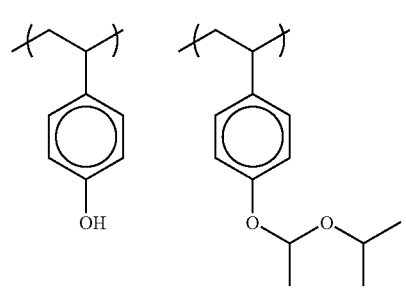
(R-3)

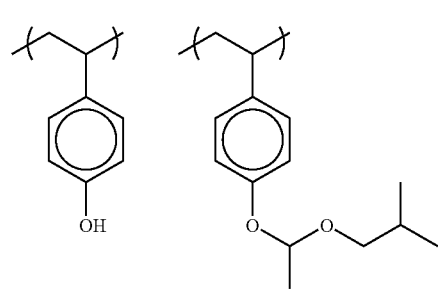
(R-4)

-continued
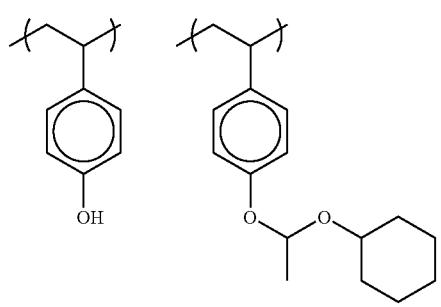 (R-5)
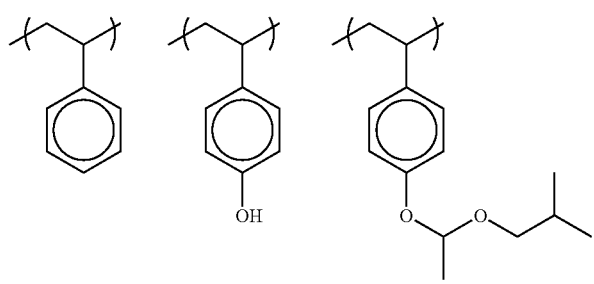 (R-6)
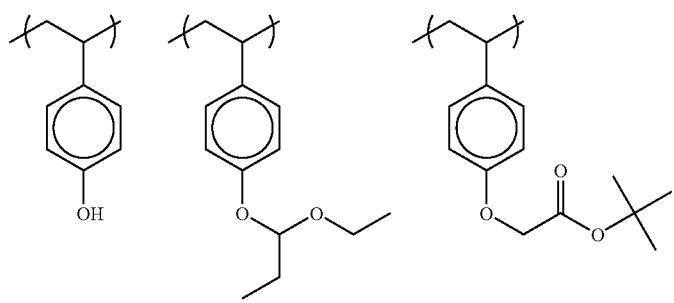 (R-7)
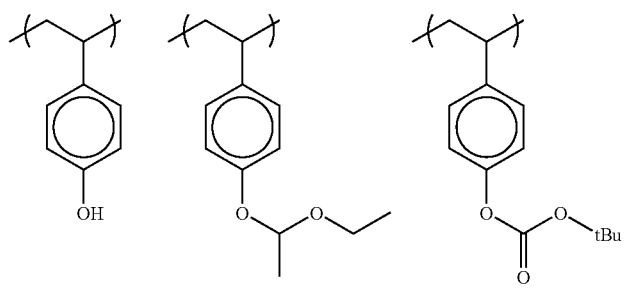 (R-8)
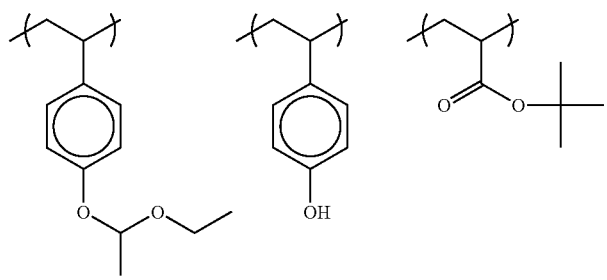 (R-9)

-continued
(R-10)
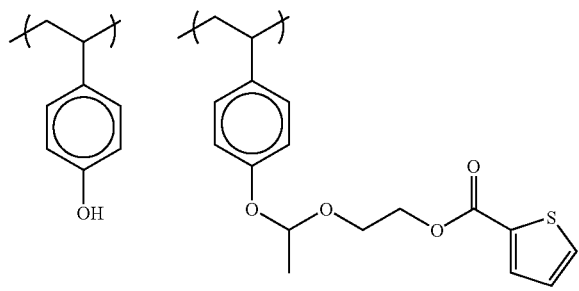
(R-11)
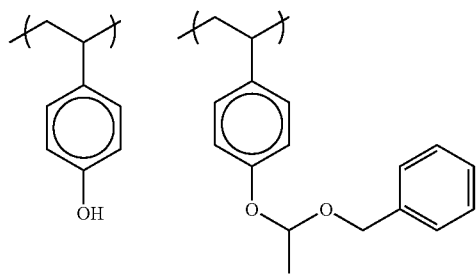
(R-12)
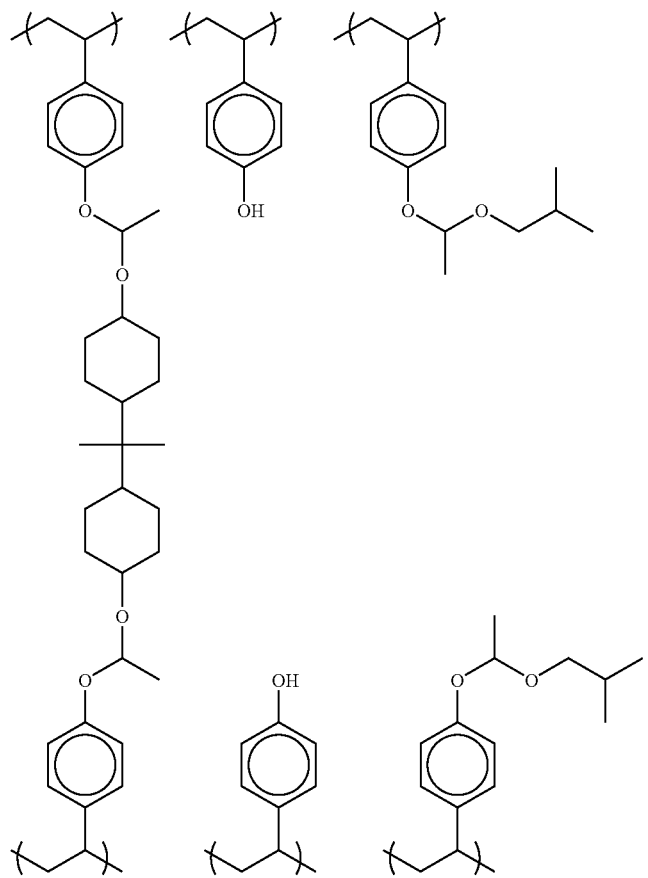

-continued
(R-13)
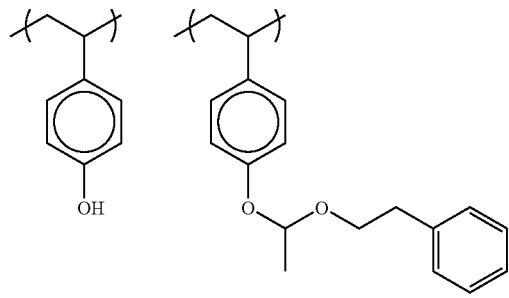
(R-14)
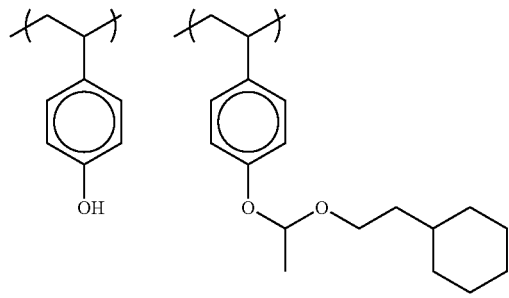
(R-15)
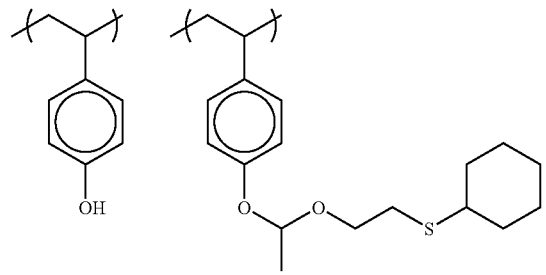
(R-16)
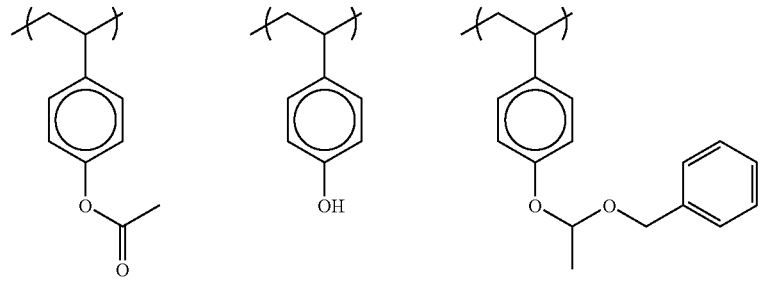
(R-17)
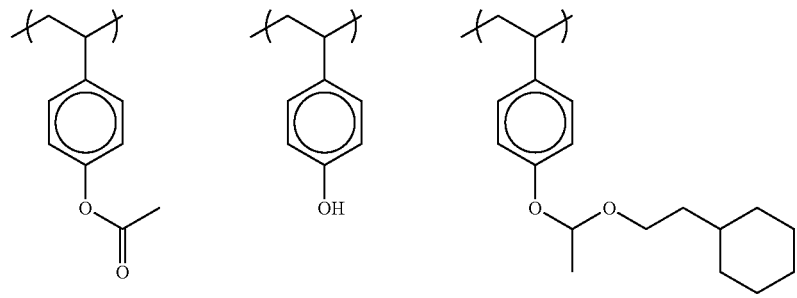

-continued
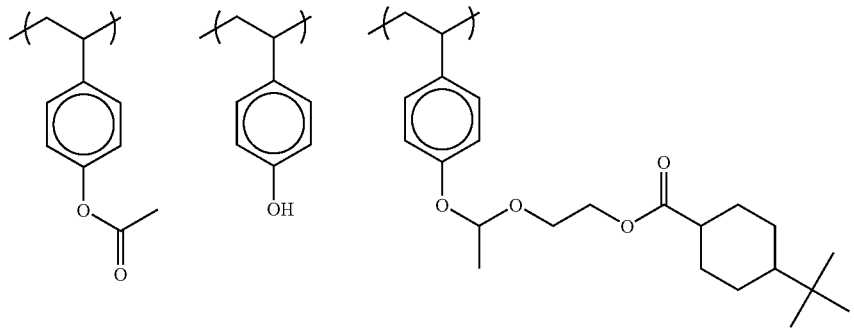
(R-18)
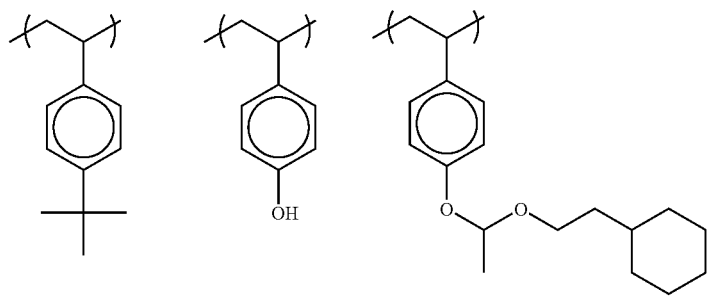
(R-19)
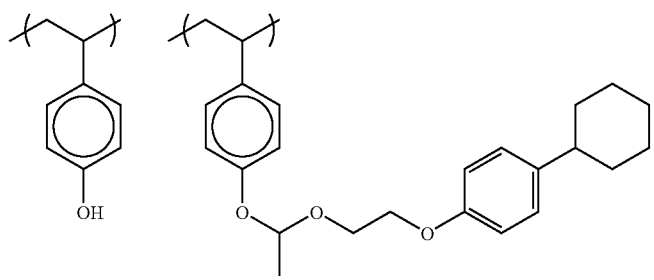
(R-20)
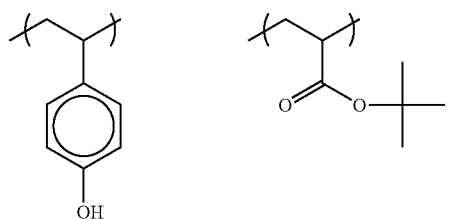
(R-21)
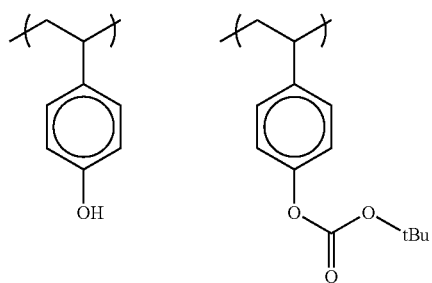
(R-22)

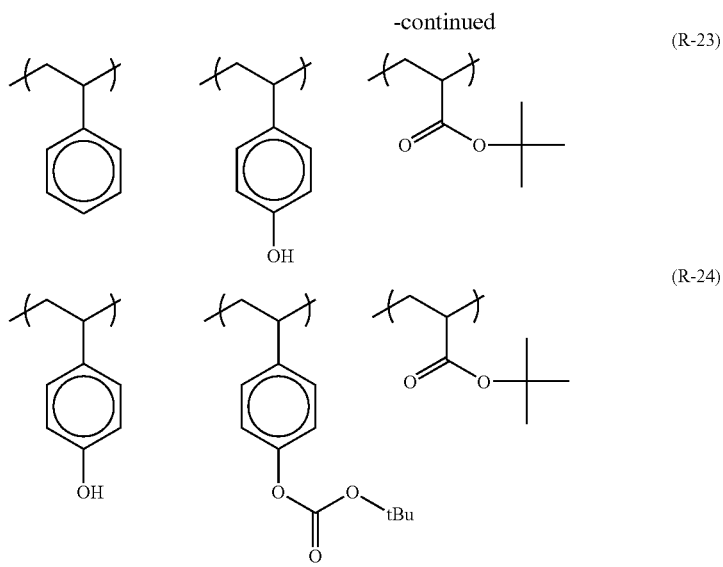

In the above-mentioned specific examples, t-Bu represents a t-butyl group.

The content rate of the group which can be decomposed by an acid is represented by B/(B+S) using (B) the number of the group which can be decomposed by an acid in a resin and (S) the number of the alkali soluble group which is not protected by the group which is eliminated by an acid in a resin. The content rate is preferably 0.01 to 0.7, preferably 0.05 to 0.50 and further preferably 0.05 to 0.40.

When ArF eximer laser beam is irradiated to the positive type stimulation sensitive composition of the present invention, the resin of the component (B) is preferably a resin which has a monocyclic or polycyclic alicyclic hydrocarbon structure, is decomposed by the action of an acid, increases the solubility for an alkali developing solution.

The resin (hereinafter, the "alicyclic hydrocarbon-base acid-decomposable resin") which has a monocyclic or polycyclic alicyclic hydrocarbon structure, is decomposed by the action of an acid, increases the solubility for an alkali developing solution is preferably a resin containing at least one selected from groups of a repeating unit which has a partial structure containing an alicyclic hydrocarbon which is represented by the under-mentioned general formulae (pI) to (pVI), and a repeating unit which is represented by the under-mentioned general formula (II-AB).

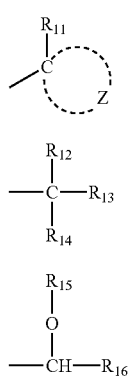

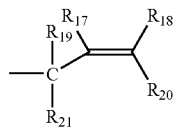

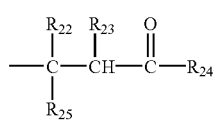

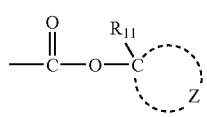

In the formula, $R_{11}$ represents a methyl group, an ethyl group, a n-propyl group, an isopropyl group, a n-butyl group, an isobutyl group or a sec-butyl group, and Z represents an atom group necessary for forming an alicyclic hydrocarbon group together with a carbon atom.

Each of $R_{12}$ to $R_{16}$ independently represents a linear chain or branched alkyl group having 1 to 4 carbon atoms or alicyclic hydrocarbon group, but at least one of $R_{12}$ to $R_{14}$ or either of $R_{15}$ and $R_{16}$ represents an alicyclic hydrocarbon group.

Each of $R_{17}$ to $R_{21}$ independently represents a hydrogen atom, a linear chain or branched alkyl group having 1 to 4 carbon atoms or alicyclic hydrocarbon group, but at least one of $R_{17}$ to $R_{21}$ represents an alicyclic hydrocarbon group. Further, either of $R_{19}$ and $R_{21}$ represents a linear chain or branched alkyl group having 1 to 4 carbon atoms or alicyclic hydrocarbon group.

Each of $R_{22}$ to $R_{25}$ independently represents a linear chain or branched alkyl group having 1 to 4 carbon atoms or alicyclic hydrocarbon group, but at least one of $R_{22}$ to $R_{25}$ represents an alicyclic hydrocarbon group. Further, $R_{23}$ and $R_{24}$ may be bonded to each other to form a ring.

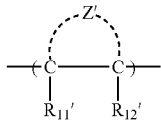
(II-AB)

In the formula (II-AB), each of $R_{11}'$ to $R_{12}'$ independently represents a hydrogen atom, a cyano group, a halogen atom, an alkyl group which may optionally have a substituent.

Z' represents an atomic group for forming an alicyclic structure which includes two carbon atoms (C—C) bonded and may optionally have a substituent.

Further, it is further preferable that the above-mentioned formula (II-AB) is the under-mentioned general formula (II-A) or the general formula (II-B).

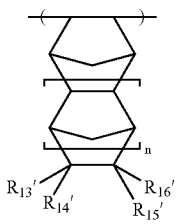
(II-A)

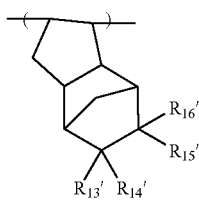
(II-B)

In the formulae (II-A) and (II-B), each of $R_{13}'$ to $R_{16}'$ independently represents a hydrogen atom, a halogen atom, a cyano group, —COOH, —COOR, a group which is decomposed by the action of an acid, —C((=O)—X—A'—$R_{17}'$, or an alkyl group or alicyclic hydrocarbon group which may optionally have a substituent.

Hereat, $R_5$ represents an alkyl group, alicyclic hydrocarbon group which may optionally have a substituent, or the under-mentioned —Y group.

X represents an oxygen atom, a sulfur atom, —NH—, —NHSO$_2$—, or —NHSO$_2$NH—.

A' represents a single bond or a divalent linking group.

Further, a least one of $R_{13}'$ to $R_{16}'$ may be bonded to form a ring, n represents 0 or 1.

$R_{17}'$ represents —COOH, —COOR$_5$, a hydroxy group, an alkoxy group which may optionally have a substituent, —CO—NH—R$_6$, —CO—NH—SO$_2$—R$_6$ or the under-mentioned —Y group.

$R_6$ represents an alkyl group or alicyclic hydrocarbon group which may optionally have a substituent.

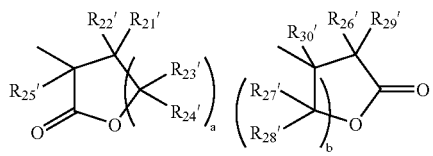

in the —Y group, each of $R_{21}'$ to $R_{30}'$ independently represents a hydrogen atom, or an alkyl group or alicyclic hydrocarbon group which may optionally have a substituent a and b represent 1 or 2.

In the general formulae (pI) to (pVI), the alkyl group in $R_{12}$ to $R_{25}$ may be substituted or not substituted, and represent a linear chain or branched alkyl group having 1 to 4 carbon atoms. As the alkyl group, for example, there are mentioned a methyl group, an ethyl group, a n-propyl group, an isopropyl group, a n-butyl group, an isobutyl group, a sec-butyl group, a tert-butyl group and the like.

As the further substituent of the above-mentioned alkyl group, there can be mentioned an alkoxy group having 1 to 4 carbons, a halogen atom (a fluorine atom, a chlorine atom, a bromine atom, an iodine atom), an acyl group, an acyloxy group, a cyano group, a hydroxy group, a carboxyl group, an alkoxycarbonyl group, a nitro group, and the like.

The alicyclic hydrocarbon group in $R_{12}$ to $R_{25}$ or the alicyclic hydrocarbon group which Z and a carbon atom form may be a monocyclic or a polycyclic group. Specifically, there can be mentioned a group having 5 or more carbon atoms which has monocyclo, bicyclo, tricyclo and tetracyclo structures and the like. The carbon number is preferably 6 to 30 and preferably 7 to 25 in particular. The alicyclic hydrocarbon group may optionally have a substituent.

The structure example of the alicyclic portion among the alicyclic hydrocarbon group is shown below.

(1)

(2)

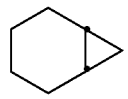
(3)

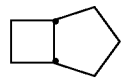
(4)

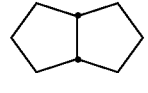
(5)

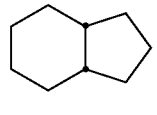
(6)

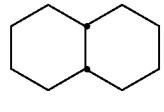
(7)

-continued
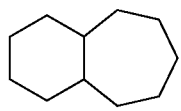
(8)
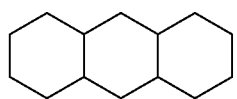
(9)
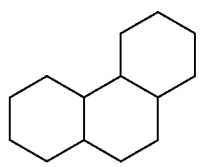
(10)
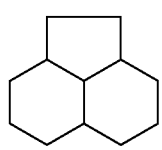
(11)
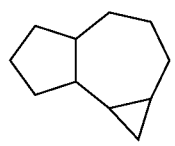
(12)
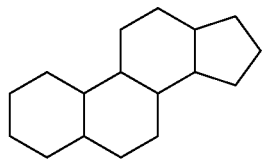
(13)
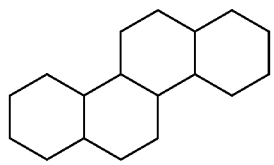
(14)
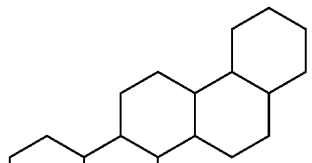
(15)
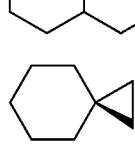
(16)
(17)
(18)
-continued
(19)
(20)
(21)
(22)
(23)
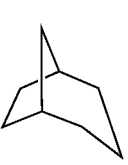
(24)
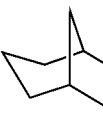
(25)
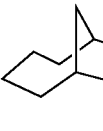
(26)
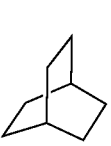
(27)
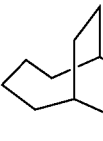
(28)
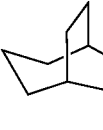
(29)
(30)

-continued

(31) 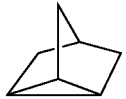

(32) 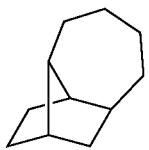

(33) 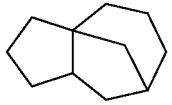

(34) 

(35) 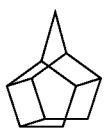

(36) 

(37) 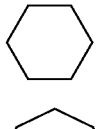

(38) 

(39) 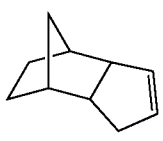

-continued

(42) 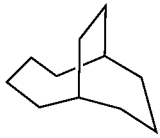

(43) 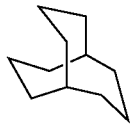

(44) 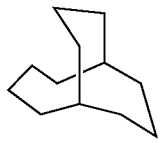

(45) 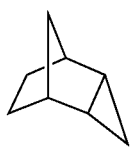

(46) 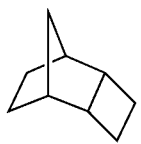

(47) 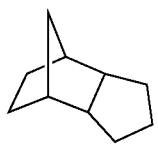

(48) 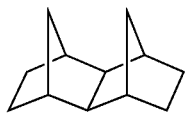

(49) 

(50) 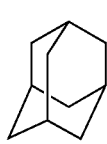

(51) 

In the present invention, the above-mentioned preferable alicyclic portion is an adamantyl group, a noladamantyl group, a decaline residual group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. An adamantyl group, a decaline residual group, a norbornyl group, a cedrol group, a cyclohexyl group, a cycloheptyl group, a cyclooctyl group, a cyclodecanyl group and a cyclododecanyl group are more preferable.

As the substituent of these alicyclic hydrocarbon groups, there are mentioned an alkyl group, a substituted alkyl group, a halogen atom, a hydroxy group, an alkoxy group, a carboxyl group, an alkoxycarbonyl group and the like. The alkyl group is preferably lower alkyl groups such as a methyl group, an ethyl group, a propyl group, an isopropyl group and a butyl group, and more preferably represents a substituent selected from a group consisting of a methyl group, an ethyl group, a propyl group and an isopropyl group. As the substituent of the substituted alkyl group, a hydroxy group, a halogen atom and an alkoxy group can be mentioned. As the above-mentioned alkoxy group, there can be mentioned an alkoxy group having 1 to 4 carbon atoms such as a methoxy group, an ethoxy group, a propoxy group and a butoxy group.

The structure indicated by the general formulae (pI) to (pVI) in the above-mentioned resin can be used for the protection of the alkali soluble group. As the alkali soluble group, known various groups in this technical field are mentioned.

Specifically, a carboxylic acid group, a sulfonic acid group, a phenol group, a thiol group and the like are mentioned and a carboxylic acid group and a sulfonic acid group are preferable.

As the alkali soluble group which was protected by the structure indicated by the general formulae (pI) to (pVI) in the above-mentioned resin, a group represented by the undermentioned general formulae (pVII) to (pXI) is mentioned.

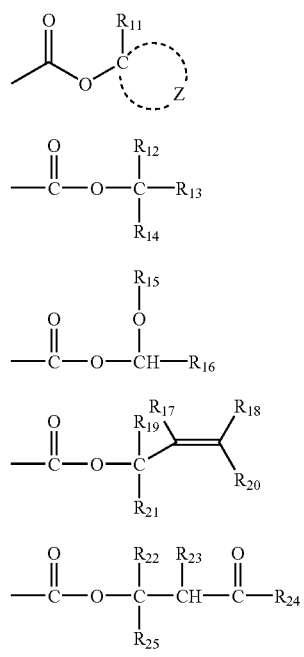

Hereat, $R_{12}$ to $R_{25}$ and Z are respectively the same as the fore-mentioned definition.

In the above-mentioned resin, the repeating unit having the alkali soluble group protected by the structure indicated by the general formulae (pI) to (pVI) is preferably a repeating unit indicated by the under-mentioned general formula (pA).

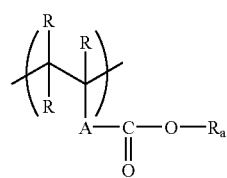

Hereat, R represents a hydrogen atom, a halogen atom, a substituted or unsubstituted linear chain or branched alkyl group having 1 to 4 carbon atoms. A plural number of R's may be respectively the same or different.

A represents one or a combination of 2 or more of groups selected from a group consisting of a single bond, an alkylene group, a substituted alkylene group, an ether group, a thioether group, a carbonyl group, an ester group, an amide group, a sulfoneamide group, a urethane group or a urea group.

Ra represents any one of the above-mentioned formulae (pI) to (pVI)

The specific example of the repeating unit indicated by the general formula (pA) is shown.

In the formulae, Rx is H or $CH_3$.

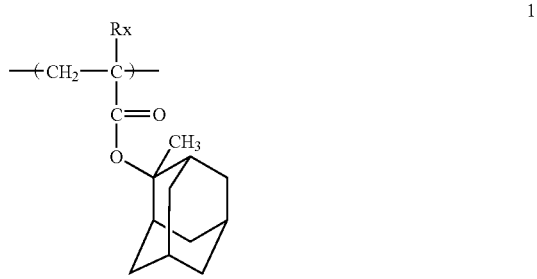

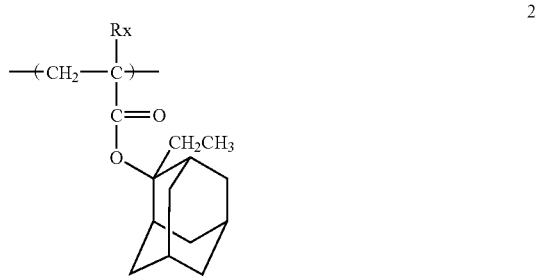

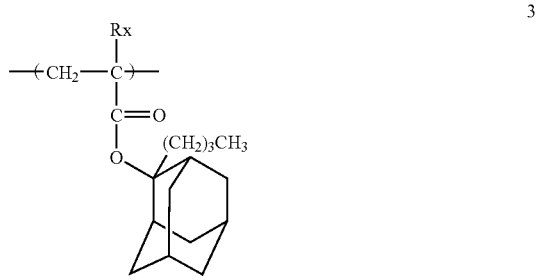

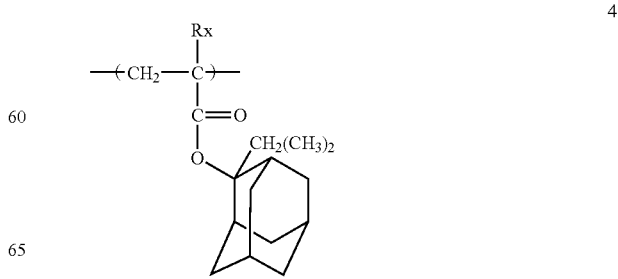

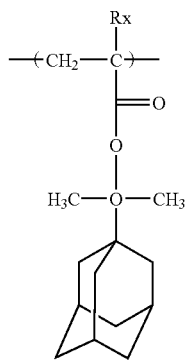
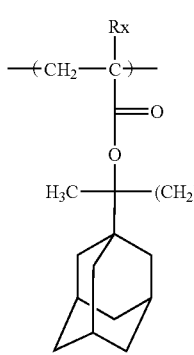
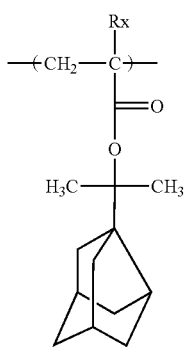
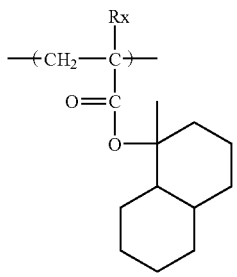
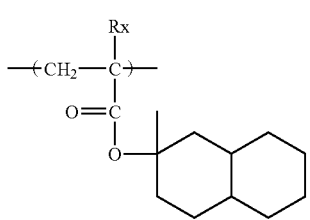
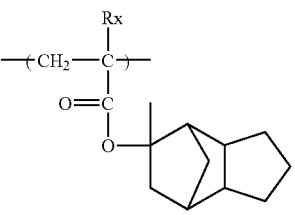
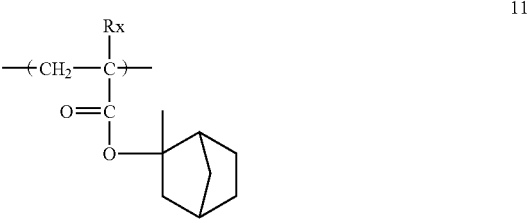
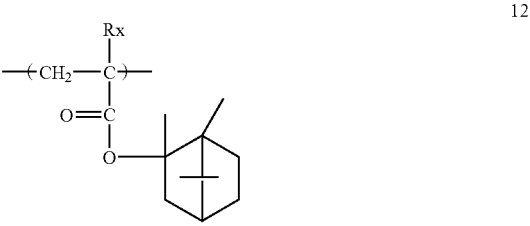
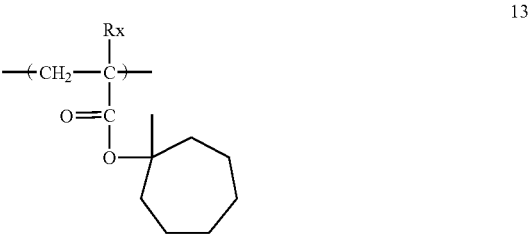
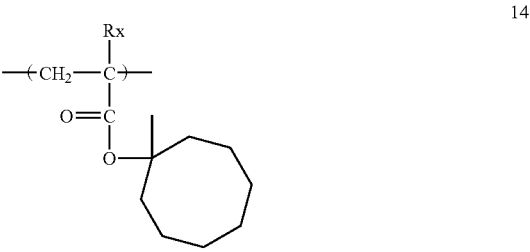
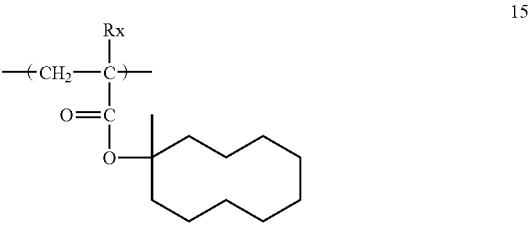
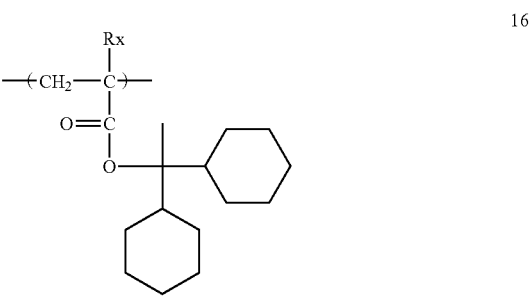

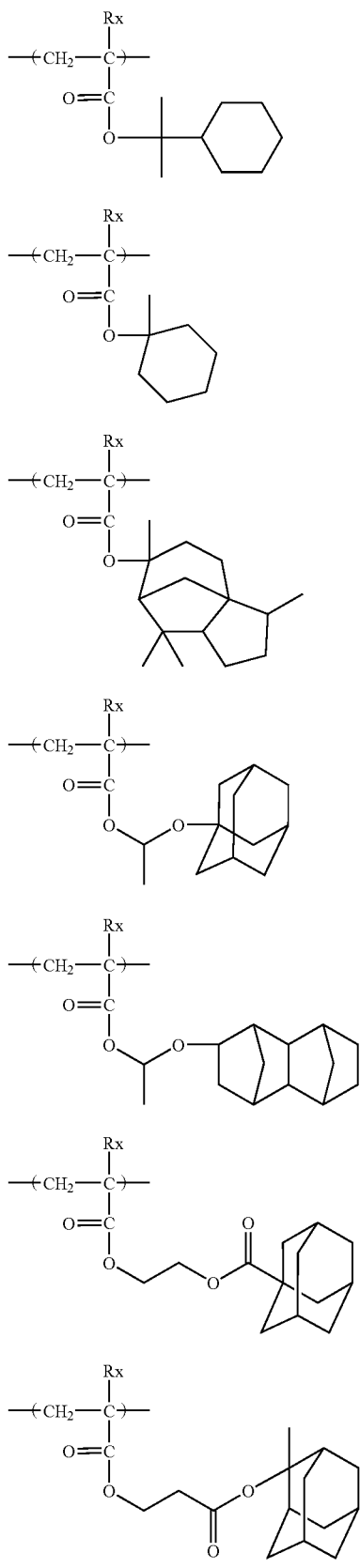

In the above-mentioned formula (II-AB), each of $R_{11}'$ to $R_{12}'$ independently represents a hydrogen atom, a cyano group, a halogen atom, an alkyl group which may optionally have a substituent.

Z' represents an atomic group for forming an alicyclic structure which includes two carbon atoms (C—C) bonded and may optionally have a substituent.

As the halogen atom in the above-mentioned $R_{11}'$ to $R_{12}'$, a fluorine atom, a chlorine atom, a bromine atom, an iodine atom and the like are mentioned.

The alkyl group in the above-mentioned $R_{11}'$, $R_{12}'$, and $R_{21}'$ to $R_{30}'$ is preferably a linear chain or branched alkyl group having 1 to 10 carbon atoms, more preferably a linear chain or branched alkyl group having 1 to 6 carbon atoms, and further preferably a methyl group, an ethyl group, a n-propyl group, an isopropyl group, a n-butyl group, an isobutyl group, a sec-butyl group and a tert-butyl group.

As the further substituent in the above-mentioned alkyl group, there can be mentioned a hydroxy group, a halogen atom, a carboxyl group, an alkoxy group, an acyl group, a cyano group, an acyloxy group and the like. As the halogen atom, a fluorine atom, a chlorine atom, a bromine atom, an iodine atom and the like can be mentioned. As the alkoxy group, an alkoxy group having 1 to 4 carbon atoms such as a methoxy group, an ethoxy group a propoxy group and a butoxy group can be mentioned; as the acyl group, a formyl group, an acetyl group and the like can be mentioned, and as the acyloxy group, an acetoxy group and the like can be mentioned.

The atomic group for forming an alicyclic structure of the above-mentioned Z' is an atomic group which forms in a resin the repeating unit of an alicyclic hydrocarbon which may optionally have a substituent, and preferably an atomic group for forming a bridged alicyclic structure which forms the repeating unit of a bridged alicyclic hydrocarbon.

As the skeleton of the alicyclic hydrocarbon formed, there are mentioned those which are similar as the fore-mentioned structure examples (1) to (51) of the alicyclic portion of $R_{12}$ to $R_{25}$ in the general formulae (pI) to (pVI) and Z' in the general formula (II-AB).

As the preferable bridged alicyclic hydrocarbon, there are mentioned (5), (6), (7), (9), (10), (13), (14), (15), (23), (28), (36), (37), (42) and (47) among the fore-mentioned structure examples.

The skeleton of the above-mentioned bridged alicyclic hydrocarbon may optionally have a substituent. As the substituent, there can be mentioned the $R_{13}'$ to $R_{16}'$ in the fore-mentioned general formula (II-A) or (II-B)

Among the repeating unit having the above-mentioned bridged alicyclic hydrocarbon, a repeating unit represented by the fore-mentioned general formula (II-A) or (II-B) is further preferable.

In the alicyclic hydrocarbon-base acid-decomposable resin related to the present invention, the acid-decomposable group may be contained in the fore-mentioned —C (═O)—X—A'—$R_{17}'$, and may be contained as the substituent of Z' in the general formula (II-AB).

The structure of the acid-decomposable group is represented by —C(═O)—$X_1$—$R_0$.

Wherein as $R_0$, there can be mentioned tertiary-alkyl groups such as t-butyl group and t-amyl group; an isoboronyl group; 1-alkoxyethyl groups such as a 1-ethoxyethyl group, a 1-butoxyethyl group, a 1-isobutoxyethyl group and a 1-cyclohexloxyethyl group; 1-alkoxymethyl groups such as a 1-methoxymethyl group and a 1-ethoxymethyl group; a 3-oxoalkyl group, a tetrahydropyranyl group, a tetrahydrofuranyl group, a trialkylsilylester group, a 3-oxocyclohexylester group, a 2-methyl-2-adamantyl group, a mevaloniclactone group and the like. $X_1$ is the same definition as the above-mentioned X.

As the halogen atom in the above-mentioned $R_{13}'$ to $R_{16}'$, a fluorine atom, a chlorine atom, a bromine atom, an iodine atom and the like can be mentioned;

The alkyl group in the above-mentioned $R_5$, $R_6$, and $R_{13}'$ to $R_{16}'$ is preferably a linear chain or branched alkyl group having 1 to 10 carbon atoms, more preferably a linear chain or branched alkyl group having 1 to 6 carbon atoms, and further preferably a methyl group, an ethyl group, a n-propyl group, an isopropyl group, a n-butyl group, an isobutyl group, a sec-butyl group and a tert-butyl group.

The cyclic hydrocarbon group in the above-mentioned $R_5$, $R_6$, and $R_{13}'$ to $R_{16}'$ is, for example, a cyclic alkyl group, and a bridged hydrocarbon, and there can be mentioned a cyclopropyl group, a cyclopentyl group, a cyclohexyl group, an adamantyl group, a 2-methyl-2-adamantyl group, a norbornyl group, a boronyl group, an isoboronyl group, a tricyclodecanyl group, a dicyclocyclopentyl group, a norbornaneepoxy group, a menthyl group, an isomenthyl group, a neomenthyl group, a tetracyclododecanyl group and the like.

As the ring which at least 2 of the above-mentioned $R_{13}'$ to $R_{16}'$ are bonded to form, there are mentioned rings having 5 to 12 carbon atoms such as cyclopentene, cyclohexene, cycloheptane and cyclooctane As the alkoxy group in the above-mentioned $R_{17}'$, there can be mentioned alkoxy groups having 1 to 4 carbon atoms such as a methoxy group, an ethoxy group, a propoxy group and a butoxy group.

As the substituent of the above-mentioned alkyl group, cyclic hydrocarbon group and alkoxy group, there can be mentioned a hydroxy group, a halogen atom, a carboxyl group, an alkoxy group, an acyl group, a cyano group, an acyloxy group, an alkyl group, an cyclic hydrocarbon group and the like. As the halogen atom, a fluorine atom, a chlorine atom, a bromine atom, an iodine atom and the like can be mentioned. As the alkoxy group, an alkoxy group having 1 to 4 carbon atoms such as a methoxy group, an ethoxy group a propoxy group and a butoxy group can be mentioned. As the acyl group, a formyl group, an acetyl group and the like can be mentioned. As the acyloxy group, an acetoxy group and the like can be mentioned.

Further, as the alkyl group and cyclic hydrocarbon group, those described above can be mentioned.

As the divalent linking group of the above-mentioned A', one or a combination of 2 or more of groups selected from a group consisting of an alkylene group, a substituted alkylene group, an ether group, a thioether group, a carbonyl group, an ester group, an amide group, a sulfoneamide group, a urethane group or a urea group.

As the alkylene group and substituted alkylene group in the above-mentioned A', a group represented by the under-mentioned formula can be mentioned.

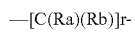

—[C(Ra)(Rb)]r-

In the formula, Ra and Rb represent a hydrogen atom, an alkyl group, a substituted alkyl group, a halogen atom, a hydroxy group and an alkoxy group, and both may be the same or different. As the alkyl group, lower alkyl groups such as a methyl group, an ethyl group, a propyl group, an isopropyl group and a butyl group are preferable, and it is further preferably selected from a methyl group, an ethyl group, a propyl group and an isopropyl group. As the substituent of a substituted alkyl group, a hydroxy group, a halogen atom and an alkoxy group can be mentioned. As the alkoxy group, alkoxy groups having 1 to 4 carbon atoms such as a methoxy group, an ethoxy group a propoxy group and a butoxy group can be mentioned. As the halogen atom, a fluorine atom, a chlorine atom, a bromine atom, an iodine atom and the like can be mentioned. R represents an integer of 1 to 10.

In the alicyclic hydrocarbon-base acid-decomposable resin related to the present invention, the group decomposed by the action of an acid can be contained in at least one of the repeating units among a repeating unit which has a partial structure containing an alicyclic hydrocarbon which is represented by the fore-mentioned general formulae (pI) to (pVI), a repeating unit which is represented by the under-mentioned general formula (II-AB), and a repeating unit of a copolymerization component described later.

The various substituents in $R_{13}'$ to $R_{16}'$ in the above-mentioned general formula (II-A) or general formula (II-B) become the substituent of the atomic group for forming the alicyclic structure in the above-mentioned general formula (II-AB), or the substituent of the atomic group Z for forming the bridged alicyclic structure.

As the specific example of the repeating unit represented by the above-mentioned general formula (II-A) or general formula (II-B), the following repeating units are mentioned but the present invention is not limited to these specific examples.

[II-1]

[II-2]

[II-3]

[II-4]

[II-5]

[II-6]

-continued
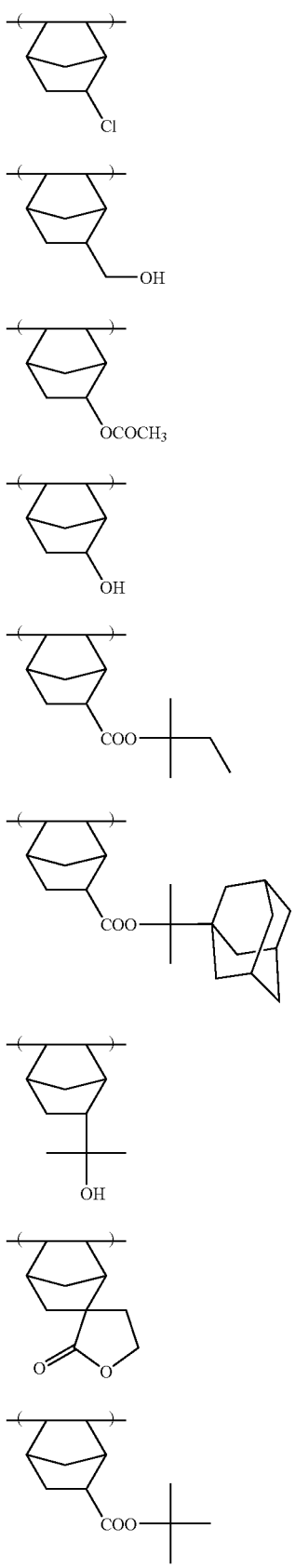
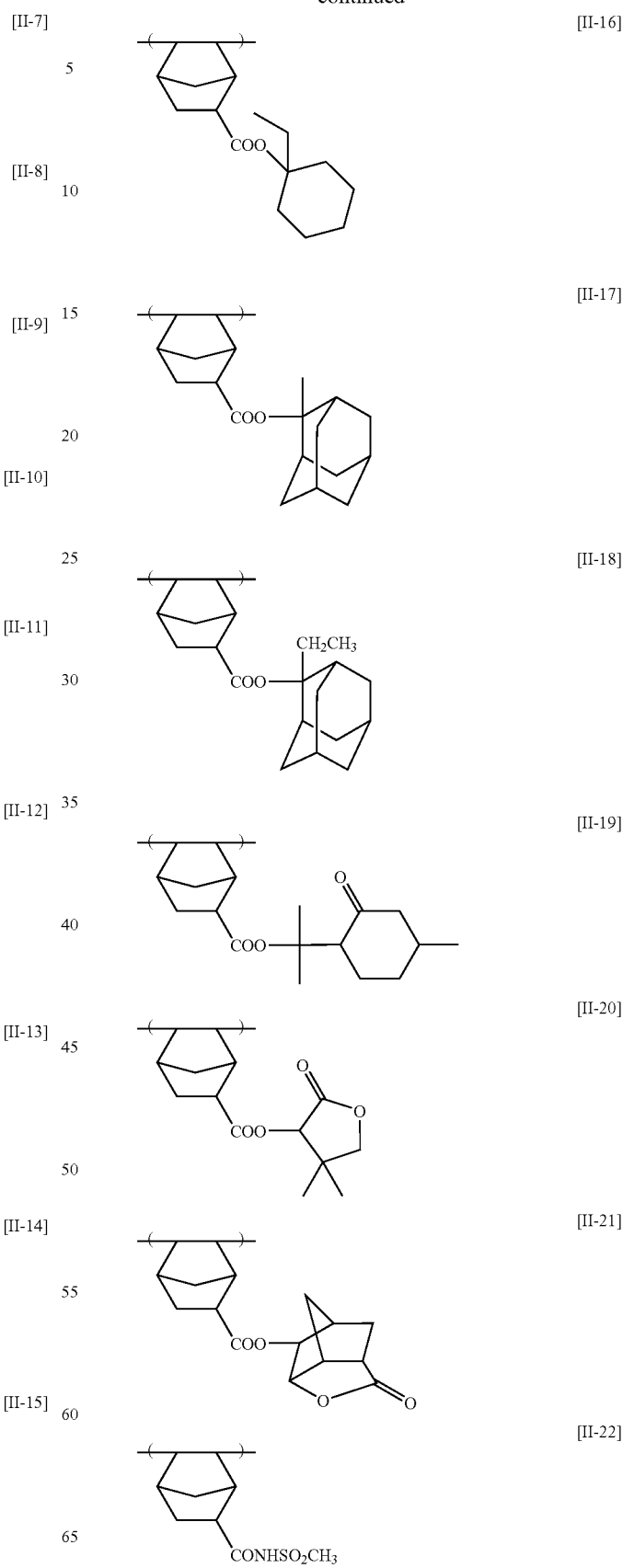

[II-23] 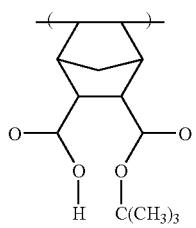

[II-24] 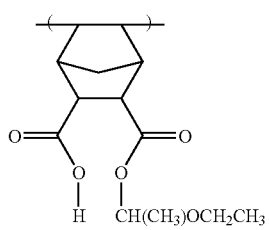

[II-25] 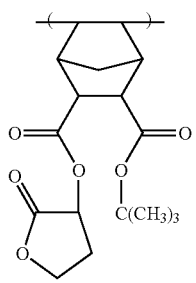

[II-26] 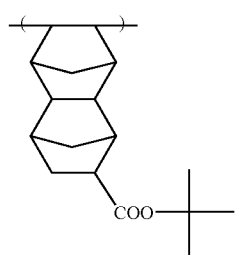

[II-27] 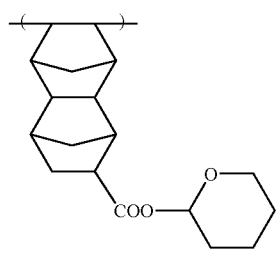

[II-28] 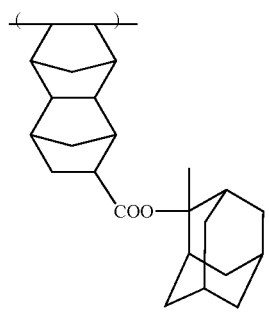

[II-29] 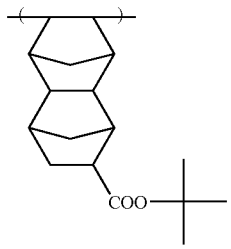

[II-30] 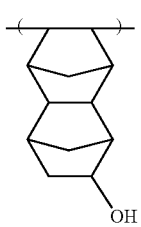

[II-31] 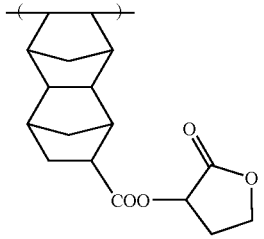

[II-32] 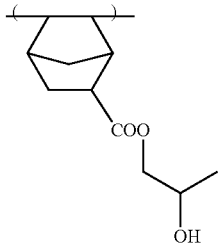

The alicyclic hydrocarbon-base acid-decomposable resin of the present invention has preferably a lactone group, and has more preferably a repeating unit having a group having a lactone structure which is represented by either of the under-mentioned general formula (Lc) or the under-mentioned general formulae (V-1) to (V-5) The group having a lactone structure may be directly bonded with a main chain.

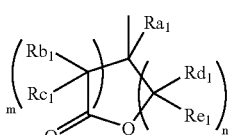 (Lc)

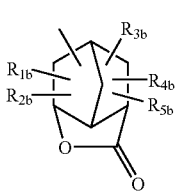 (V-1)

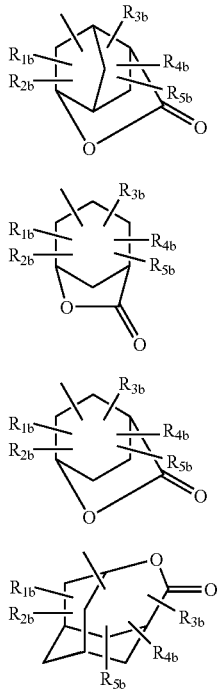

(V-2)

(V-3)

(V-4)

(V-5)

In the general formula (Lc), each of $Ra_1$, $Rb_1$, $Rc_1$, $Rd_1$ and $Re_1$ independently represents a hydrogen atom or an alkyl group which may optionally have a substituent. Each of m and n independently represents an integer of o to 3, and m+n is 2 or more and 6 or less.

In the general formulae (V-1) to (V-5), each of $R_{1b}$ to $R_{5b}$ independently represents a hydrogen atom or an alkyl group, cycloalkyl group, alkoxy group, alkoxycarbonyl group, alkylsulfonyl group, alkylsulfonylimino group or alkenyl group which may optionally have a substituent. Two of $R_{1b}$ to $R_{5b}$ may be bonded to form a ring.

As the alkyl groups of $Ra_1$ to $Re_1$ in the general formula (Lc) and the alkyl group of the alkyl group, cycloalkyl group, alkoxy group, alkoxycarbonyl group, alkylsulfonyl group and alkylsulfonylimino group of $R_{1b}$ to $R_{5b}$ in the general formulae (V-1) to (V-5), a linear chain or branched alkyl group is mentioned and may have a substituent.

The linear chain or branched alkyl group is a linear chain or branched alkyl group having 1 to 12 carbon atoms, more preferably a linear chain or branched alkyl group having 1 to 10 carbon atoms, and further preferably a methyl group, an ethyl group, a propyl group, an isopropyl group, a n-butyl group, an isobutyl group, a sec-butyl group and a tert-butyl group, a pentyl group, a hexyl group, a heptyl group, an octyl group, a nonyl group and a decyl group.

The cycloalkyl group in $R_{1b}$ to $R_{5b}$ is preferably cycloalkyl groups having 3 to 8 carbon atoms such as a cyclopropyl group, a cyclopentyl group, a cyclohexyl group, a cycloheptyl group and an octyl group.

The alkenyl group in $R_{1b}$ to $R_{5b}$ is preferably alkenyl groups having 2 to 6 carbon atoms such as a vinyl group, a propenyl group, a ptenyl group and a hexenyl group.

Further, as the ring which 2 of $R_{1b}$ to $R_{5b}$ are bonded to form, there are mentioned rings having 3 to 8 carbon atoms such as a cyclopropane ring, a cyclobutane ring, a cyclopentane ring, a cyclohexane ring and a cyclooctane ring.

Further, $R_{1b}$ to $R_{5b}$ in the general formulae (V-1) to (V-5) may be bonded to any one of carbon atoms which constitute the ring skeleton.

As the preferable substituent which the alkyl group of $R_{a1}$ to $R_{e1}$ and the alkyl group, cycloalkyl group, alkoxy group, alkoxycarbonyl group, alkylsulfonylimino group and alkenyl group of $R_{1b}$ to $R_{5b}$ may optionally have, there can be mentioned an alkoxy group having 1 to 4 carbon atoms, a halogen atom (a fluorine atom, a chlorine atom, a bromine atom, an iodine atom), an acyl group having 2 to 5 carbons, an acyloxy group having 2 to 5 carbon atoms, a cyano group, a hydroxy group, a carboxyl group, an alkoxycarbonyl group having 2 to 5 carbon atoms, and a nitro group.

As the repeating unit having a group having a lactone structure which is represented by either of the general formula (Lc) or the general formulae (V-1) to (V-5), there can be mentioned those which have a group in which at least one among $R_{13}'$ to $R_{16}'$ in the above-mentioned general formula (II-A) or general formula (II-B) has a group represented by the general formula (Lc) or the general formulae (V-1) to (V-5) (for example, $R_5$ of —$COOR_5$ represents a group represented by the general formula (Lc) or the general formulae (V-1) to (V-5)), or the repeating unit represented by the under-mentioned general formula (AI), and the like.

(AI)

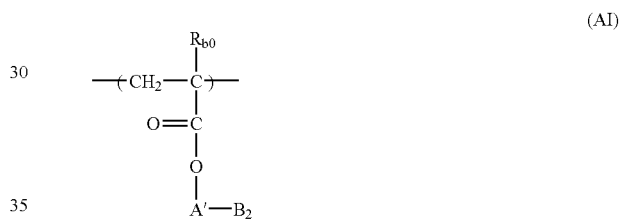

In the general formula (AI), $R_{b0}$ represents a hydrogen atom, a halogen atom or a substituted or unsubstituted alkyl group having 1 to 4 carbon atoms. As the preferable substituent which the alkyl group of $R_{b0}$ may optionally have, there are mentioned those which were previously exemplified as the preferable substituent which the alkyl group as $R_{1b}$ in the general formulae (V-1) to (V-5) may optionally have.

As the halogen atom of $R_{b0}$, a fluorine atom, a chlorine atom, a bromine atom, an iodine atom and the like are mentioned. $R_{b0}$ is preferably a hydrogen atom.

A' represents a single bond, an ether group, an ester group, a carbonyl group, an alkylene group, or a divalent group combining thereof.

$B_2$ represents a group represented by either of the general formula (Lc) or the general formulae (V-1) to (V-5). As said divalent group combining thereof in A', for example, those represented by the under-mentioned formula is mentioned.

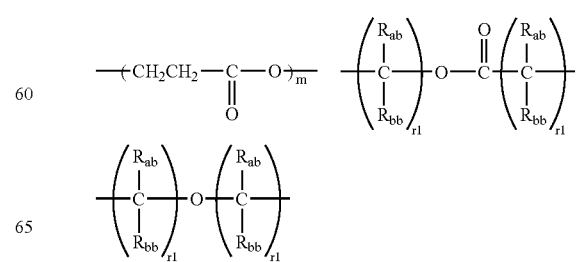

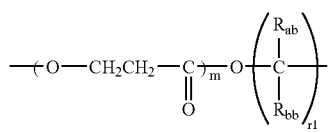

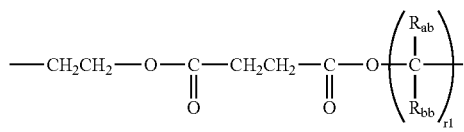

In the above-mentioned formula, $R_{ab}$ and $R_{bb}$ represent a hydrogen atom, an alkyl group, a substituted alkyl group, a halogen atom, a hydroxy group and an alkoxy group, and both may be the same or different.

As the alkyl group, low alkyl groups such as a methyl group, an ethyl group, a propyl group, an isopropyl group and a butyl group are preferable, and further preferably selected from a methyl group, an ethyl group, a propyl group and an isopropyl group. As the substituent of the substituted alkyl group, a hydrogen atom, a halogen atom and an alkoxy group having 1 to 4 carbon atoms are mentioned.

As the alkoxy group, alkoxy groups having 1 to 4 carbon atoms such as a methoxy group, an ethoxy group a propoxy group and a butoxy group can be mentioned. As the halogen atom, a fluorine atom, a chlorine atom, a bromine atom, an iodine atom and the like are mentioned. R1 represents an integer of 1 to 10, and preferably an integer of 1 to 4. M represents an integer of 1 to 3, and preferably an integer of 1 or 2.

The specific examples of the repeating unit having a group having a lactone structure are mentioned below, but the present invention is not limited to these.

In the following formulae, Rx is H or $CH_3$.

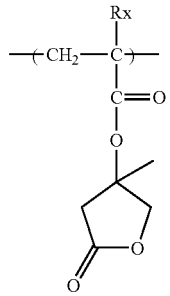
(IV-1)

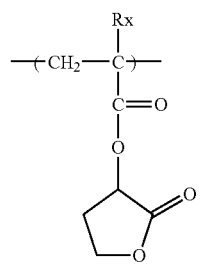
(IV-2)

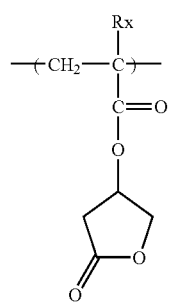

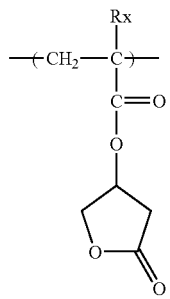
(IV-3)

(IV-4)

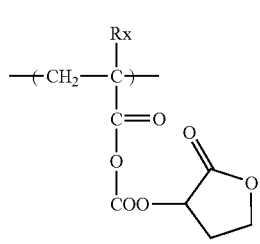
(IV-5)

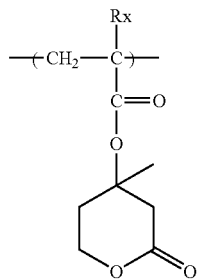
(IV-6)

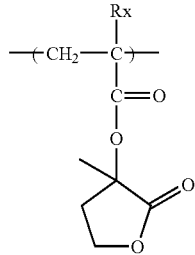
(IV-7)

(IV-8) 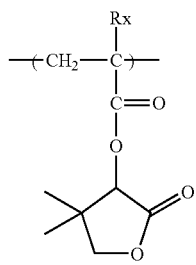
(IV-9) 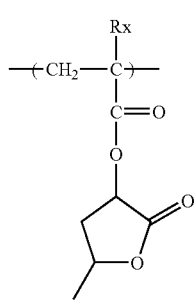
(IV-10) 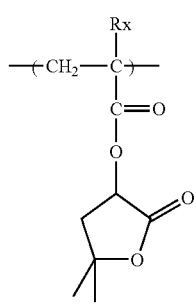
(IV-11) 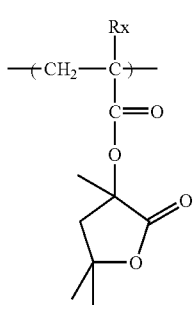
(IV-12) 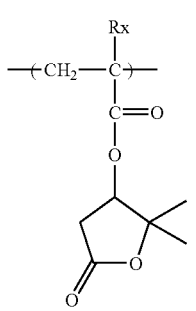
(IV-13) 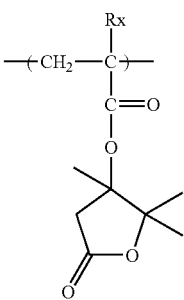
(IV-14) 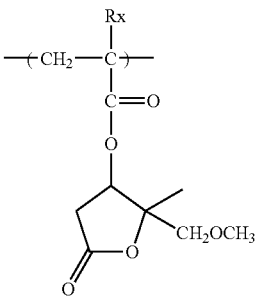
(IV-15) 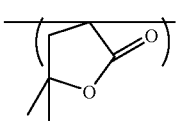
(IV-16) 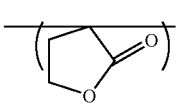
(Ib-1) 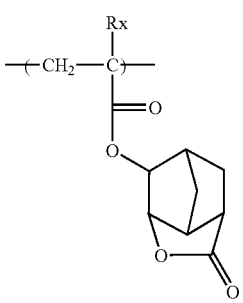
(Ib-2) 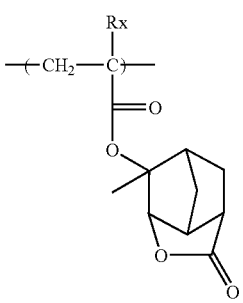

-continued
(Ib-3)
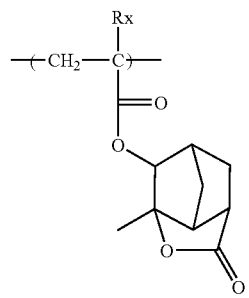
(Ib-4)
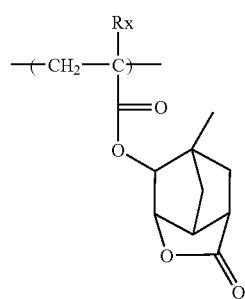
(Ib-5)
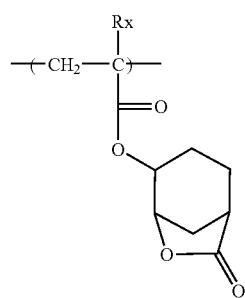
(Ib-6)
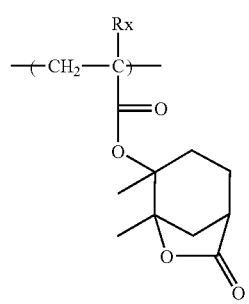
(Ib-7)
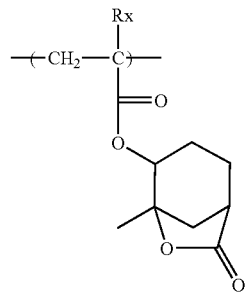
-continued
(Ib-8)
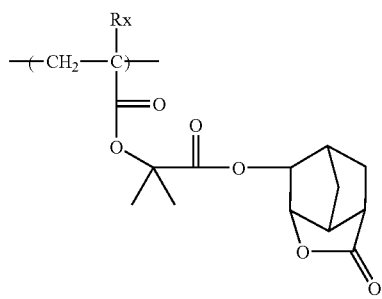
(Ib-9)
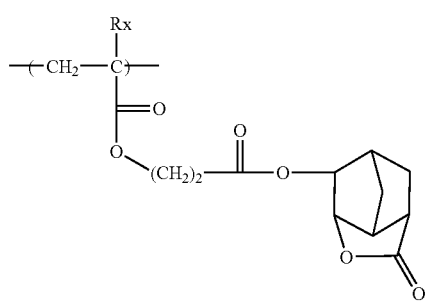
(Ib-10)
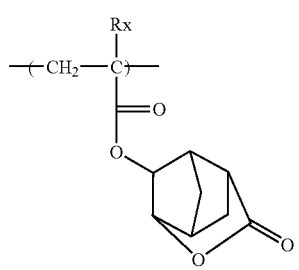
(Ib-11)
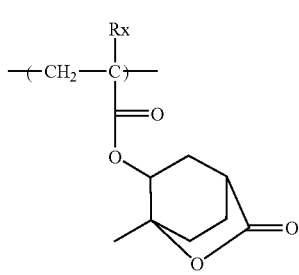
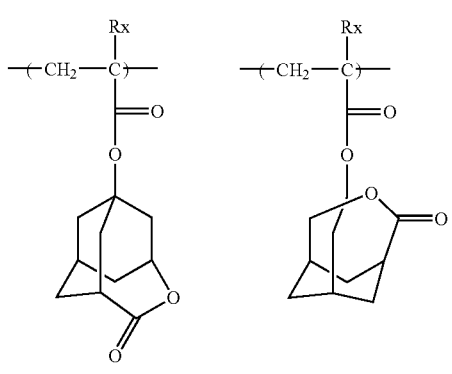

-continued

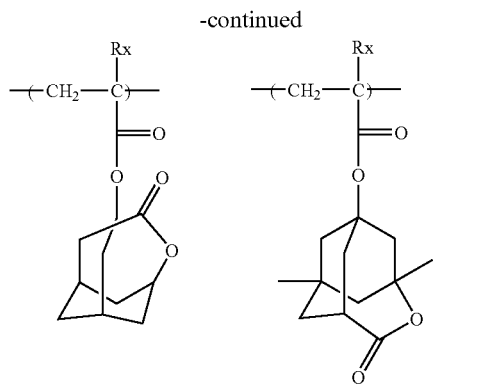
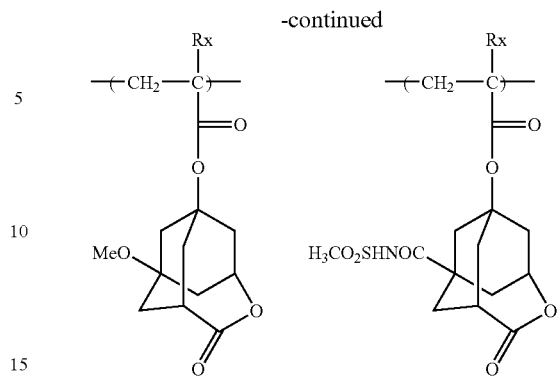

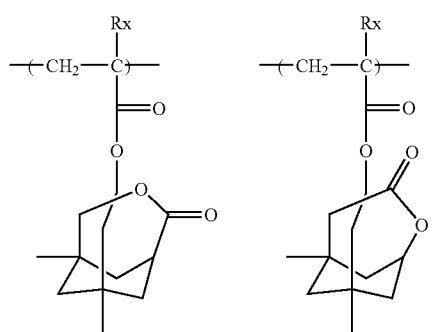

The alicyclic hydrocarbon-base acid-decomposable resin of the present invention may contain the repeating unit which has a group represented by the under-mentioned general formula (VII).

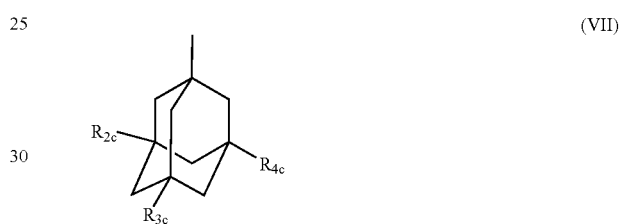

(VII)

In the general formula (VII) each of $R_{2c}$ to $R_{4c}$ independently represents a hydrogen atom or a hydroxy group. Provided that at least one of $R_{2c}$ to $R_{4c}$ represent a hydroxy group.

The group represented by the general formula (VII) is preferably a dihydroxy body and a monohydroxy body and more preferably a dihydroxy body.

As the repeating unit having a group represented by the general formula (VII), there can be mentioned those which have a group in which at least one among $R_{13}'$ to $R_{16}'$ in the above-mentioned general formula (II-A) or general formula (II-B) has a group represented by the general formula (VII) or the general formulae (V-1) to (V-5) (for example, $R_5$ of —COOR$_5$ represents a group represented by the general formula (VII)), or the repeating unit represented by the under-mentioned general formula (AII), and the like.

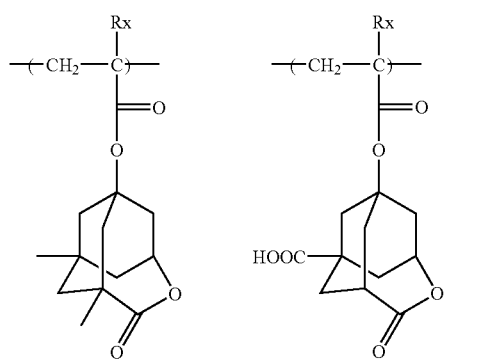

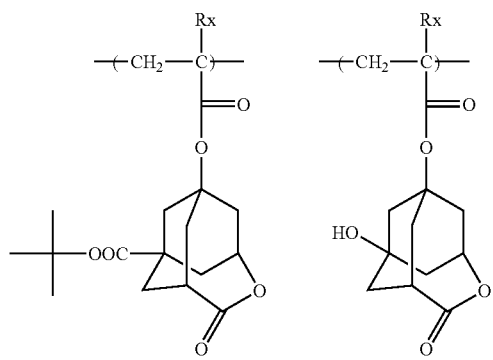

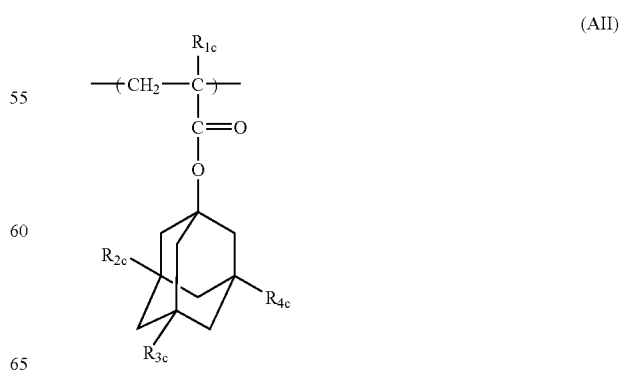

(AII)

In the general formula (AII), $R_{1c}$ represents a hydrogen atom or a methyl group.

Each of $R_{2c}$ to $R_{4c}$ independently represents a hydrogen atom or a hydroxy group. Provided that at least one of $R_{2c}$ to $R_{4c}$ represent a hydroxy group. Provided that at least one of $R_{2c}$ to $R_{4c}$ represent a hydroxy group.

The specific examples of the repeating unit having the structure represented by the general formula (AII) are mentioned below, but they are not limited to these.

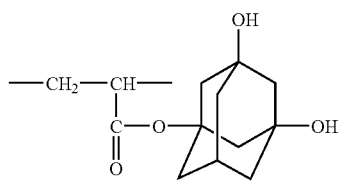
(1)

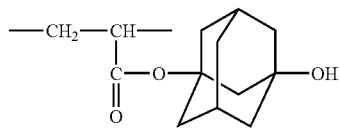
(2)

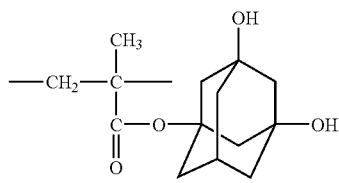
(3)

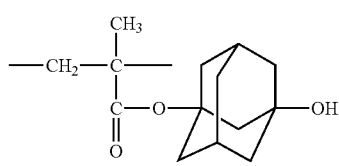
(4)

The alicyclic hydrocarbon-base acid-decomposable resin of the present invention may contain the repeating unit represented by the under-mentioned general formula (VIII).

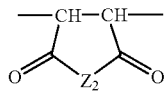
(VIII)

In the above-mentioned general formula (VIII), $Z_2$ represents —O— or —N($R_{41}$)—. $R_{41}$ represents a hydrogen atom, a hydroxy group, an alkyl group, a haloalkyl group or —OSO$_2$—$R_{42}$. $R_{41}$ represents an alkyl group, a haloalkyl group, a cycloalkyl group or a camphor group.

The alkyl group in the above-mentioned $R_{41}$ and $R_{42}$ is preferably a linear chain or branched alkyl group having 1 to 10 carbon atoms, more preferably a linear chain or branched alkyl group having 1 to 6 carbon atoms, and further preferably a methyl group, an ethyl group, a propyl group, an isopropyl group, a n-butyl group, an isobutyl group, a sec-butyl group and a tert-butyl group.

As the haloalkyl group in the above-mentioned $R_{41}$ and $R_{42}$, there can be mentioned a trifluoromethyl group, a nanofluoromethyl group, a pentadecafluoromethyl group, a trichloromethyl group and the like. As the cycloalkyl group in the above-mentioned $R_{42}$, there can be mentioned a cyclopentyl group, a cyclohexyl group, a cyclooctyl group and the like.

The alkyl group and haloalkyl group as $R_{41}$ to $R_{42}$ and the cycloalkyl group and camphor residual group as $R_{42}$ may optionally have a substituent. As the substituent, for example, there can be mentioned a hydroxy group, a carboxyl group, a halogen atom (for example, a fluorine atom, a chlorine atom, a bromine atom, and an iodine atom), a alkoxy group (preferably, an alkoxy group having 1 to 4 carbon atoms, for example, a methoxy group, an ethoxy group a propoxy group, a butoxy group and the like), an acyl group (preferably, an acyl group having 2 to 5 carbon atoms, for example, a formyl group, an acetyl group and the like), an acyloxy group (preferably, an acyloxy group having 2 to 5 carbon atoms, for example, an acetoxy group), an aryl group (preferably, an aryl group having 6 to 14 carbon atoms, for example, a phenyl group), and the like.

As the specific example of the repeating unit represented by the above-mentioned general formula (VIII), the following repeating units [I'-1] to [I'-7] are mentioned but the present invention is not limited to these specific examples.

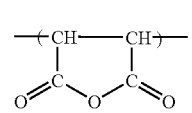
[I'-1]

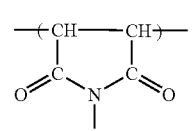
[I'-2]

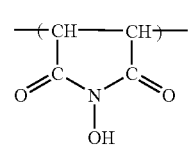
[I'-3]

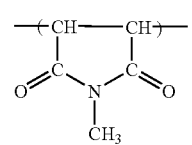
[I'-4]

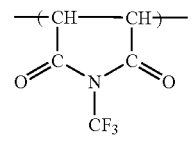
[I'-5]

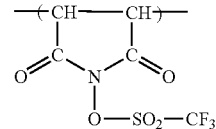
[I'-6]

-continued

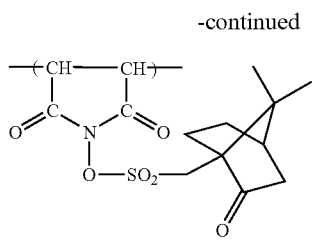

[I'-7]

The alicyclic hydrocarbon-base acid-decomposable resin of the present invention can contain various repeating structural units other than the above-mentioned repeating structural units in order to adjust the dry etching resistance and the applicability of standard developing solution, substrate adherence property, resist profile, and further, general properties such as resolution, heat resistance and sensitivity which are necessary for the resist, etc.

As the repeating structural units, repeating structural units corresponding to the following monomers can be mentioned, but they are not limited to these.

It becomes possible thereby to finely adjust properties which are required for the alicyclic hydrocarbon-base acid-decomposable resin, in particular,
(1) the solubility in a coating solvent,
(2) the film forming property (glass transition temperature),
(3) the alkali developing property,
(4) the film reduction (hydrophilic and hydrophobic properties, the selection of an alkali soluble group),
(5) the adherence property to the substrate of an unexposed portion, and
(6) the dry etching resistance.

As the monomer, for example, there can be mentioned compounds having one addition polymerizable unsaturated bond such as acrylic acid esters, methacrylic acid esters, acrylamides, methacrylamides, allyl compounds, vinyl ethers and vinyl esters, and the like.

The copolymerization component is preferably repeating units having alkali soluble groups, and more preferably repeating units having carboxylic groups. Containing these groups permits resolution to be increased in use for contact holes. Preferable repeating units having the carboxyl groups are either repeating units in which the carboxylic group is directly bonded to the main chain of the resin such as acrylic acid or methacrylic acid repeating units, or repeating units in which the carboxyl groups are bonded to the main chain of the resin with interposition of linker groups. The linker group may have a monocyclic or polycyclic hydrocarbon structure. The repeating unit is most preferably acrylic acid or methacrylic acid.

Additionally, an addition polmerizable unsaturated compound which can be copolymerized with a monomer corresponding to the above-mentioned various repeating structural units may be copolymerized.

In the alicyclic hydrocarbon-base acid-decomposable resin, the content molar ratio of the respective repeating structural units is appropriately set in order to adjust the dry etching resistance and the applicability of standard developing solution, substrate adherence property, resist profile, and further, general properties such as resolution, heat resistance and sensitivity which are necessary for the resist, etc.

As the preferable modes of the alicyclic hydrocarbon-base acid-decomposable resin of the present invention, those described below are mentioned:

(1) those containing the repeating structural unit having a partial structure which contains the alicyclic hydrocarbon represented by the above-mentioned general formulae (pI) to (pVI) (a side chain type),
(2) those containing the repeating structural unit represented by the general formula (II-AB) (a main chain type), however the following is, for example, further mentioned in (2),
(3) those having the repeating structural unit represented by the general formula (II-AB), a maleic anhydride and a methacrylate structure (a hybrid type).

In the alicyclic hydrocarbon-base acid-decomposable resin, the content molar ratio of the respective repeating structural units having a partial structure which contains the alicyclic hydrocarbon represented by the general formulae (pI) to (pVI) is preferably 30 to 70 mol % in the total repeating structural units, more preferably 35 to 65 mol % and further preferably 40 to 60 mol %.

In the alicyclic hydrocarbon-base acid-decomposable resin, the content of the repeating structural unit represented by the general formula (II-AB) is preferably 10 to 60 mol % in the total repeating structural units, more preferably 15 to 55mol % and further preferably 20 to 50 mol %.

Further, the content in a resin having the repeating structural unit based on the monomer of the above-mentioned further copolymerization component can be also appropriately set in accordance with the properties of a desired resist. However, the content is preferably 99 mol % or less usually based on the total moles of the repeating structural unit having a partial structure which contains the alicyclic hydrocarbon represented by the above-mentioned general formulae (pI) to (pVI) and the repeating structural unit represented by the general formula (II-AB), more preferably 90 mol % or less and further preferably 80 mol % or less.

When the composition of the present invention is used for ArF exposure, it is preferable that the resin has not an aromatic group from the viewpoint of transparency to ArF laser.

The alicyclic hydrocarbon-base acid-decomposable resin of the present invention can be synthesized according to a conventional method (for example, a radical polymerization). For example, as a usual synthetic method, monomers are charged in a reaction vessel, integrally or on the way to reaction, the mixture is dissolved in a reaction solvent, if necessary, for example, solvents which dissolves the composition of the present invention such as ethers such as tetrahydrofuran, 1,4-dioxane and diisopropyl ether; ketones such as methyl ethyl ketone and methyl isobutyl ketone; ester solvents such as ethyl acetate; and further, propyleneglycol monomethyl ether acetate described later, to be homogeneous. Then, the mixture is heated under inactive atmosphere such as nitrogen, argon and the like, it necessary, to initiate polymerization using a commercially available radical initiator (an azo initiator, a peroxide and the like). An initiator is added if necessary, or added in division, and the mixture is charged in a solvent after termination of the reaction and a desired polymer is recovered by methods such as powder or a solid recovery. The concentration of the reaction is 20% by weight or more, preferably 30% by weight or more and further preferably 40% by weight or more. The reaction temperature is 10° C. to 150° C., preferably 30° C. to 120° C. and further preferably 50° C. to 100° C.

When ArF eximer laser light is irradiated to the alicyclic hydrocarbon-base acid-decomposable resin of the present invention, the resin of the component (B) has a structure in which a fluorine atom was substituted at the main chain and/or side chin of a polymer skeleton, and is preferably a resin which is decomposed by the action of an acid and increases solubility in an alkali developing solution (hereinafter, referred to as the fluorine containing resin). There is more preferable a fluorine containing resin having at the main chain of a polymer skeleton at least one of sites selected from a perfluoroalkylene group and a perfluoroarylene group, or having at the side chain of a polymer skeleton at least one of sites which are selected from a perfluoroalkyl group, a perfluoroaryl group, a hexafluoro-2-propanol group and a group of protecting an OH group of a hexafluoro-2-propanol group.

As the fluorine containing resin in the acid decomposing resin, for example, a resin having at least one of the repeating units represented by the under-mentioned general formulae (IR) to (Xr) can be preferably mentioned.

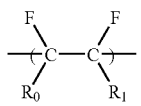
(IR)

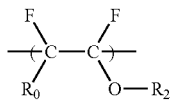
(IIR)

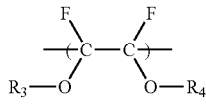
(IIIR)

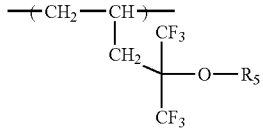
(IVR)

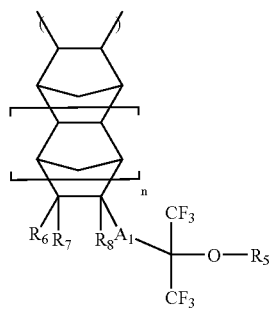
(VR)

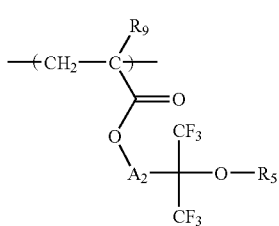
(VIR)

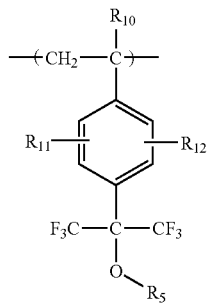
(VIIR)

(VIIIR)

(IXR)

(XR)

In the general formulae, $R_0$ and $R_1$ represent a hydrogen atom, a fluorine atom, an alkyl group, a perfluoroalkyl group, a cycloalkyl group or an aryl group which may optionally have a substituent.

$R_2$ to $R_4$ represent an alkyl group, a perfluoroalkyl group, a cycloalkyl group or an aryl group which may optionally have a substituent. Further, $R_0$ and $R_1$, $R_0$ and $R_2$, and $R_3$ and $R_4$ may be bonded to each other to form a ring.

$R_5$ represents a hydrogen atom, an alkyl group, a perfluoroalkyl group, a monocyclic or polycyclic cycloalkyl group, an acyl group and an alkoxycarbonyl group which may optionally have a substituent.

$R_6$, $R_7$ and $R_8$ may be the same or different, and represent a hydrogen atom, a halogen atom, an alkyl group, a perfluoroalkyl group, and an alkoxy group which may optionally have a substituent.

$R_9$ and $R_{10}$ maybe the same or different, and represent a hydrogen atom, a halogen atom, a cyano group, an alkyl group or a haloalkyl group which may optionally have a substituent.

$R_{11}$ and $R_{12}$ may be the same or different, and represent a hydrogen atom, a hydroxy group, a halogen atom, a cyano group, an alkoxy group, an acyl group, or an alkyl group, a cycloalkyl group, an alkenyl group, an aralkyl group or an aryl group which may optionally have a substituent.

$R_{13}$ and $R_{14}$ may be the same or different, and represent a hydrogen atom, a halogen atom, a cyano group, an alkyl group or a haloalkyl group which may optionally have a substituent.

$R_{15}$ represents an alkyl group which has a fluorine atom, a monocyclic or polycyclic cycloalkyl group which has a fluorine atom, an alkenyl group which has a fluorine atom, an aralkyl group which has a fluorine atom, or an aryl group which has a fluorine atom.

$R_{16}$, $R_{17}$ and $R_{18}$ may be the same or different, and represent a hydrogen atom, a halogen atom, a cyano group, an alkyl group, a perfluoroalkyl group, an alkoxy group and —CO—O—$R_{15}$ which may optionally have a substituent.

$R_{19}$, $R_{20}$ and $R_{21}$ may be the same or different, and represent a hydrogen atom, a fluorine atom, an alkyl group, a monocyclic or polycyclic cycloalkyl group, an alkenyl group, an aralkyl group or an aryl group which has a fluorine atom, provided that at least one of $R_{19}$, $R_{20}$ and $R_{21}$ is a group other than a hydrogen atom.

$A_1$ and $A_2$ may have a single bond, a divalent alkylene group, alkenylene group, cycloalkylene group or arylene group which may optionally have a substituent, or —O—CO—$R_{22}$—, —CO—O—$R_{23}$—, —CO—N($R_{24}$)—$R_{25}$—.

$R_{22}$, $R_{23}$ and $R_{25}$ may be the same or different, and represent an alkylene group, alkenylene group, cycloalkylene group or arylene group which may optionally have a single bond or an ether group, an ester group, an amide group, a urethane group or a urea group.

$R_{24}$ represent a hydrogen atom, an alkyl group, a cycloalkyl group, an aralkyl group or an aryl group in which these groups may optionally have a substituent. n represents 0 or 1, and x, y and z represent an integer of 0 to 4.

As the fluorine group containing resin for example, a resin having at least one of the repeating units represented by the under-mentioned general formulae (FA) to (FF) can be preferably mentioned.

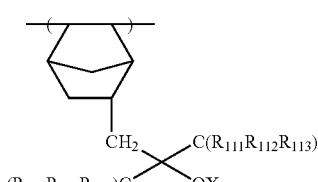

(FA)

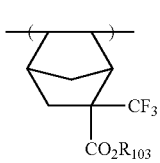

(FB)

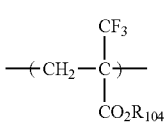

(FC)

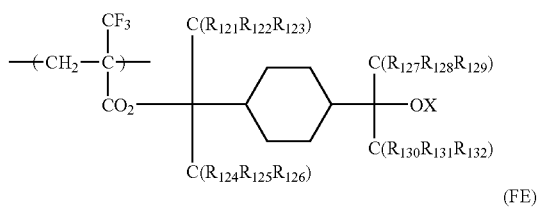

(FD)

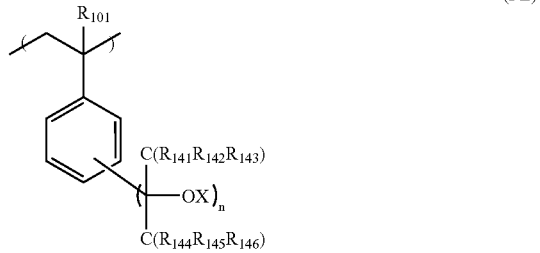

(FE)

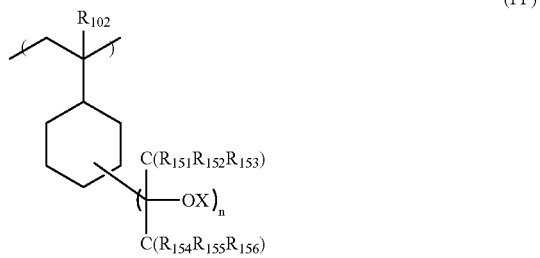

(FF)

$R_{101}$ and $R_{102}$ represent a hydrogen atom, a fluorine atom, a chlorine atom, a bromine atom, a cyano group, and a trifluoromethyl group.

X represents a hydrogen atom or a group which is decomposed by the action of an acid.

$R_{103}$ and $R_{104}$ represent a hydrogen atom, an alkyl group, an aryl group and an aralkyl group, which may optionally have a substituent, and said alkyl group and said aralkyl group may respectively have —O—, —O—, —CO$_2$—, —SO$_2$— and —SO—.

n represents an integer of 1 to 5.

Each of $R_{111}$ to $R_{116}$, $R_{121}$ to $R_{132}$, $R_{141}$ to $R_{148}$ and $R_{151}$ to $R_{158}$ respectively represent a hydrogen atom, a fluorine atom, and an alkyl group which may optionally have a substituent, but at least one is a fluorine atom.

As the group (hereinafter, referred to as an acid-decomposable group) which is decomposed by the action of an acid of X, for example, there are mentioned —C($R_{36}$)($R_{37}$)($R_{38}$), —C($R_{36}$)($R_{37}$)(OR$_{39}$), —COO—C($R_{36}$)($R_{37}$)($R_{38}$), —C($R_{01}$)($R_{02}$)($R_{39}$) —C($R_{01}$)($R_{02}$)COO—C($R_{36}$)($R_{37}$)($R_{38}$), and the like.

Each of $R_{36}$ to $R_{39}$ independently represents an alkyl group which may optionally have a substituent, a cycloalkyl group which may optionally have a substituent, an alkenyl group which may optionally have a substituent, an aralkyl group which may optionally have a substituent, or an aryl group which may optionally have a substituent. $R_{36}$ and $R_{39}$ may be bonded to each other to form a ring.

Each of $R_{01}$ and $R_{02}$ independently represents an alkyl group which may optionally have a substituent, a cycloalkyl group which may optionally have a substituent, an alkenyl group which may optionally have a substituent, an aralkyl group which may optionally have a substituent, or an aryl group which may optionally have a substituent.

As the specific examples of the preferable acid-decomposable group, there are preferably mentioned tert-alkyl groups such as a tert-butyl group, a tert-amyl group, a 1-alkyl-1-cyclohexyl group, a 2-alkyl-2-adamantyl group and a 2-adamantyl-2-propyl group; acetal groups such as a 1-alkoxy-1-ethoxy group, a 1-alkoxy-1-methoxy group and a tetrahydropyranyl group; a tert-alkylcarbonyl group, a tert-alkylcarbonylmethyl group, and the like.

The resin (B) in the present invention is preferably a fluorine group containing resin having the preferable acid-decomposable group which has at least one of the repeating units represented by the under-mentioned general formulae (XIR) to (XIIIR).

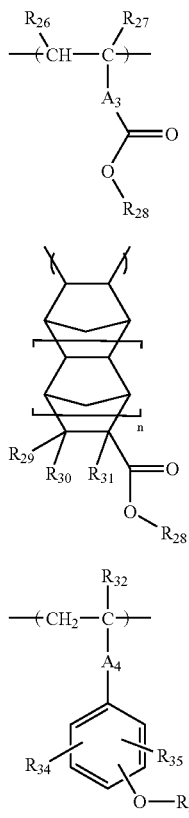

(XIR)

(XIIR)

(XIIIR)

In the formulae, $R_{26}$, $R_{27}$ and $R_{32}$ may be the same or different and represent a hydrogen atom, a halogen atom, a cyano group, an alkyl group or a haloalkyl group which may optionally have a substituent.

$R_{28}$ and $R_{33}$ represent —$C(R_{36})(R_{37})(R_{38})$, —$C(R_{36})(R_{37})$(O$R_{39}$), or the group of the under-mentioned general formula (XIVR).

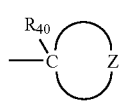

(XIVR)

$R_{29}$, $R_{30}$ and $R_{31}$ may be the same or different and represent a hydrogen atom, a halogen atom, a cyano group, an alkyl group, perfluoroalkyl group or alkoxy group which may optionally have a substituent, and —CO—O—$R_{28}$.

$R_{34}$ and $R_{35}$ may be the same or different and represent a hydrogen atom, a hydroxyl group, a halogen atom, a cyano group, an alkoxy group, an acyl group or an alkyl group, cycloalkyl group, alkenyl group, aralkyl group or aryl group which may optionally have a substituent.

$R_{36}$, $R_{37}$, $R_{38}$ and $R_{39}$ may be the same or different and represent an alkyl group, cycloalkyl group, alkenyl group, alkynyl group, aralkyl group or aryl group which may optionally have a substituent. Two of $R_{36}$, $R_{37}$ and $R_{38}$, or two of $R_{36}$, $R_{37}$ and $R_{39}$ may be bonded to form a ring. Further, the ring formed may contain an oxo group.

$R_{40}$ represents an alkyl group, cycloalkyl group, alkenyl group, alkynyl group, aralkyl group or aryl group, which may optionally have a substituent.

$A_3$ to $A_4$ represent a single bond, a divalent alkylene group, alkenylene group, cycloalkylene group or arylene group, which may optionally have a substituent, or —O—CO—$R_{22}$—, —CO—O—$R_{23}$—, —CO—N($R_{24}$)—$R_{25}$—.

$R_{22}$ to $R_{25}$ have the same definition as described above. Z represents an atomic group constituting a monocyclic or polycyclic alicyclic group together with a carbon atom. n represents 0 or 1.

Further, the present invention has at least one of the repeating unit derived from a vinyl compound which contains maleic anhydride, vinyl ether or a cyano group which is shown by the under-mentioned general formulae (XVR) to (XVIIR) in order to control physical properties such as the hydrophobic property of the fluorine group containing resin, glass transition point, and transmission coefficient against exposure light, or in order to control the polymerizability at synthesis of a polymer

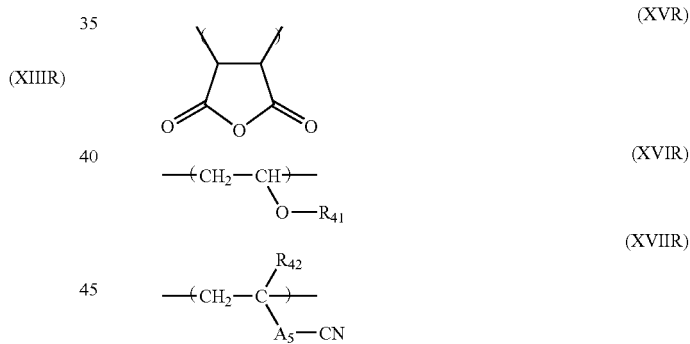

(XVR)

(XVIR)

(XVIIR)

In the formulae, $R_{41}$ represent an alkyl group, cycloalkyl group, aralkyl group or aryl group, which may optionally have a substituent.

$R_{42}$ represent a hydrogen atom, a halogen atom, a cyano group, an alkyl group or haloalkyl group, which may optionally have a substituent.

$A_5$ represents a single bond, a divalent alkylene group, alkenylene group, cycloalkylene group or arylene group, which may optionally have a substituent, or —O—CO—$R_{22}$—, —CO—O—$R_{23}$—, —CO—N($R_{24}$)—$R_{25}$—. $R_{22}$ to $R_{25}$ have the same meaning as described above.

Further, as the preferable fluorine group containing resin in the present invention, there can be mentioned a resin respectively having at least one of the repeating units represented by the under-mentioned general formulae (IA) to (IIA), and a resin respectively having at least one of the repeating units represented by the under-mentioned general formulae (IIA) to (VIA)

The resin respectively having at least one of the repeating units represented by the under-mentioned general formulae (IA) to (IIA), and the resin respectively having at least one of the repeating units represented by the under-mentioned general formulae (IIA) to (VIA) may further have the repeating units represented by the under-mentioned general formulae (IR) to (VR).

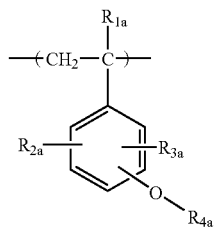

(IA)

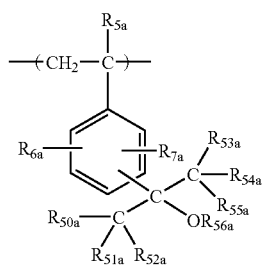

(IIA)

In the formulae (IA) and (IIA), $R_{1a}$ and $R_{5a}$ may be the same or different and represent a hydrogen atom, a halogen atom, a cyano group, and an alkyl group which may optionally have a substituent.

$R_{2a}$, $R_{3a}$, $R_{6a}$ and $R_{7a}$ may be the same or different, and represent a hydrogen atom, a halogen atom, a cyano group, a hydroxyl group, or an alkyl group, cycloalkyl group, alkoxy group, acyl group, acyloxy group, alkenyl group, aryl group or aralkyl group which may optionally have a substituent.

$R_{50a}$ to $R_{55a}$ may be the same or different, and represent a hydrogen atom, a fluorine atom, or an alkyl group which may optionally have a substituent. However, at least one among $R_{50a}$ to $R_{55a}$ represent a fluorine atom, or an alkyl group in which at least one of hydrogen atoms was substituted with a fluorine atom.

$R_{56a}$ represents a hydrogen atom, or an alkyl group, cycloalkyl group, acyl group or alkoxycarbonyl group, which may optionally have a substituent, and is preferably a hydrogen atom.

$R_{4a}$ represents a group of the under-mentioned general formula (IVA) or (VA).

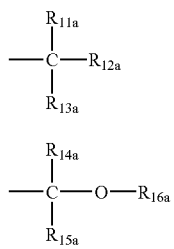

(IVA)

(VA)

In the formula (IVA), $R_{11a}$, $R_{12a}$ and $R_{13a}$ may be the same or different, and represent an alkyl group, cycloalkyl group, alkenyl group, aralkyl group or aryl group, which may optionally have a substituent.

In the formula (VA), $R_{14a}$ and $R_{15a}$ may be the same or different, and represent a hydrogen atom, or an alkyl group which may optionally have a substituent. $R_{16a}$ represents an alkyl group, cycloalkyl group, aralkyl group or aryl group, which may optionally have a substituent. Two of $R_{14a}$ to $R_{16a}$ may be bonded to form a ring.

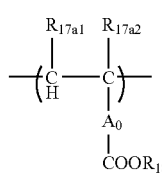

(VIA)

In the formula (VIA), $R_{17a1}$ and $R_{17a2}$ may be the same or different, and represent a hydrogen atom, a halogen atom, a cyano group, or an alkyl group which may optionally have a substituent. $R_{18a2}$ represents —C($R_{18a1}$)($R_{18a2}$)($R_{18a3}$), or —C($R_{18a1}$)($R_{18a2}$)(O$R_{18a4}$). $R_{18a1}$ to $R_{18a4}$ may be the same or different, and represent a hydrogen atom, or an alkyl group, cycloalkyl group, alkenyl group, aralkyl group or aryl group, which may optionally have a substituent. Two of $R_{18a1}$, $R_{18a2}$ and $R_{18a3}$ or two of $R_{18a1}$, $R_{18a2}$ and $R_{18a4}$ may be boded to form a ring. $A_0$ represents a single bond, a divalent linking group which may optionally have a substituent, but is preferably a single bond.

With respect to these fluorine group containing resins, it is preferable that $R_{18a}$ in the general formula (VIA) is a group represented by the under-mentioned general formula (VIA-A) or general formula (VIA-B). Further, with respect to these fluorine group containing resins (B), it is preferable that at least one of $R_{1a}$ in the general formula (IA), $R_{5a}$ in the general formula (IIA) and $R_{17a2}$ in the general formula (VIA) is a trifluoromethyl group.

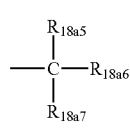

(VIA-A)

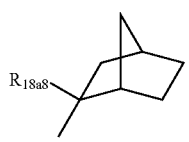

(VIA-B)

In the formula (VIA-A), $R_{18a5}$ and $R_{18a6}$ may be the same or different, and represent an alkyl group which may optionally have a substituent. $R_{18a7}$ represents a cycloalkyl group which may optionally have a substituent.

In the formula (VIA-B), $R_{18a8}$ represents an alkyl group, alkenyl group, alkynyl group, aralkyl group or aryl group, which may optionally have a substituent.

Further, the resin respectively having at least one of the repeating units represented by the under-mentioned general formulae (IA) to (IIA), and the resin respectively having at least one of the repeating units represented by the under-mentioned general formulae (IIA) to (VIA) may further have at least one of the repeating units represented by the undermentioned general formula (IIIA) or (VIIA).

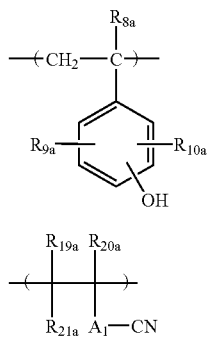

(IIIA)

(VIIA)

In the general formula (IIIA), $R_{8a}$ represents a hydrogen atom, a halogen atom, a cyano group, or an alkyl group which may optionally have a substituent. $R_{9a}$ and $R_{10}$ may be the same or different, and represent a hydrogen atom, a halogen atom, a cyano group, or an alkyl group, cycloalkyl group, alkoxy group, acyl group, acyloxy group, alkenyl group, aryl group, aralkyl group, which may optionally have a substituent.

In the general formula (VIIA), $R_{19a}$ and $R_{20a}$ may be the same or different, and represent a hydrogen atom, a halogen atom, a cyano group, or an alkyl group which may optionally have a substituent. $R_{21a}$ represents a hydrogen atom, a halogen atom, an alkyl group which may optionally have a substituent, or a —$A_1$—CN group. $A_0$ represents a single bond, a divalent linking group.

The above-mentioned alkyl group is for example, an alkyl group having 1 to 8 carbon atoms and specifically, there can be preferably mentioned a methyl group, an ethyl group, a propyl group, a n-butyl group, a sec-butyl group, a hexyl group, a 2-ethylhexyl group and an octyl group.

The cycloalkyl group may be a monocyclic type and a polycyclic type. The monocyclic type is a group having 3 to 8 carbon atoms, and for example, there can be preferably mentioned a cyclopropyl group, a cyclopentyl group, a cyclohexyl group, a cycloheptyl group and a cyclooctyl group. The polycyclic type is a group having 6 to 20 carbon atoms, and for example, there can be preferably mentioned an adamantyl group, a norbornyl group, an isoboronyl group, a camphornyl group, a dicyclopentyl group, a pinenyl group, a tricyclodecanyl group, a tetracyclododecyl group, an androstanyl group, and the like. However, carbon atoms in the above-mentioned monocyclic group and a polycyclic group may be-substituted with hetero atoms such as an oxygen atom.

As the specific perfluoroalkyl group, there can be preferably mentioned a perfluorobutyl group, a perfluorohexyl group, a perfluorooctyl group, a perfluorooctylethyl group, a perfluorododecyl group and the like.

The haloalkyl group is for example, a haloalkyl group having 1 to 4 carbon atoms, and specifically, there can be preferably mentioned a chloromethyl group, a chloroethyl group, a chloropropyl group, a chlorobutyl group, a bromomethyl group, a bromoethyl group and the like.

The aryl is for example, an aryl group having 6 to 15 carbon atoms, and specifically, there can be preferably mentioned a phenyl group, a tolyl group, a dimethylphenyl group, a 2,4,6-trimethylphenyl group, a naphthyl group, an anthryl group, a 9,10-dimethoxyanthryl group and the like.

The aralkyl group is, for example, an aralkyl group having 7 to 12 carbon atoms, and specifically, there can be preferably mentioned a benzyl group, a phenethyl group, a naphthylmethyl group and the like.

The alkenyl group is, for example, an alkenyl group having 2 to 8 carbon atoms, and specifically, there can be preferably mentioned a vinyl group, an allyl group, a butenyl group, a cyclohexenyl group, and the like.

The alkoxy group is, for example, an alkoxy group having 1 to 8 carbon atoms, and specifically, there can be preferably mentioned a methoxy group, an ethoxy group, an n-propoxy group, an isopropoxy group, a butoxy group, a pentoxy group, an allyloxy group, an octoxy group, and the like.

The acyl group is, for example, an acyl group having 1 to 10 carbon atoms, and specifically, there can be preferably mentioned a formyl group, an acetyl group, a propanoyl group, a butanoyl group, a pyvaroyl group, an octanoyl group, a benzoyl group, and the like.

The acyloxy group is, for example, an acyloxy group having 2 to 12 carbon atoms, and specifically, there can be preferably mentioned an acetoxy group, a propionyloxy group, a benzoyloxy group, and the like.

The alkynyl group is an alkynyl group having 2 to 5 carbon atoms, and, for example, there can be preferably mentioned an ethynyl group, a propynyl group, a butynyl group and the like.

As the alkoxycarbonyl group, there can be mentioned an isopropoxycarbonyl group, a tert-butoxycarbonyl group, an n-pentyloxy group carbonyl, an isopentyloxycarbonyl group, a tert-amyloxycarbonyl group, a 1-methyl-1-cyclohexylcarbonyl group, and the like, preferably a secondary alkoxycarbonyl group and more preferably a tert-alkoxycarbonyl group.

As the halogen atom, for example, a fluorine atom, a chlorine atom, a bromine atom, an iodine atom and the like are mentioned.

As the alkylene group, there are preferably mentioned alkylene groups having 1 to 8 carbon atoms which may optionally have a substituent such as a methylene group, an ethylene group, a propylene group, a butylene group, a hexylene group, an octylene group, and the like.

As the alkenylene group, there are preferably mentioned alkenylene groups having 2 to 6 carbon atoms which may optionally have a substituent such as an ethenylene group, a propenylene group, a butenylene group, and the like.

As the cycloalkylene group, there are preferably mentioned cycloalkylene groups having 5 to 8 carbon atoms which may optionally have a substituent such as an ethenylene group, a propenylene group, a butenylene group, and the like.

As the arylene group, there are preferably mentioned arylene groups having 6 to 15 carbon atoms which may optionally have a substituent such as a phenylene group, a tolylene group, a naphthylene group, and the like.

The divalent linking group represents a divalent alkylene group, cycloalkylene group, alkenylene group or arylene group, which may optionally have a substituent, or —O—CO—$R_{22a}$—, —CO—O—$R_{23}$—, —CO—N($R_{24a}$)—$R_{25a}$—, $R_{22a}$, $R_{23a}$ and $R_{25a}$ may be the same or different, and represent a single bond, a divalent alkylene group, alkenylene group, cycloalkylene group or arylene group, which may optionally have an ether group, an ester group, an amide group, a urethane group or a ureido group. $R_{24a}$ represents a hydrogen atom, or an alkyl group, cycloalkyl group and aralkyl group, which may optionally have a substituent.

A ring which is formed by bonding $R_0$ and $R_1$, or $R_0$ and $R_2$, or $R_3$ and $R_4$ is, for example, a 5 to 7 membered ring, and specifically, there are mentioned a pentane ring, a hexane ring, a furan ring, a dioxonol ring, a 1,3-dioxolane ring and the like.

A ring which is formed by bonding two of $R_{36}$ to $R_{38}$, or two of $R_{37}$ to $R_{37}$ and $R_{39}$ is, for example, a 3 to 8 membered ring, and specifically, there are mentioned a cyclopropane ring, a cyclopentane ring, a cyclohexane ring, a furan ring, a pyran ring and the like.

A ring which is formed by bonding two of $R_{14a}$ to $R_{16a}$, or two of $R_{18a1}$ to $R_{18a3}$ or two of $R_{18a1}$, $R_{18a2}$ and $R_{18a4}$ is preferably a 3 to 8 membered ring, and, for example, there can be mentioned a cyclopropane ring, a cyclopentane ring, a cyclohexane ring, a tetramethyleneoxide ring, a pentamethyleneoxide ring, a hexamethyleneoxide ring, a furan ring, a pyran ring, a dioxonol ring, a 1,3-dioxolane ring and the like.

Z represents an atom group constituting a monocyclic or polycyclic alicyclic group. The alicyclic group which was formed is an alicyclic group having 3 to 8 carbon atoms as a monocyclic group, and for example, there can be preferably mentioned a cyclopropyl group, a cyclopentyl group, a cyclohexyl group, a cycloheptyl group and a cyclooctyl group. The polycyclic type is a group having 6 to 20 carbon atoms, and for example, there can be preferably mentioned an adamantyl group, a norbornyl group, an isoboronyl group, a camphornyl group, a dicyclopentyl group, a pinenyl group, a tricyclodecanyl group, a tetracyclododecyl group, an androstanyl group, and the like.

Further, as the substituent which is substituted with these groups, there are mentioned those having an active hydrogen such as an alkyl group, a cycloalkyl group, an aryl group, an amino group, an amido group, an ureido group, an urethane group, a hydroxyl group and a carboxyl group; a halogen atom (a fluorine atom, a chlorine atom, a bromine atom and an iodine atom); an alkoxy group (a methoxy group, an ethoxy group, a propoxy group, a butoxy group and the like), a thio ether group, an acyl group (an acetyl group, a propanoyl group, a benzoyl group and the like), an acyloxy group (an acetoxy group, a propanoyloxy group, a benzoyloxy group, and the like), an alkoxycarbonyl group (a methoxycarbonyl group, an ethoxycarbonyl group, a propoxycarbonyl group, and the like), a cyano group, a nitro group and the like.

Hereat, a group shown by the above-mentioned description is mentioned as the alkyl group, cycloalkyl group and aryl group, but the alkyl group may be further substituted with a fluorine atom and a cycloalkyl group.

As the group contained in the fluorine group containing resin of the present invention which is decomposed by the action of an acid and exhibits alkali soluble property, for example, there are mentioned —C($R_{36}$)($R_{37}$)($R_{38}$), —C($R_{36}$)($R_{37}$)(O$R_{39}$), —O—COO—C($R_{36}$)($R_{37}$)($R_{38}$), —O—C($R_{01}$)($R_{02}$)—COO—C($R_{36}$)($R_{37}$)($R_{38}$), —COO—C($R_{36}$)($R_{37}$)($R_{38}$), —COO—C($R_{36}$)($R_{37}$)(O$R_{39}$), and the like.

$R_{36}$ to $R_{39}$ have the same meaning as mentioned above, and $R_{01}$ and $R_{02}$ represent a hydrogen atom, the above-mentioned alkyl group, cycloalkyl group, alkenyl group, an aralkyl group or aryl group, which may optionally have a substituent.

As the preferable specific examples, there are preferably mentioned the ether group or ester group of tert-alkyl groups such as a tert-butyl group, a tert-amyl group, a 1-alkyl-1-cyclohexyl group, a 2-alkyl-2-adamantyl group, a 2-adamantyl-2-propyl group and a 2-(4-methylcyclohexyl)-2-propyl group; acetal groups or acetal ester groups such as a 1-alkoxy-1-ethoxy group and a tetrahydropyranyl group; a tert-alkylcarbonyl group, a tert-alkylcarbonylmethoxy group, and the like.

The total of the content of the repeating structural units represented by the general formulae (IR) to (XR) is in general 10 to 80 mol % in the total polymer composition, preferably 30 to 70 mol % and further preferably 35 to 65 mol %.

The total of the content of the repeating structural units represented by the general formulae (XIR) to (XIIIR) is in general 0 to 70 mol % in the total polymer composition, preferably 10 to 60 mol % and further preferably 20 to 50 mol %.

The total of the content of the repeating structural units represented by the general formulae (XVR) to (XVIIIR) is in general 0 to 70 mol % in the total polymer composition, preferably 10 to 60 mol % and further preferably 20 to 50 mol %.

It is further preferable that the resin (B) of the present invention has at least one of the repeating structural units represented by the general formulae (IR) to (IIIR) and at least one of the repeating structural units represented by the general formulae (IVR) to (VIR).

Further, it is further preferable in like manner as the above description that the resin (B) of the present invention has at least one of the repeating structural units represented by the general formulae (IVR) to (VIR) and at least one of the repeating structural units represented by the general formulae (VIIIR) to (XR).

Further, it is further preferable in like manner as the above description that the resin (B) of the present invention has at least one of the repeating structural units represented by the general formulae (IVR) to (VIIR) and at least one of the repeating structural units represented by the general formulae (XVR) to (XVIIIR).

The transmitting property of 157 nm in a resin is adequately enhanced thereby, and the lowering of the dry etching resistance can be suppressed.

When the resin (B) of the present invention has at least one of the repeating structural units represented by the general formulae (IR) to (IIIR) and at least one of the repeating structural units represented by the general formulae (IVR) to (VIR), the total of the content of the repeating structural units represented by the general formulae (IR) to (IIIR) is in general 0 to 70 mol % in the total polymer composition, preferably 10 to 60 mol % and further preferably 20 to 50 mol %.

The total of the content of the repeating structural units represented by the general formulae (IVR) to (VIR) is in general 10 to 80 mol % in the total polymer composition, preferably 30 to 70 mol % and further preferably 35 to 65 mol %.

When the resin (B) of the present invention has at least one of the repeating structural units represented by the general formulae (IVR) to (VIR) and at least one of the repeating structural units represented by the general formulae (VIIIR) to (XR), the total of the content of the repeating structural units represented by the general formulae (IVR) to (VIR) is in general 10 to 80 mol % in the total polymer composition, preferably 30 to 70 mol % and further preferably 35 to 65 mol %.

The total of the content of the repeating structural units represented by the general formulae (VIIIR) to (XR) is in general 0 to 70 mol % in the total polymer composition, preferably 10 to 60 mol % and further preferably 20 to 50 mol %.

When the resin (B) of the present invention has at least one of the repeating structural units represented by the general formulae (IVR) to (VIIR) and at least one of the repeating structural units represented by the general formulae (XVR) to (XVIIIR), the total of the content of the repeating structural units represented by the general formulae (IVR) to (VIIR) is in general 10 to 80 mol % in the total polymer composition, preferably 30 to 70 mol % and further preferably 35 to 65 mol %.

The total of the content of the repeating structural units represented by the general formulae (XVR) to (XVIIR) is in general 0 to 70 mol % in the total polymer composition, preferably 10 to 60 mol % and further preferably 20 to 50 mol %.

In the fluorine group containing resin having at least one of the respective repeating structural units represented by the general formulae (IA) and (IIA), the content of the repeating structural unit represented by the general formula (IA) is in general 5 to 80 mol %, preferably 10 to 75 mol % and further preferably 20 to 70 mol %.

In the fluorine group containing resin having at least one of the respective repeating structural units represented by the general formulae (IA) and (IIA), the content of the repeating structural unit represented by the general formula (IIA) is in general 5 to 80 mol %, preferably 10 to 70 mol % and further preferably 20 to 65 mol %.

In the fluorine group containing resin having at least one of the respective repeating structural units represented by the general formulae (IIA) and (VIA), the content of the repeating structural unit represented by the general formula (IIA) is in general 5 to 80 mol %, preferably 10 to 70 mol % and further preferably 20 to 65 mol %.

In the fluorine group containing resin having at least one of the respective repeating structural units represented by the general formulae (IIA) and (VIA), the content of the repeating structural unit represented by the general formula (VIA) is in general 5 to 80 mol %, preferably 10 to 70 mol % and further preferably 20 to 65 mol %.

In these fluorine group containing resins, the content of the repeating structural unit represented by the general formula (IIIA) is in general 1 to 40 mol %, preferably 3 to 35 mol % and further preferably 5 to 30 mol %.

In these fluorine group containing resins, the content of the repeating structural unit represented by the general formula (VIIA) is in general 1 to 40 mol %, preferably 3 to 35 mol % and further preferably 5 to 30 mol %.

In the resin (B) of the present invention, other polymerizable monomer other than the above-mentioned repeating structural unit may be copolymerized for improving the properties of the positive type resist of the present invention.

As the copolymerization monomer which can be used, those shown below are included. For example, they are a compound having one addition polymerization-base unsaturated bond selected from acrylic acid esters, acrylamides, methacrylic acid esters, methacrylamides, allyl compounds, vinyl ethers, vinyl esters, crotonic acid ester and the like other than the above-mentioned compounds.

The specific examples of the repeating structural units represented by the general formulae (IR) to (XR) are shown below, but the present invention is not limited to this.

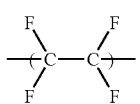
(F-1)

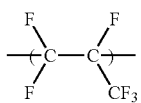
(F-2)

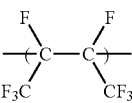
(F-3)

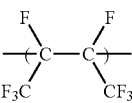
(F-4)

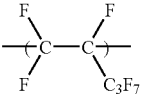
(F-5)

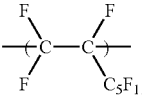
(F-6)

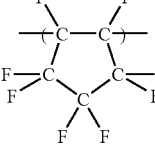
(F-7)

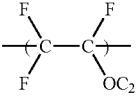
(F-8)

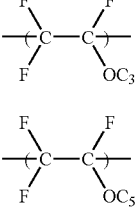
(F-9)

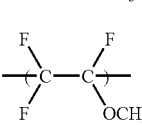
(F-10)

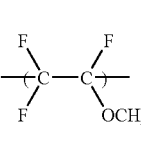
(F-11)

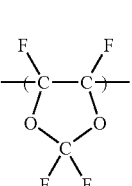
(F-12)

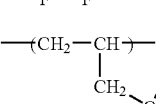
(F-13)

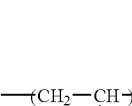
(F-14)

-continued
(F-15) 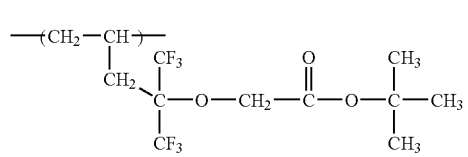
(F-16) 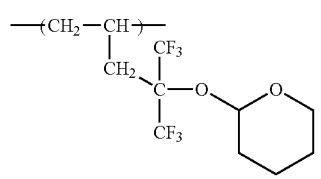
(F-17) 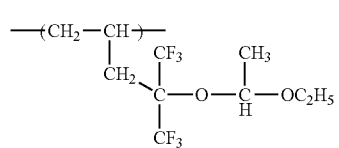
(F-18) 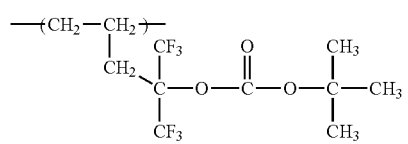
(F-19) 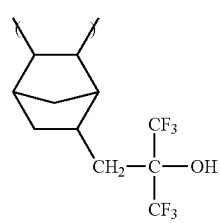
(F-20) 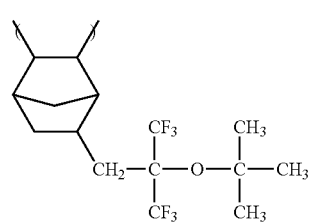
(F-21) 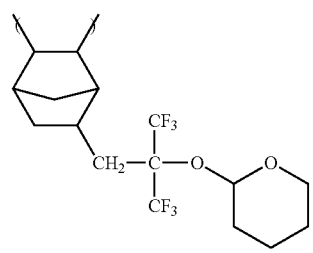
(F-22) 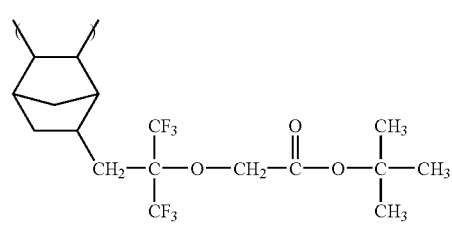
-continued
(F-23) 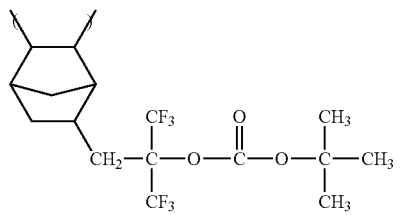
(F-24) 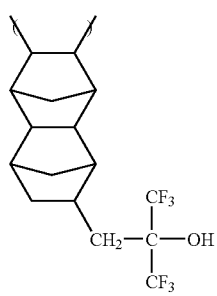
(F-25) 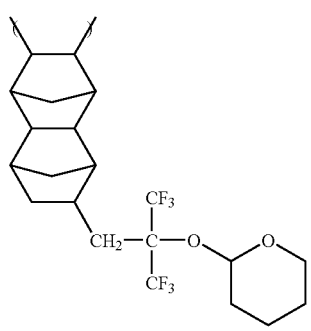
(F-26) 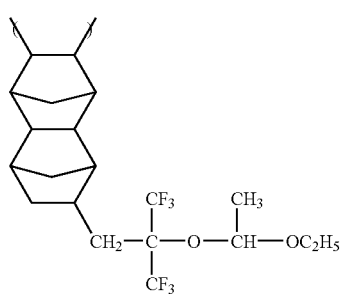
(F-27) 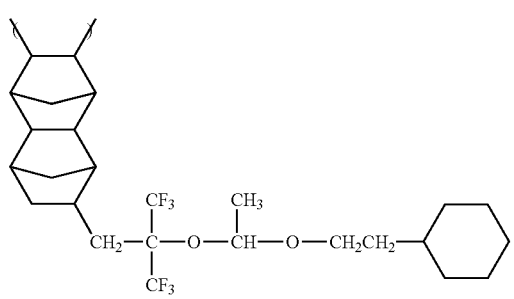

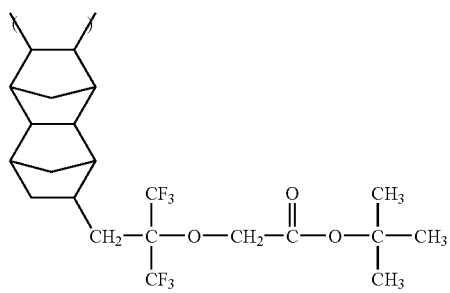
(F-28)
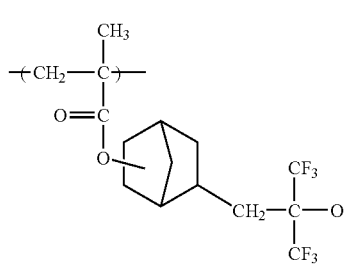
(F-29)
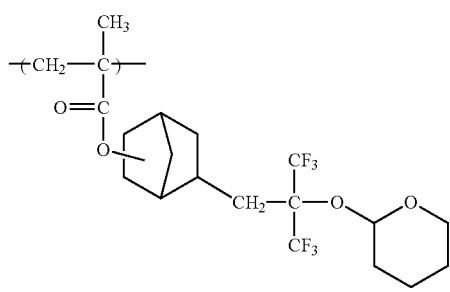
(F-30)
(F-31)
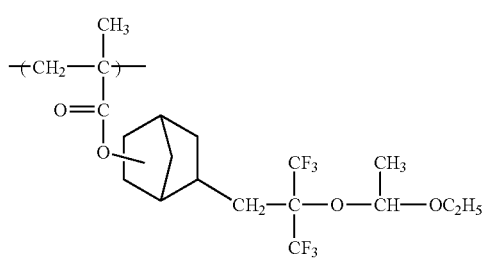
(F-32)
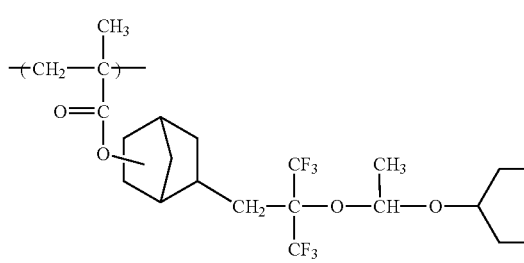
(F-33)
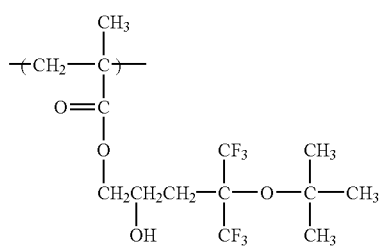
(F-34)
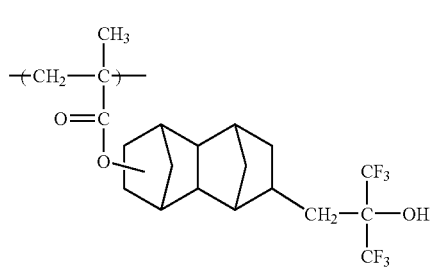
(F-35)
(F-36)
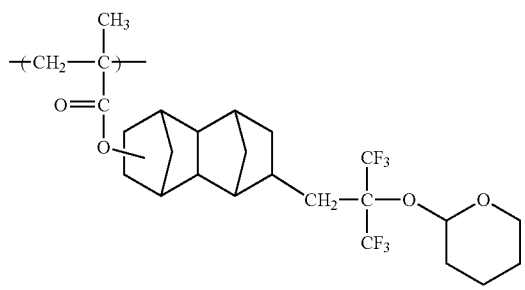
(F-37)
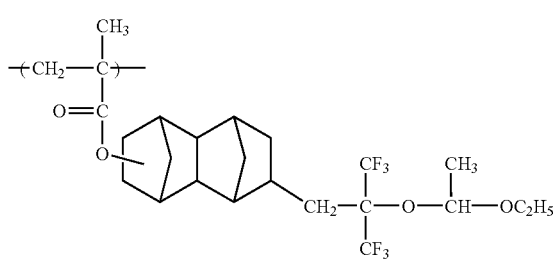

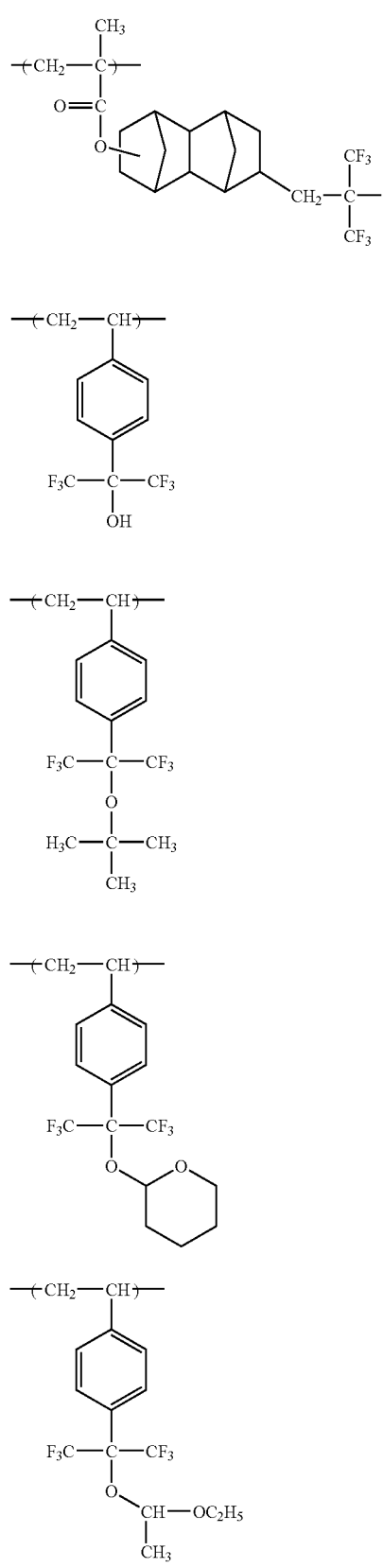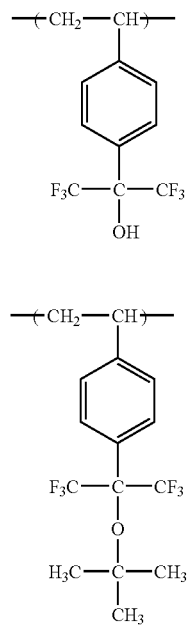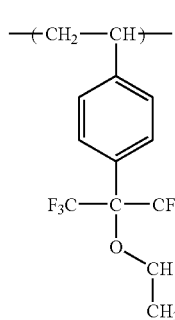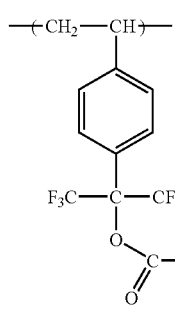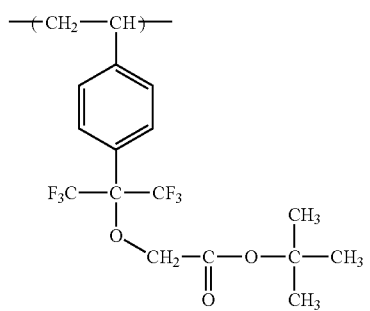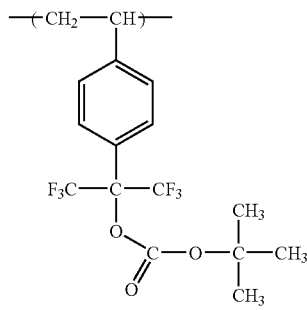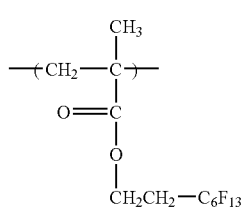

-continued
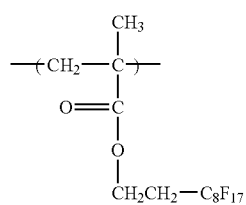 (F-48)
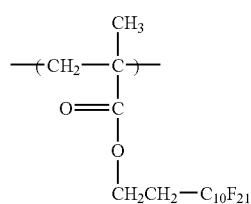 (F-49)
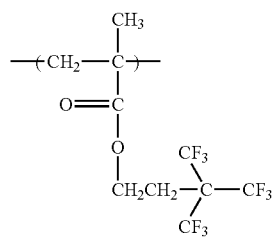 (F-50)
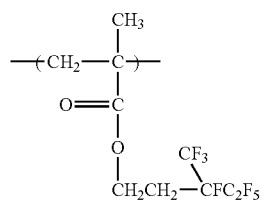 (F-51)
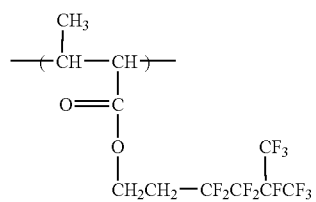 (F-52)
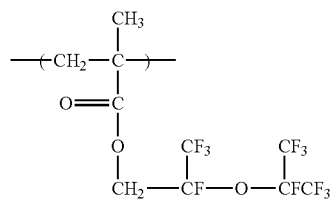 (F-53)
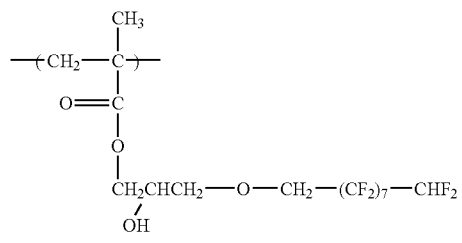 (F-54)
-continued
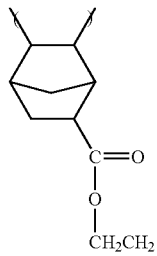 (F-55)
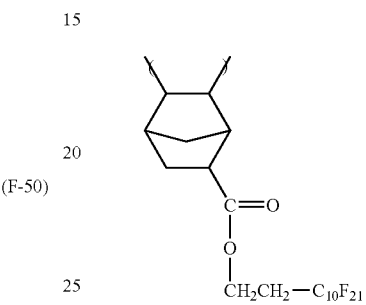 (F-56)
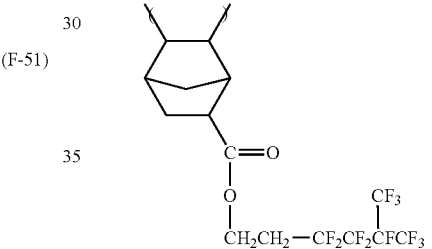 (F-57)
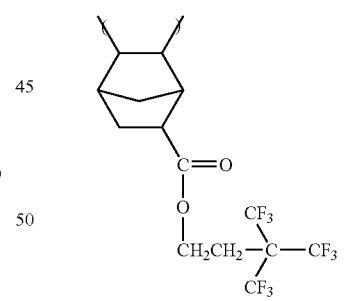 (F-58)
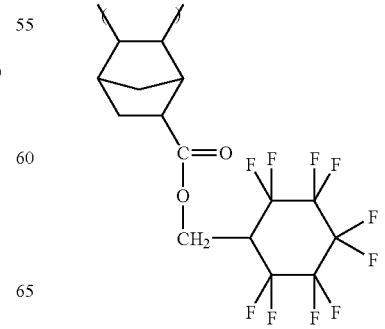 (F-59)

-continued
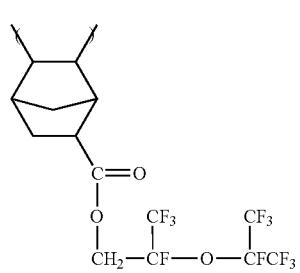
(F-60)
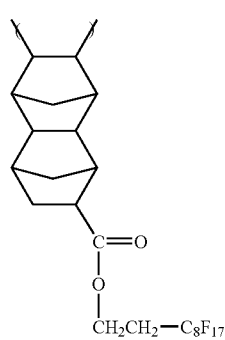
(F-61)
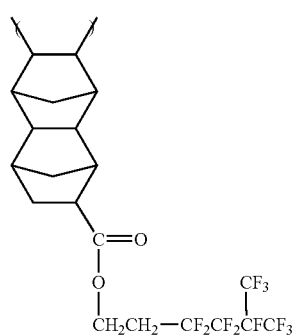
(F-62)
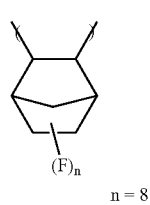
n = 8
(F-63)
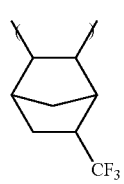
(F-64)
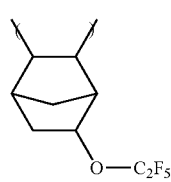
(F-65)
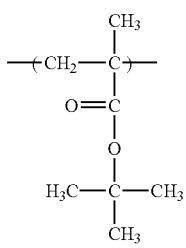
(B-1)
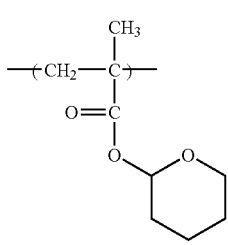
(B-2)
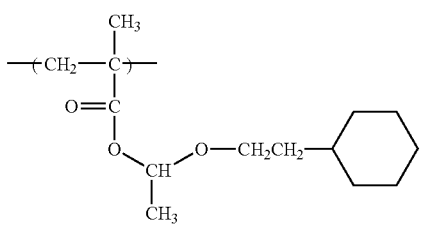
(B-3)
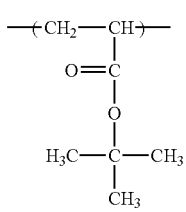
(B-4)
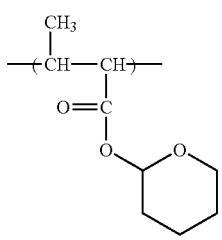
(B-5)
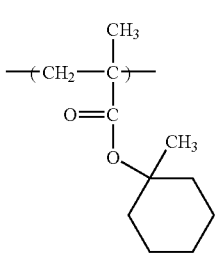
(B-6)
Further, the specific examples of the repeating structural units represented by the general formulae (XIR) to (XIIIR) are shown below, but the present invention is not limited to these.

-continued
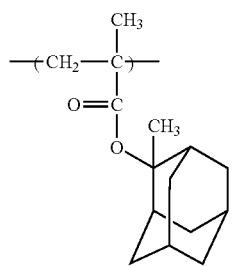
(B-7)
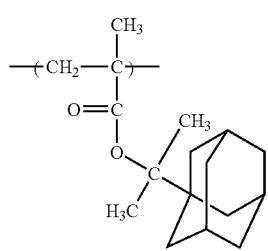
(B-8)
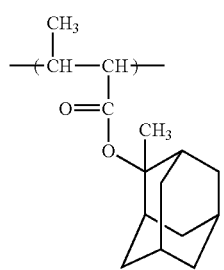
(B-9)
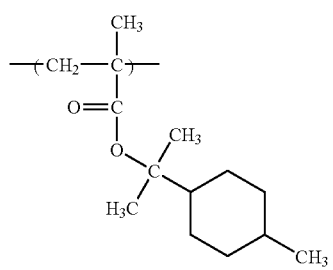
(B-10)
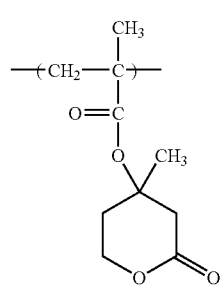
(B-11)
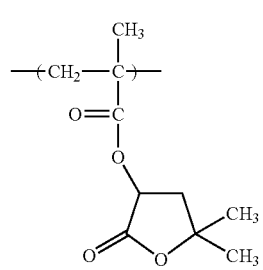
(B-12)
-continued
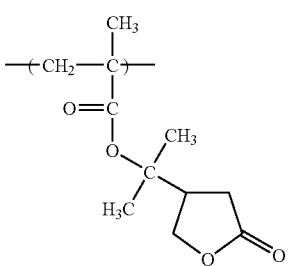
(B-13)
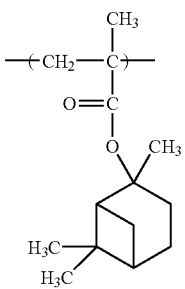
(B-14)
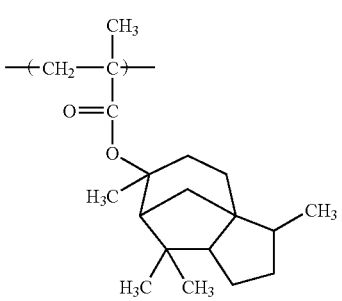
(B-15)
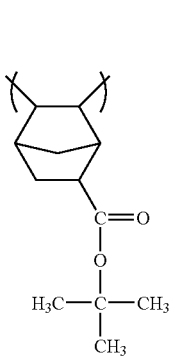
(B-16)
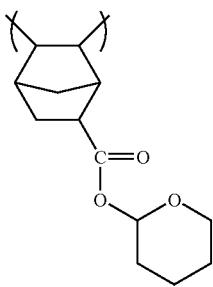
(B-17)

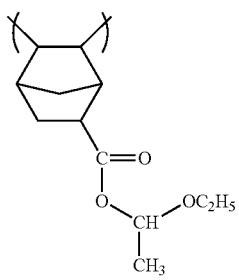
(B-18)
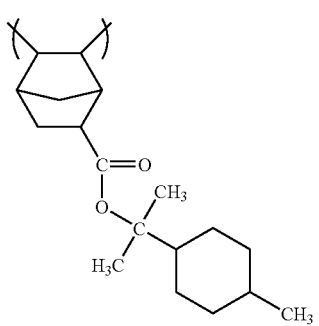
(B-19)
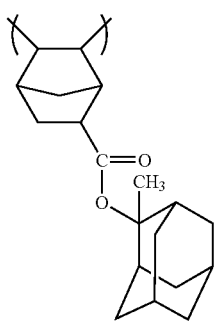
(B-20)
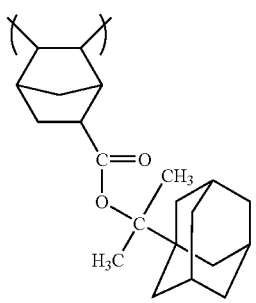
(B-21)
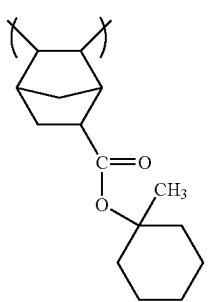
(B-22)
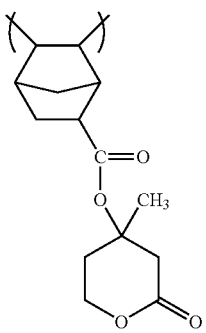
(B-23)
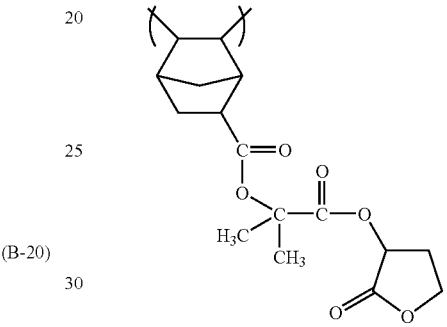
(B-24)
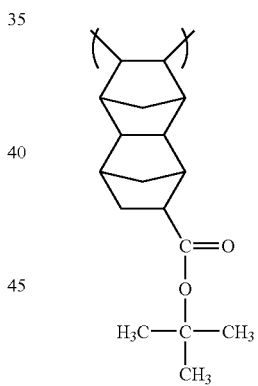
(B-25)
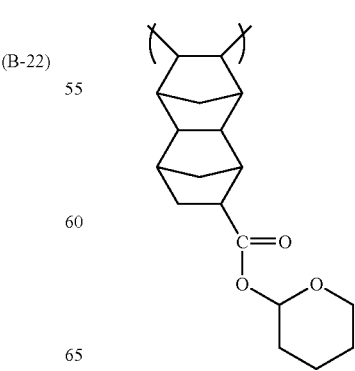
(B-26)

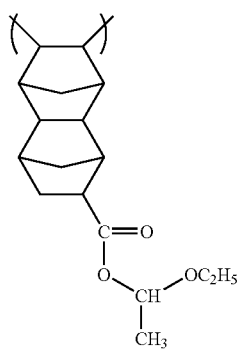 (B-27)
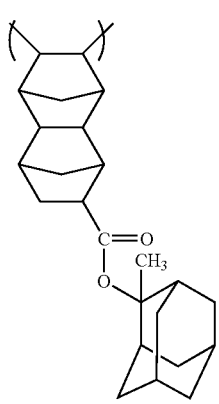 (B-28)
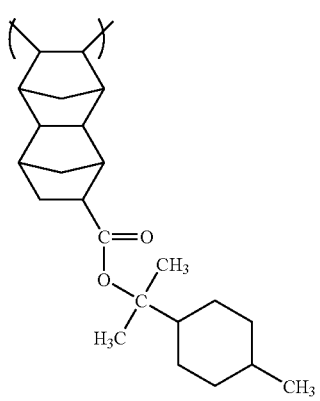 (B-29)
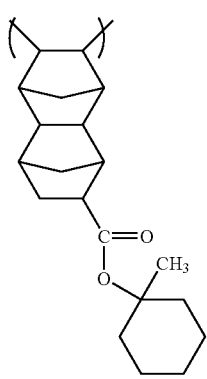 (B-30)
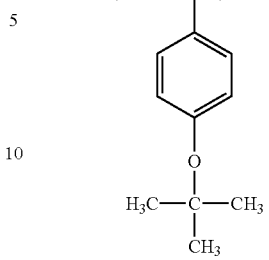 (B-31)
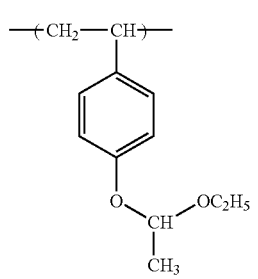 (B-32)
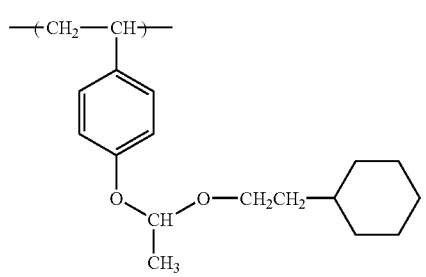 (B-33)
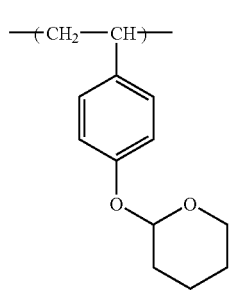 (B-34)
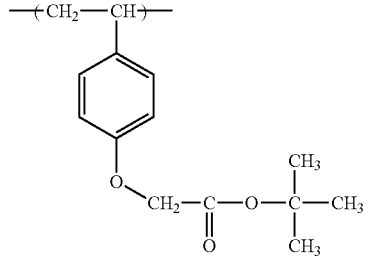 (B-35)

-continued (B-36)
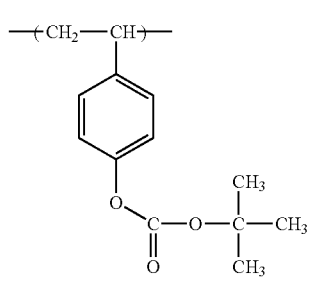

Further, the specific examples of the repeating structural units represented by the general formulae (XVIR) to (XVIIR) are shown below, but the present invention is not limited to these.

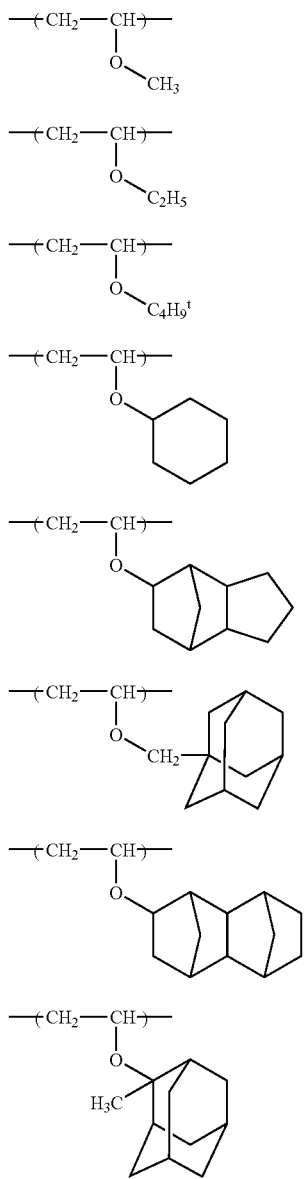

(C-1)
(C-2)
(C-3)
(C-4)
(C-5)
(C-6)
(C-7)
(C-8)

-continued

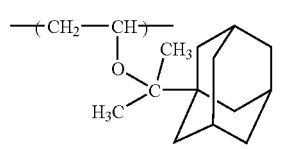 (C-9)

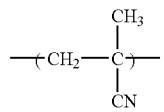 (C-10)

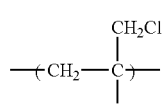 (C-11)

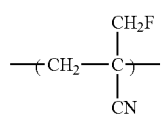 (C-12)

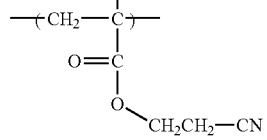 (C-13)

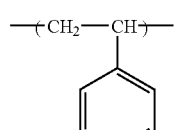 (C-14)

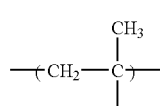 (C-15)

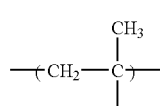

Further, the specific examples of the repeating structural unit represented by the general formula (IA) are shown below, but the present invention is not limited to these.

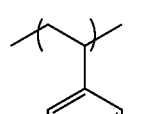 (A-1)

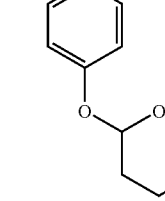

-continued
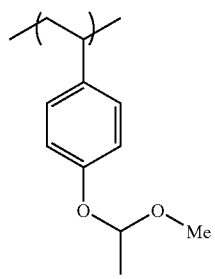
(A-2)
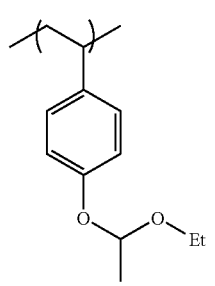
(A-3)
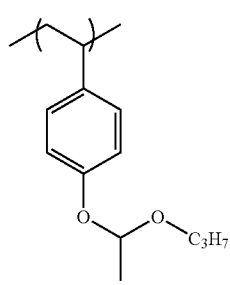
(A-4)
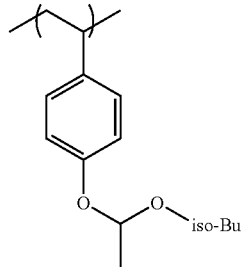
(A-5)
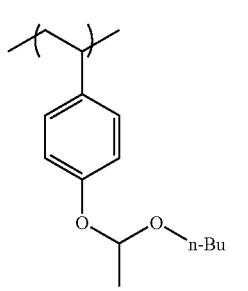
(A-6)
-continued
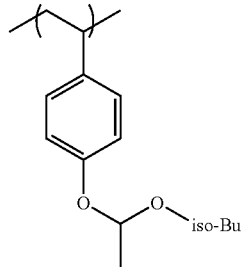
(A-7)
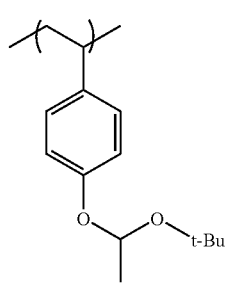
(A-8)
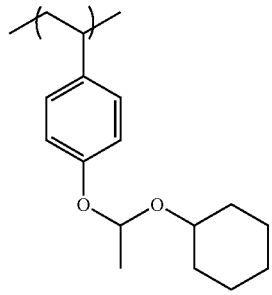
(A-9)
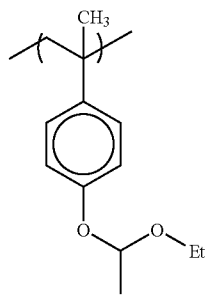
(A-3')
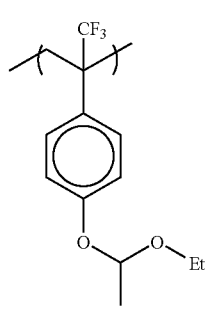
(A-3")

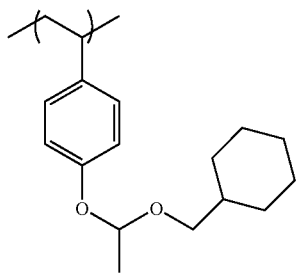 (A-10)
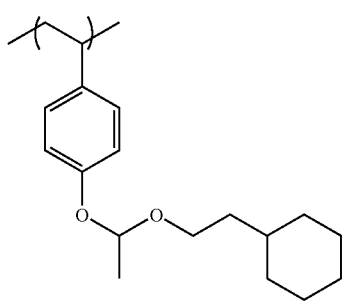 (A-11)
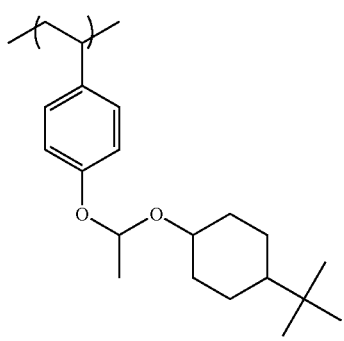 (A-12)
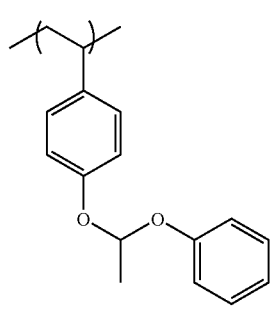 (A-13)
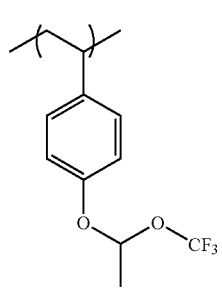 (A-14)
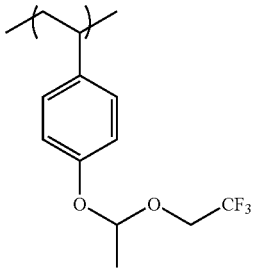 (A-15)
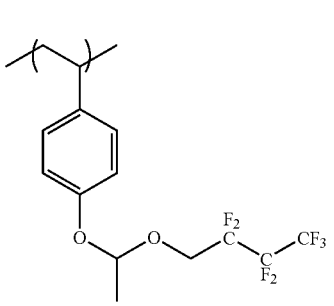 (A-16)
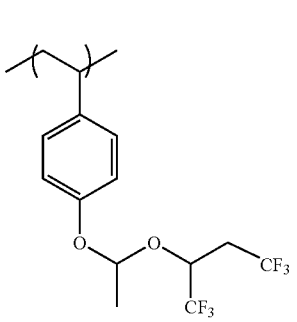 (A-17)
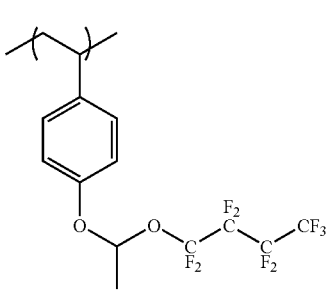 (A-18)
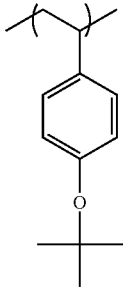 (A-19)

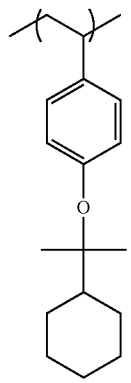 (A-20)
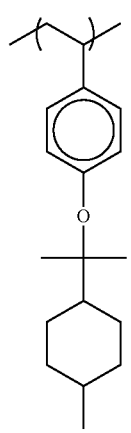 (A-20')
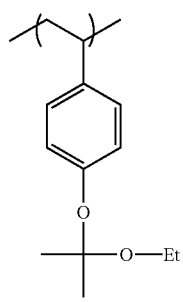 (A-24)
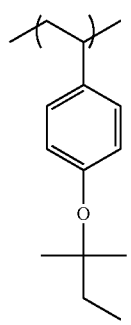 (A-25)
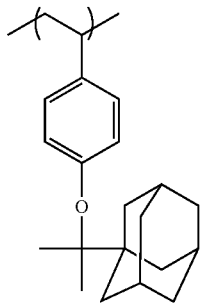 (A-26)
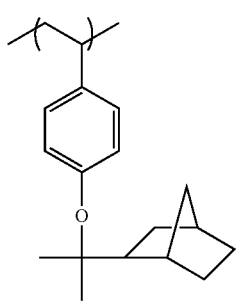 (A-27)
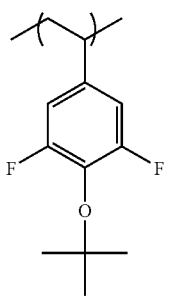 (A-28)
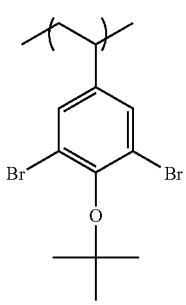 (A-29)
 (A-30)

(A-31) 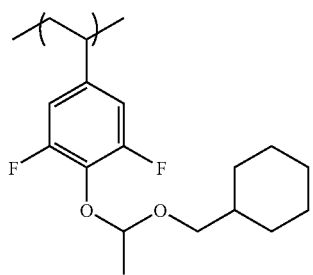
(A-32) 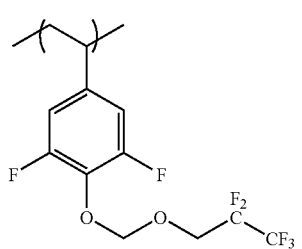
(A-33) 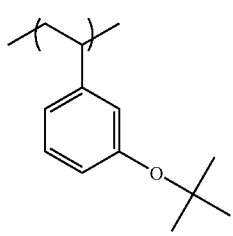
(A-34) 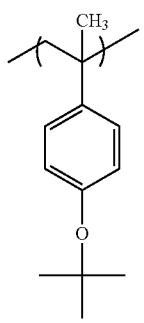
(A-35) 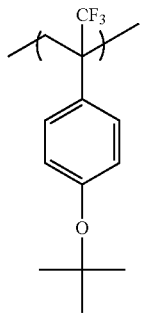
(A-36) 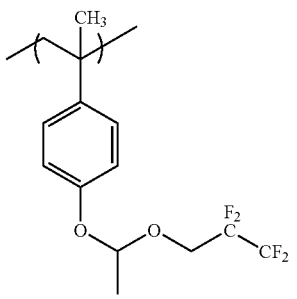
(A-37) 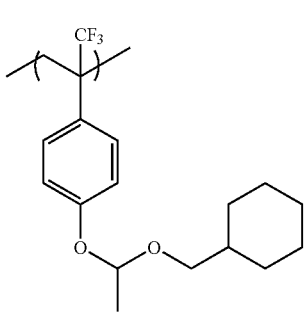
(A-38) 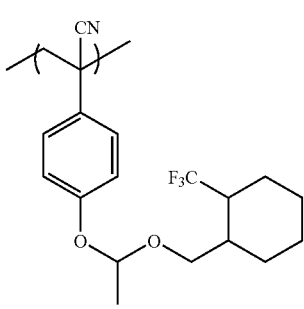
The specific examples of the repeating structural unit represented by the general formula (IIA) are shown below, but the present invention is not limited to these.
(IIa-1) 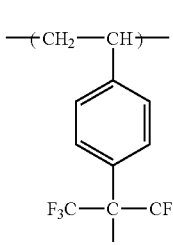
(IIa-2) 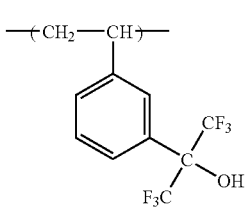

-continued (IIa-3) 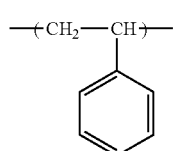

(IIa-4) 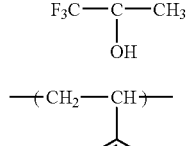

(IIa-5) 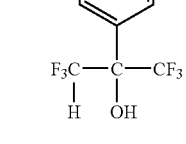

(IIa-6) 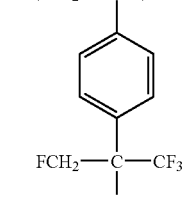

(IIa-7) 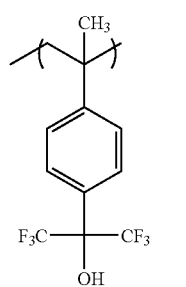

(IIa-8) 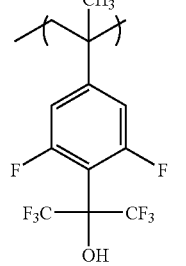

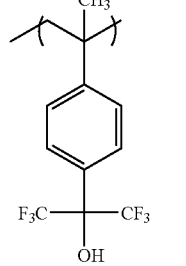

As the specific examples of the repeating unit represented by the general formula (IIA), the repeating units (F-40) to (F-45) which were previously exemplified can be mentioned.

The specific examples of the repeating structural unit represented by the general formula (VIA) are shown below, but the present invention is not limited to these.

(B-1) 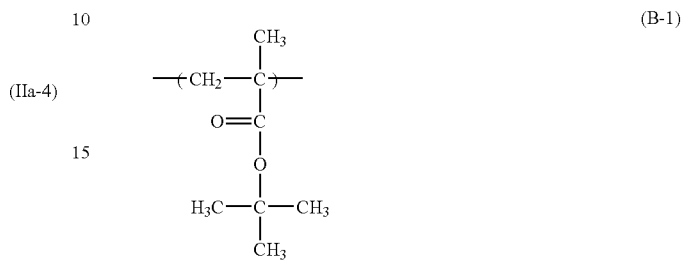

(B-2) 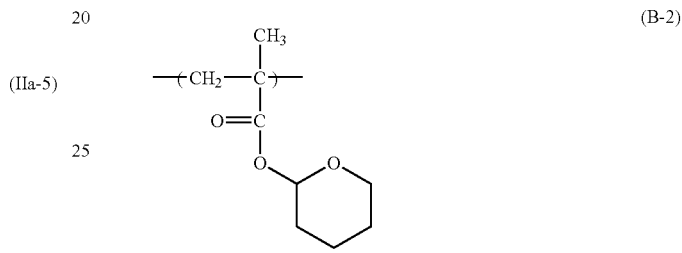

(B-3) 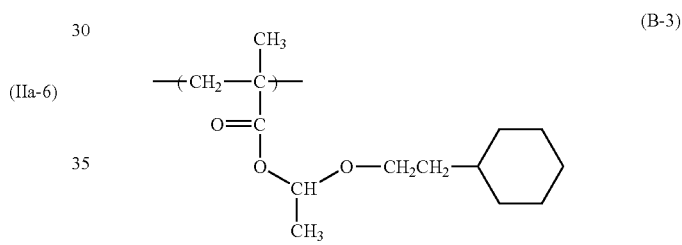

(B-4) 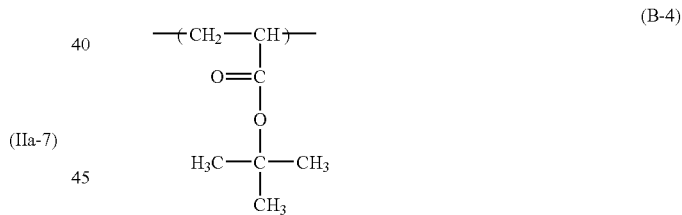

(B-5) 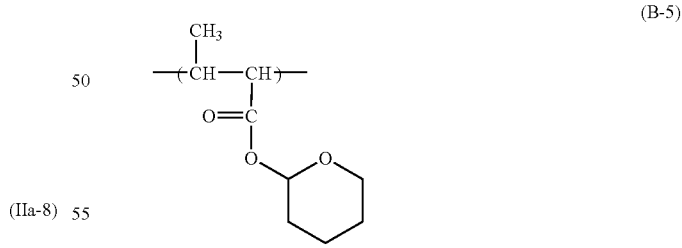

(B-6) 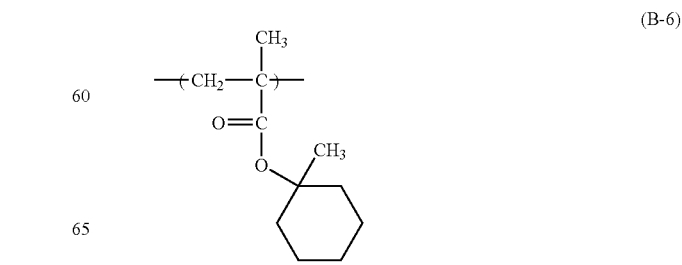

-continued
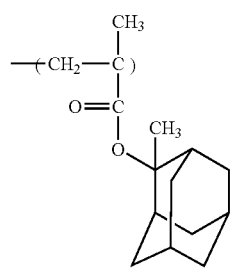
(B-7)
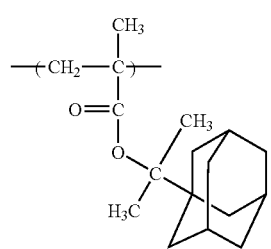
(B-8)
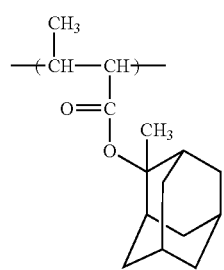
(B-9)
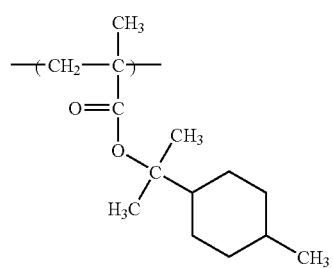
(B-10)
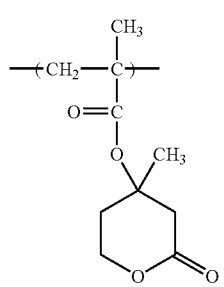
(B-11)
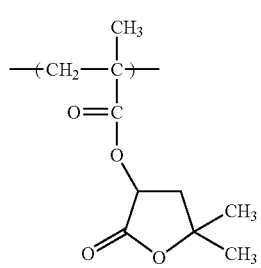
(B-12)
-continued
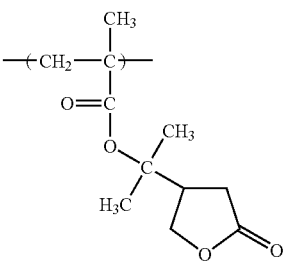
(B-13)
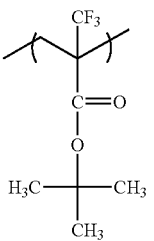
(B-1')
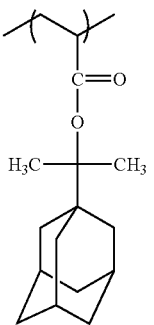
(B-8')
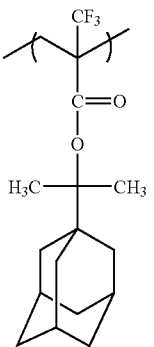
(B-8")
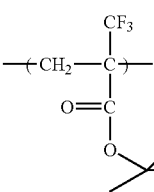
(B-12')
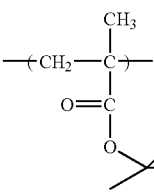
(B-12")

Further, as the specific examples of the repeating unit represented by the general formula (VIA), the repeating units (F-29) to (F-38) and (F-47) to (F-54) which were previously exemplified can be mentioned.

The specific examples of the repeating structural unit represented by the general formula (IIIA) are shown below, but the present invention is not limited to these.

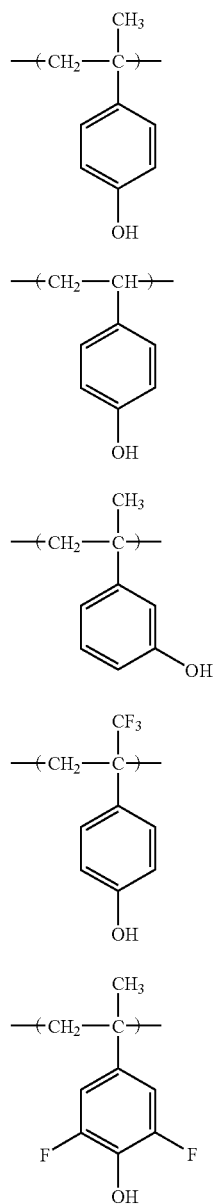

The specific examples of the repeating structural unit represented by the general formula (VIIA) are shown below, but the present invention is not limited to these.

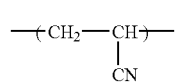

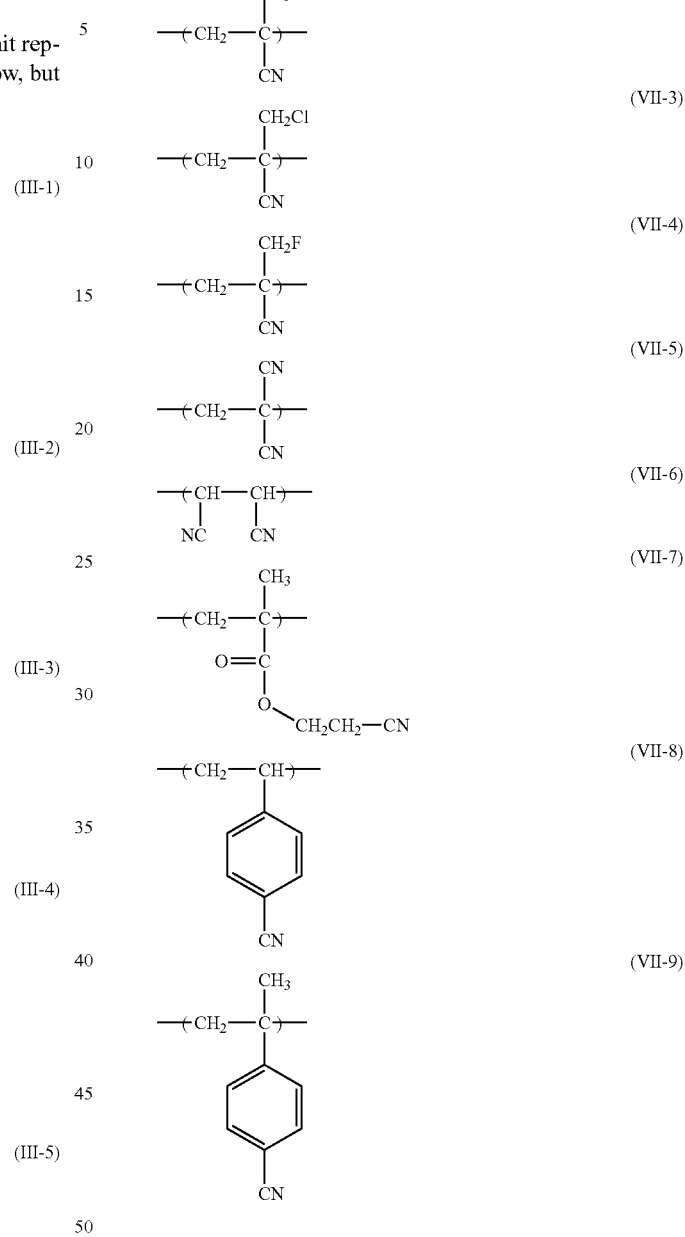

The fluorine group containing resin can be synthesized by radical polymerization in like manner as the alicyclic hydrocarbon-base acid-decomposable resin.

It is preferable that the component (B) has a silicon atom when the positive stimulation sensitive composition of the present invention is used in the upper resist of multilayered resist.

As the resin having a silison atom, and increasing the solubility in an alkali developing solution by the action of an acid, a resin having a silicon atom in at least one of a principal chain and a side chain is exemplified. Examples of the resin having a silison atom, and increasing the solubility in an alkali developing solution by the action of an acid include a resin having a siloxane structure in at least one of a principal chain and a side chain, a copolymer of an olefin type monomer having a silicon atom at a side chain, maleic anhydride and (meth) acylate type monomer having an acid-decomposable group at a side chain.

The weight average molecular weight of the component (B) related to the present invention is preferably 1,000 to 200,000 as a value converted to a polystyrene by the GPC method. When the weight average molecular weight is 1,000 or more, it is preferable from the viewpoint of the heat resistance and dry etching resistance, and when it is 200,000 or less, it is preferable from the viewpoint of the developing property and the film forming property.

In the stimulation sensitive composition of the present invention, the compounding amount of the resin composition of the component (B) related to the present invention is preferably 40 to 99.99% by weight in the total solid content, and more preferably 50 to 99.97% by weight.

(3) Compound having a molecular weight of not more than 3000 which is capable of decomposing by the action of acid to increase solubility in an alkali developing solution (hereinafter, referred to as the "component C" or "dissolution-inhibiting compound")

As the compound having a molecular weight of not more than 3000 which is capable of decomposing by the action of acid to increase solubility in an alkali developing solution, there are preferable the alicyclic or aliphatic compounds containing an acid-decomposable group such as a cholic acid derivative containing an acid decomposing resin which is described in "Proceeding of SPIE" 2724355 (1996), because it does not lower the transmission property of 220 nm or less. As the acid-decomposable group and alicyclic structure, there are mentioned those similar as those which were illustrated in the above-mentioned alicyclic hydrocarbon-base acid-decomposable resin.

When the stimulation sensitive composition of the present invention is exposed by KrF eximer laser or irradiated by electron beam, those containing a structure in which the phenolic hydroxyl group of a phenol compound was substituted with an acid decomposing resin are preferable. The phenol compound is preferably those containing 1 to 9 of phenol skeletons and more preferably those containing 2 to 6.

The molecular weight of the dissolution-inhibiting compound is 3000 or less, preferably 300 to 3000 and further preferably 500 to 2500.

The amount of the dissolution-inhibiting compound is preferably 3 to 50% by weight based on the solid content of the stimulation sensitive composition and more preferably 5 to 40% by weight.

The specific examples of the dissolution-inhibiting compound are shown below, but it is not limited to these.

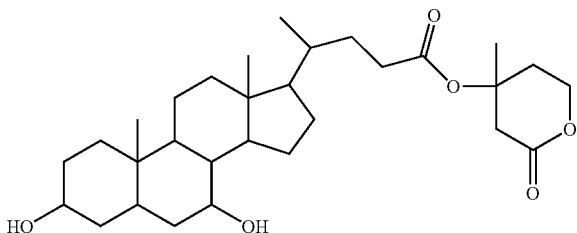

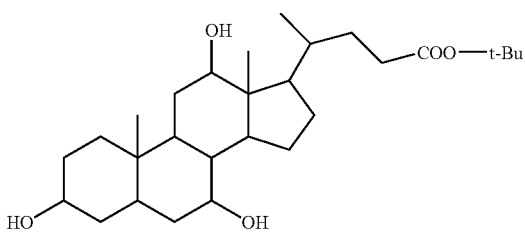

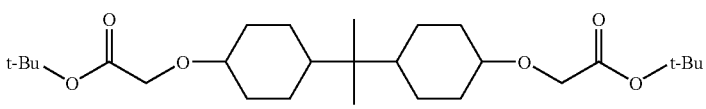

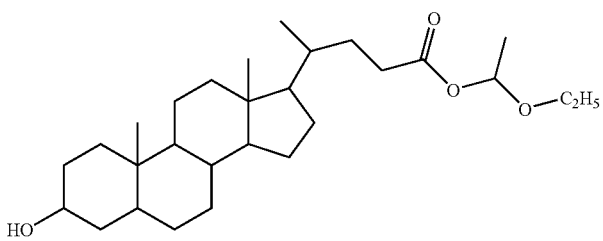

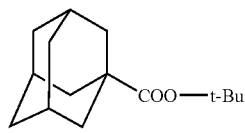

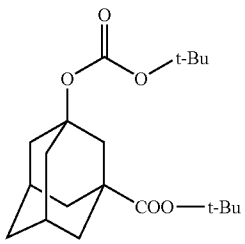
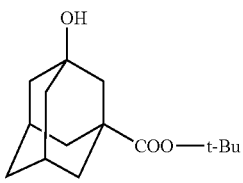

(4) (D) Resin which is soluble in an alkali developing solution (hereinafter, referred to as the "component D" or "alkali-soluble resin")

It is preferable that the alkali dissolution speed of the alkali-soluble resin is those being 20 Å/sec or more by measured by 0.261N tetrahydromethylammonium hydroxide (TMAH) (23° C.) Those being 200 Å/sec or more is preferable in particular (Å is angstrom).

As the alkali-soluble resin used for the present invention, for example, there can be mentioned a novolac resin, a hydrogenated novolac resin, an acetone-pyrogallol resin, an o-polyhydroxystyrene, a m-polyhydroxystyrene, a p-polyhydroxystyrene, a hydrogenated polyhydroxystyrene, a halogen or alkyl-substituted polyhydroxystyrene, a hydroxystyrene-N-substituted maleimide copolymer, an o/p- or m/p-hydroxystyrene copolymer, a partially O-alkylated product for the hydroxy group of polyhydroxystyrene (for example, an O-methylated product of 5 to 30 mol %, an O-(1-methoxy)ethylated product, a n O-(1-methoxy)ethylated product, an O-2-tetrahydropyranylated product, an O-(tert-butoxycarbonyl)methylated product), or an O-acylated product (for example, an O-acetylated product of 5 to 30 mol %, an O-(tert-butoxy) carbonylated product), a styrene-maleic anhydride copolymer, a styrene-hydroxystyrene copolymer, an α-methylstyrene-hydroxystyrene copolymer, a carboxyl group-containing methacryl-base resin and its derivative and a poly(vinyl alcohol) derivative; but it is not limited to these.

The preferable alkali soluble resin in particular is a novolac resin, a hydrogenated novolac resin, an o-polyhydroxystyrene, a m-polyhydroxystyrene, a p-polyhydroxystyrene and a copolymer thereof, an alkyl-substituted polyhydroxystyrene, a partially O-alkylated product of polyhydroxystyrene or a partially O-acylated product of polyhydroxystyrene, a styrene-hydroxystyrene copolymer and an α-methylstyrene-hydroxystyrene copolymer.

Said novolac resin can be obtained by carrying out addition condensation with aldehydes in the presence of an acidic catalyst using a fixed monomer as a principal component.

Further, the weight average molecular weight of the alkali soluble resin is 2000 or more, preferably 5000 to 200000 and more preferably 5000 to 100000.

Hereat, the weight average molecular weight is defined by a value converted to a polystyrene by gel permeation chromatography.

The alkali-soluble resin (D) in the present invention may be used in combination of 2 or more.

The amount of the alkali soluble resin used is 40 to 97% by weight based on the solid content of the total composition of the stimulation sensitive composition.

(5) (E) Crosslinking agent which is capable of crosslinking with the alkali-soluble resin by action of acid (hereinafter, referred to as the component (E) or "crosslinking agent")

The crosslinking agent is used for the negative-type stimulation sensitive composition of the present invention.

As the crosslinking agent, any one can be used so far as it is a compound crosslinking the resin soluble in alkali developing solution by action of an acid, but the following compounds (1) to (3) are preferable.

(1) The hydroxymethyl compound, alkoxymethyl compound and acyloxymethyl compound of a phenol derivative.

(2) A compound having a N-hydroxymethyl group, a N-alkoxymethyl group and a N-acyloxymethyl group.

(3) A compound having an epoxy group.

The alkoxymethyl group is preferably a group having 6 or less carbon atoms, and the acyloxymethyl group is preferably a group having 6 or less carbon atoms.

Among these crosslinking agents, preferable agents in particular are mentioned below.

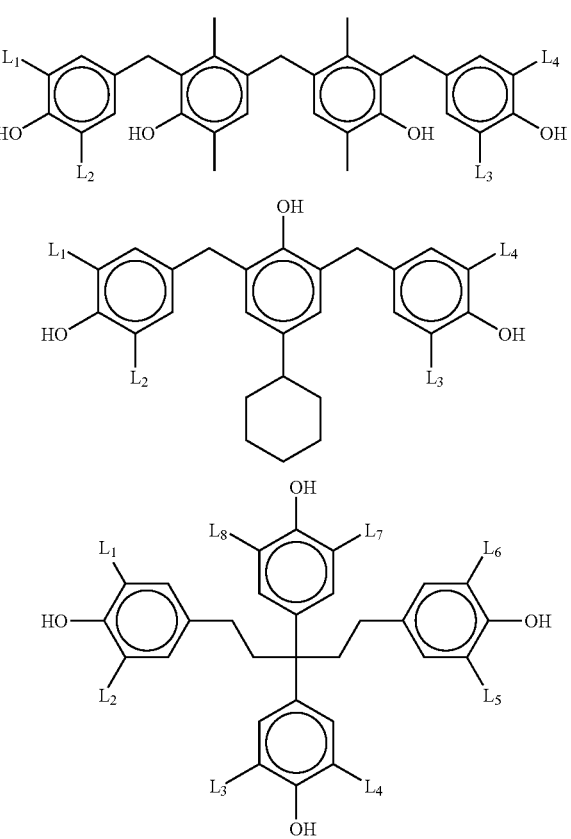

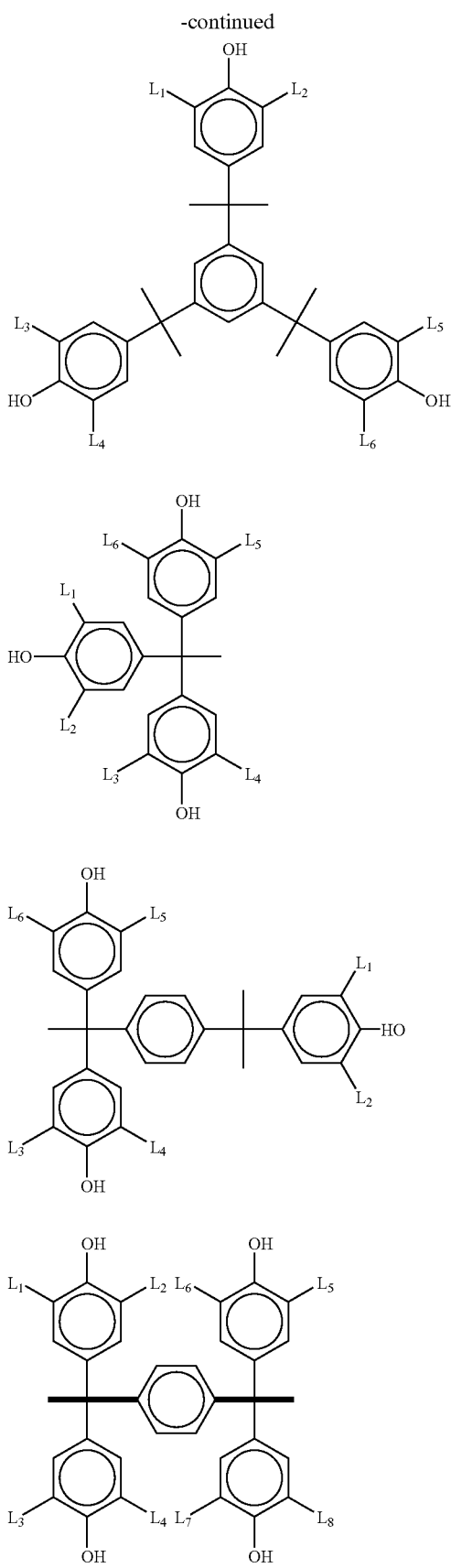

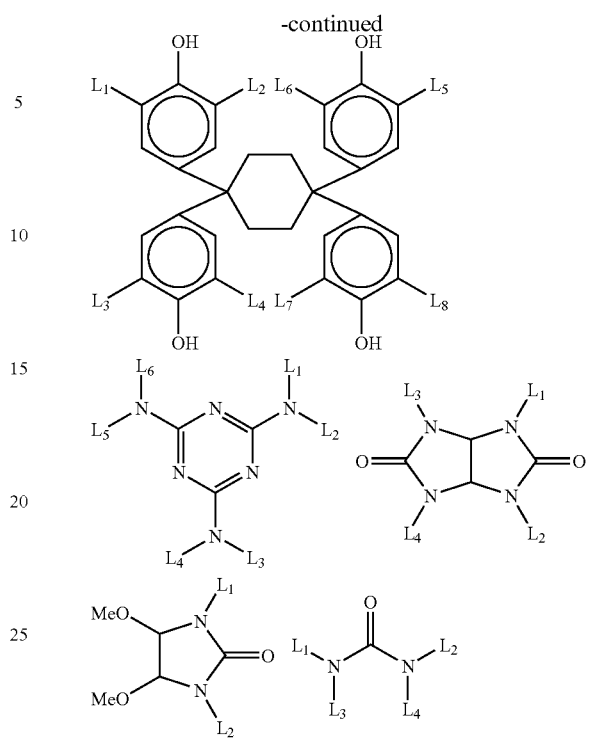

In the formulae, $L_1$ to $L_8$ may be the same or different, and represent a hydrogen atom, a methoxymethyl group, an ethoxymethyl group, or an alkyl group having 1 to 6 carbon atoms.

The amount of the crosslinking agent is preferably 3 to 70% by weight and more preferably 5 to 50% by weight in the solid content of the stimulation sensitive composition.

The amount of the crosslinking agent is preferably 3% by weight or more in the vierpoint of the film residual rate. Moreover, the amount of the crosslinking agent is preferably 70% by weight or less from the viewpoint of the resolution, the stability at preservation of the composition.

<Other Components Used for Stimulation Sensitive Composition of Present Invention>

(6) (F) Basic Compound

It is preferable that the stimulation sensitive composition of the present invention contains a basic compound (F) in order to reduce the change of performance due to the lapse of time from exposure to heating.

As the preferable structure, structures indicated by the under-mentioned formulae (A) to (E) can be mentioned.

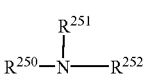

(A)

Hereat, each of $R^{250}$, $R^{251}$ and $R^{252}$ independently represents a hydrogen atom, an alkyl group having 1 to 20 carbon atoms, an aminoalkyl group having 1 to 20 carbon atoms, a hydroxyalkyl group having 1 to 20 carbon atoms or a substituted or unsubstituted aryl group, and $R^{250}$ and $R^{251}$ may be bonded to each other to form a ring, hereat.

Further, these may contain an oxygen atom, a sulfur atom and a nitrogen atom in an alkyl chain.

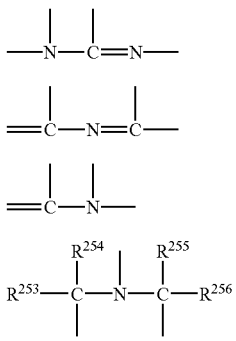

In the formulae, each of $R^{253}$, $R^{254}$, $R^{255}$ and $R^{256}$ independently represents an alkyl group having 1 to 20 carbon atoms.

As the preferable compound, there can be mentioned substituted or unsubstituted guanidine, substituted or unsubstituted aminopyrrolidine, substituted or unsubstituted pyrazole, substituted or unsubstituted pyrazoline, substituted or unsubstituted piperazine, substituted or unsubstituted aminomorpholine, substituted or unsubstituted aminoalkylmorpholine, and substituted or unsubstituted piperidine. As the further preferable compound, there can be mentioned a compound having an imidazole structure, a diazabicyclo structure, an onium hydroxide structure, an onium carboxylate structure, a trialkylamine structure, an aniline structure or a pyridine structure, an alkylamine derivative having a hydroxy group and/or an ether bond, an aniline derivative having a hydroxy group and/or an ether bond, and the like.

As the compound having an imidazole structure, imidazole, 2,4,5-triphenylimidazole, benzimidazole and the like are mentioned. As the compound having a diazabicyclo structure, 1,4-diazabicyclo[2,2,2]octane, 1,5-diazabicyclo[4,3,0] non-5-en, 1,8-diazabicyclo[5,4,0]undec-7-en, and the like are mentioned. As the compound having an onium hydroxide structure, there are mentioned triarylsulfonium hydroxide, phenancylsulfonium hydroxide, sulfonium hydroxide having a 2-oxoalkyl group, specifically, triphenylsulfonium hydroxide, bis(tert-butylphenyl)iodonium hydroxide, phenancylthiophenium hydroxide, 2-oxopropylthiophenium hydroxide, and the like. As the compound having an onium carboxylate structure, the anion portion of a compound having an onium hydroxide structure became a carboxylate, and for example, acetate, adamanthane-1-carboxylate, perfluoroalkylcarboxylate and the like are mentioned. As the compound having a trialkylamine structure, tri(n-butyl) amine, tri(n-octyl)amine and the like are mentioned. As the aniline compound, 2,6-diisopropylaniline, N,N-dimethylaniline and the like are mentioned. As the alkylamine derivative having a hydroxy group and/or an ether bond, there can be mentioned ethanolamine, dithanolamine, triethanolamine, tris(methoxyethoxyethyl)amine, and the like. As the aniline derivative having a hydroxy group and/or an ether bond, N,N-bis(hydroxyethyl)aniline and the like can be mentioned.

These basic compounds are used alone, or 2 or more are used. The amount of the basic compound used is usually 0.001 to 10% by weight based on the solid content of the stimulation sensitive composition, and preferably 0.01 to 5% by weight.

the amount of the basic compound is preferably 0.001% by weight or more, so that the effect of adding the above-mentioned basic compound can be sufficiently obtained. On the other hand, it is preferably 10% by weight or less from the viewpoint of sensitivity and the developing property of non exposure portion.

(7) (G) Surfactant containing at least one of a group consisting of a fluorine atom and a silicon atom (hereinafter, referred to as the component (G) or "a fluorine-base and/or silicon-base surfactant")

It is preferable that the stimulation sensitive composition of the present invention contains further either of, or 2 or more of a fluorine-base and/or silicon-base surfactant (a fluorine-base surfactant and a silicon-base surfactant, a surfactant containing both of fluorine and silicon).

Since the stimulation sensitive composition of the present invention contains the fluorine-base and/or silicon-base surfactant, it is possible to provide a resist pattern having good sensitivity and resolution, and the little defects of adherence and development at the use of exposure light source of 250 nm or less, in particular 220 nm or less.

As the fluorine-base and/or silicon-base surfactant, for example, there can be mentioned surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2000-277862, U.S. Pat. Nos. 5,405,720, 5,360,692, 5,529,881, 5,296,330, 5,436,098, 5,576,143, 5,294,511 and 5,824,451, and commercially available surfactants described below can be used as they are.

As the commercially available surfactants, for example, there can be mentioned fluorine-base surfactants or silicon-base surfactants such as FTOP EF301 and EF303 (manufactured by Shin Akita Chemicals Co.), FLUORAD FC430 and FC431 (manufactured by Sumitomo 3M Limited), MEGAFAC F171, F173, F176, F189 and R08 (manufactured by Dainippon Ink and Chemicals, Incorporated), SURFLON S-382, SC101, SC102, SC103, SC104, SC105 and SC106 (manufactured by Asahi Glass Co., Ltd.), and TROYSOL S-366 (manufactured by Troy Chemical Industries, Inc.). Further, POLYSILOXANE POLYMER KP-341 (manufactured by Shin-Etsu Chemical Co., Ltd.) can be also used as the silicon-base surfactant.

Further, as the surfactant, there can be used a surfactant using a polymer having a fluoroaliphatic group which was introduced from a fluoroaliphatic compound produced by a telomerization method (also called as a telomer method) or an oligomerization method (also called as an oligomer method), in addition to the known surfactants described above. The fluoroaliphatic compound can be synthesized by the method described in JP-A-2000-90991.

The polymer having a fluoroaliphatic group is preferably a copolymer of a monomer having a fluoroaliphatic group with a (poly(oxyalkylene))acrylate and/or a (poly(oxyalkylene)) methacrylate, and it may be randomly distributed or may be obtained by block copolymerization.

Further, as the poly(oxyalkylene) group, a poly (oxyethylene) group, a poly (oxypropylene) group, a poly (oxybutylene) group and the like are mentioned. Further, a poly (a block linking body of oxyethylene with oxypropylene) and a unit having an alkylene with a different chain length in the same chain length as in the poly(a block linking body of oxyethylene with oxypropylene) maybe used. Further, not only a copolymer of a monomer having a fluoroaliphatic group with a (poly(oxyalkylene))acrylate and/or a (poly(oxyalkylene))methacrylate, but also a copolymer having 3 kinds or more which was obtained by simultaneously copolymerizing a monomer having two or more different fluoroaliphatic groups, two or more different(poly(oxyalkylene))acrylates (or methacrylate) and the like may be used.

For example, as the commercially available surfactants, there can be mentioned MEGAFAC F470, F473, F475, F476 and F472 (manufactured by Dainippon Ink and Chemicals Inc.). Further, a copolymer of an acrylate (or methacrylate) having a $C_6F_{13}$ group with a (poly(oxyalkylene))acrylate (or methacrylate), a copolymer of an acrylate (or methacrylate) having a $C_6F_{13}$ group with a (poly(oxyethylene))acrylate (or methacrylate) and a (poly(oxypropylene))acrylate (or methacrylate), a copolymer of an acrylate (or methacrylate) having a $C_8F_{17}$ group with a (poly(oxyalkylene))acrylate (or methacrylate), a copolymer of an acrylate (or methacrylate) having a C8F17 group with a (poly(oxyethylene))acrylate (or methacrylate) and a (poly(oxypropylene))acrylate (or methacrylate), and the like.

The amount of the fluorine-base and/or silicon-base surfactant used is preferably 0.0001 to 2% by weight based on the total solid content (excluding a solvent) of the stimulation sensitive composition, and more preferably 0.001 to 1% by weight.

(H) Organic Solvent

The stimulation sensitive composition of the present invention uses dissolving the above-mentioned components in a fixed organic solvent.

As the organic solvent used, for example, there can be mentioned ethylene dichloride, cyclohexanone, cyclopentanone, 2-heptanone, γ-butyrolactone, methyl ethyl ketone, ethyleneglycol monomethyl ether, ethyleneglycol monoethyl ether, 2-methoxyethyl acetate, ethyleneglycol monoethyl ether acetate, propyleneglycol monomethyl ether, propyleneglycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethylsulfoxide, N-methylpyrrolidone, tetrahydrofuran and the like.

In the present invention, the organic solvent may be used alone, and may be used in mixture, but it is preferable to use a mix solvent which mixed a solvent containing a hydroxy group in the structure and a solvent not containing a hydroxy group. Thus, the generation of particles at the preservation of a resist solution can be reduced.

As the solvent containing a hydroxy group, for example, there can be mentioned ethyleneglycol, ethyleneglycol monomethyl ether, ethyleneglycol monoethyl ether, propyleneglycol, propyleneglycol monomethyl ether, propyleneglycol monoethyl ether, ethyl lactate and the like. Among these, propyleneglycol monomethyl ether and ethyl lactate are preferable in particular.

As the solvent not containing a hydroxy group, for example, there can be mentioned propyleneglycol monomethyl ether acetate, ethyl ethoxypropionate, 2-heptanone, γ-butyrolactone, cyclohexanone, butyl acetate, N-methylpyrrolidone, N,N-dimethylacetamide, dimethylsulfoxide, and the like. Among these, propyleneglycol monomethyl ether acetate, ethyl ethoxypropionate, 2-heptanone, γ-butyrolactone, cyclohexanone and butyl acetate are preferable in particular. Propyleneglycol monomethyl ether acetate, ethyl ethoxypropionate and 2-heptanone are most preferable.

The mix ratio (weight) of the solvent containing a hydroxy group in the structure to the solvent not containing a hydroxy group is 1/99 to 99/1, preferably 10/90 to 90/10 and further preferably 20/80 to 60/40. The mix solvent containing 50% by weight of the solvent not containing a hydroxy group is preferable in particular, from the viewpoint of coating uniformity.

<Other Additive>

In the stimulation sensitive composition of the present invention, a dye, a plasticizer, a surfactant other than the above-mentioned component (G), a photosensitizer, and a compound for accelerating the solubility to a developing solution and the like can be contained, if necessary.

The compound for accelerating the solubility to a developing solution which can be used in the present invention is a low molecular weight compound having 2 or more of phenolic OH groups or one or more of carboxylic groups and a molecular weight of 1000 or less. When it has carboxylic groups, an alicyclic compound or an aliphatic compound is preferable.

The preferable addition amount of these solubility accelerating compounds is 2 to 50% by weight based on the resin (B) or the resin (D) and preferably 5 to 30% by weight. When the addition amount is 50% by weight or less, it is preferable because developing residue and deformation of the pattern at development are restrained.

The phenol compounds having a molecular weight of 1000 or less can be easily synthesized by those skilled in the art, referring methods described in, for example, JP-A-4-122938, JP-A-2-28531, U.S. Pat. No. 4,916,210, EP 219294 and the like.

As the specific examples of the alicyclic compound or aliphatic compound containing carboxylic groups, there are mentioned carboxylic derivatives having a steroid structure such as cholic acid, deoxycholic acid and lithocholic acid; an adamantane carboxylic acid derivative, adamantane dicarboxylic acid, cyclohexane carboxylic acid and the like, but they are not limited to these.

In the present invention, other surfactants other than the fluorine-base and/or silicon-base surfactant can be also added. Specifically, there can be mentioned nonion-base surfactants such as polyoxyethylene alkyl ethers, polyoxyethylene alkylallyl ethers, polyoxyethylene-polyoxyproylene block copolymers, sorbitan aliphatic esters, and polyoxyethylene sorbitan aliphatic esters.

These surfactants may be added alone and a combination of several surfactants can be used.

<Use Method>

The stimulation sensitive composition of the present invention is used by dissolving the above-mentioned components in the fore-mentioned preferable mix solvent and then coating it on a fixed support.

For example, the stimulation sensitive composition is coated on a substrate (for example, silicon/silicon dioxide coating) used for production of a precise integrated circuit device by appropriate methods such as a spinner and a coater.

After coating, stimulation from the external is imparted through a fixed mask, and baking is carried out to be developed. Thus, a good pattern can be obtained. As the stimulation from the external, there can be mentioned as actinic rays such as infrared rays, visible light, ultraviolet rays, far ultraviolet rays, X-rays and electron beam, heat, and ultra sonic. Far ultraviolet rays having a wave length of preferably 250 nm or less and more preferably 220 nm or less is preferable, and specifically, actinic rays such as KrF eximer laser (248 nm), ArF eximer laser (193 nm), $F_2$ eximer laser (157 nm), X-rays and electron beam; and ArF eximer laser (193 nm) and $F_2$ eximer laser (157 nm) are most preferable.

The developing solution is used as follow at the developing step. As the developing solution of the resist composition, there can be used aqueous alkali solutions such as inorganic alkalis such as sodium hydroxide, potassium hydroxide, sodium carbonate, sodium silicate, sodium metasilicate and aqueous ammonia; primary amines such as ethylamine and propylamine; secondary amines such as diethylamine and di-n-butylamine; tertiary mines such as triethylamine and methyldiethylamine; alcohol amines such as dimethylethanolamine and triethanolamine; quaternary ammonium salts such as tetramethylammonium hydroxide and tetraethylammonium hydroxide; cyclic amines such as pyrole and piperidine.

Further, appropriate amounts of alcohols and a surfactant can be added in the above-mentioned alkali developing solution to be used.

The alkali concentration of the alkali developing solution is usually 0.1 to 20% by weight, preferably 0.2 to 15% by weight and further 0.5 to 10% by weight.

The pH of the alkali developing solution is usually 10.0 to 15.0, preferably 10.5 to 14.5 and further preferably 11.0 to 14.0.

EXAMPLES

The present invention is further specifically illustrated below according to Examples, but the content of the present invention is not limited thereto.

<Synthesis of Acid Generating Agent>

Synthesis Example 1

Synthesis of Compound (I-1)

10 g of isobutylophenone and 9.2 g of triethylamine were added to 10 ml of acetonitrile, and further 8.54 g of chlorotrimethylsilane was added. A solution in which 12.7 g of sodium iodide was dissolved in 100 ml of acetonitrile was added dropwise to the mix solution. After reaction at 60° C. for 6 hours, the reaction solution was poured on ice. This was extracted twice with hexane, and the organic phase was rinsed with water, dried and condensed to obtain a crude product. This was purified by distillation under reduced pressure (1 to 2 mmHg, 71° C.) to obtain trimethylsilylenol ether of isobutylophenone.

5 g of trimethylsilylenol ether of isobutylophenone and 2.4 g of tetramethylenesulfoxide were dissolved in 50 ml of chloroform, and this was cooled to −30° C. To the mix solution, 4.8 g of trifluoroacetic anhydride was added over 30 min. The mixture was left alone to room temperature, and reacted for 4 hours as it is. A solution in which 7,7 g of potassium nonafluorobutane sulfonate was added in acetonitrile/water was added to the reaction solution and the mixture was stirred for 30 minutes. To the solution, 100 ml of chloroform was additionally added, and the mixture was rinsed with water, dried and condensed to obtain an oily crude product. This was rinsed with diisopropyl ether to precipitate a powder. This was filtered and dried to obtain 4.8 g of the compound (I-1).

300 MHz$^1$H-NMR (CDCl$_3$)

δ 2.1(c, 6H), δ 2.2 to 2.5 (m, 4H), δ 2.6 (m, 1H), δ 3.5 to 3.8 (m, 4H), δ 7.55 (t, 2H), δ 7.7 (t, 1H), δ 7.9 (d, 2H)

Synthesis Example 2

Synthesis of Compound (I-39)

27 g of aluminum chloride and 100 ml of toluene were mixed and 25 g of t-butylacetyl chloride was added dropwise to this under ice cooling, After reaction at room temperature for 2 hours, the reaction solution was poured on ice. This was extracted with hexane, and the organic phase was rinsed with water and an aqueous sodium bicarbonate solution, dried and condensed. The crude product was purified by distillation under reduced pressure (95-96° C./2 mmHg) to obtain 32 g of 4-t-butylacetyltoluene. 20 g of 4-t-butylacetyltoluene, 19 g of sodium iodide and 13 g of triethylamine were mixed with 100 ml of acetonitrile, and 13.7 g of chlorotrimethylsilane was gradually added thereto The mixture was reacted at 60° C. for 5 hours, and left alone to be cooled. The reaction solution was poured on ice, this was extracted with diisopropyl ether, and the organic phase was rinsed with an aqueous sodium bicarbonate solution, dried and condensed. This was purified by distillation under reduced pressure (95-98° C./2 mmHg) to obtain 32 g of silylenol ether of 4-t-butylacetyltoluene. Under nitrogen flow, 23.9 g of silylenol ether and 14.8 g of dibutylsulfoxide were dissolved in 100 ml of chloroform. The solution was cooled to −30° C. or less, and to the solution, 19.1 g of trifluoroacetic anhydride was added over 30 min. After reaction at room temperature for one hour, a solution in which 30.8 g of potassium nonafluorobutane sulfonate was dissolved in acetonitrile/water was added to the reaction solution. This was extracted with chloroform, the organic phase was rinsed with distilled water until aqueous phase is neutral. The organic phase was condensed, and the crude product obtained was rinsed with hexane and then with water to precipitate a powder. This was further rinsed with hexane and water by slurry rinsing to obtain 21 g of the compound (I-39).

300 MHz$^1$H-NMR (CDCl$_3$)

δ 0.9 (m, 6H), δ 1.2(s,9H), δ 1.4 to 1.6 (m, 4H), δ 1.6 to 1.8 (m, 4H), δ 2.4 (s, 3H), δ 3.2 to 3.4 (2, 4H), δ 3.6 to 3.7 (m, 2H), δ 6.05 (2, 1H), δ 7.4 (d, 2H), δ 8.2 (d, 2H)

Synthesis Example 3

Synthesis of Compound (I-42)

31.3 g of aluminum chloride and 200 ml of carbon tetrachloride were mixed and 25 g of isobutylyl chloride was added dropwise to this under ice cooling. After stirring for 30 minutes, 31.1 g of phenylcyclohexane was added dropwise thereto. After reaction at room temperature for 2 hours, the reaction solution was poured in ice. This was extracted with chloroform, and the organic phase was rinsed with water and an aqueous sodium bicarbonate, dried and condensed. The crude product was purified by distillation under reduced pressure (143-148° C./2 mmHg) to obtain 48 g of 4-cyclohexylisobutylphenone. 20 g of 4-cyclohexylisobutylphenone, 15.6 g of sodium iodide and 10.5 g of triethylamine were mixed with 200 ml of acetonitrile, and 11.3 g of chlorotrimethylsilane was gradually added thereto. The mixture was reacted at 60° C. for 5 hours, and left alone to be cooled. The reaction solution was poured on ice, this was extracted with diisopropyl ether, and the organic phase was rinsed with an aqueous sodium bicarbonate solution, dried and condensed. This was purified by distillation under reduced pressure (141-144° C./2 mmHg) to obtain 19.6 g of silylenol ether of 4-cyclohexylisobutylphenone. Under nitrogen flow, 19.6 g of silylenol ether and 6.8 g of tetramethylene sulfoxide were dissolved in 150 ml of chloroform. The solution was cooled to −30° C. or less, and to the solution, 13.6 g of trifluoroacetic anhydride was added over 30 min. After reaction at room temperature for one hour, a solution in which 21.9 g of potassium nonafluorobutane sulfonate was dissolved in acetonitrile/water was added to the reaction solution. This was extracted with chloroform, the organic phase was rinsed with a 5% tetramethylammonium hydroxide aqueous solution in alkali, and then rinsed with distilled water until aqueous phase is neutral. The organic phase was condensed, and diisopropyl ether was added to the crude product obtained to precipitate a powder.

This was recrystallized from ethyl acetate/diisopropyl ether (100/150), and filtered to obtain 14 g of the compound (I-42).

300 MHz $^1$H-NMR (CDCl$_3$)

δ 1.4 (m, 6H), δ 1.8(m, 4H), δ 2.15 (s, 6H), δ 2.2 to 2.4 (m, 4H), δ 2.6 (m, 1), δ 3.4 to 3.7 (m, 4H), δ 7.4 (d, 2H), δ 7.9 (d, 2H)

<Synthesis of Resin (B)>

Synthesis Example 1

Synthesis of Resin (I) (Side Chain Type)

2-Ethyl-2-adamantyl methacrylate and butyrolactone methacrylate were charged at a proportion of 55/45 and dissolved in methyl ethyl ketone/tetrahydrofuran=5/5, and 100 ml of a solution having a solid concentration of 20% was prepared. To the solution, 2% by mol of V-65 manufactured by Wako Pure Chemicals Co. was added, and this was added dropwise over 4 hours in 10 ml of methyl ethyl ketone which was heated at 60° C. to be stirred for 4 hours. After termination of the dropwise addition, the reaction solution was heated for 4 hours, V-65 was added again by 1% by mol, and the solution was stirred for 4 hours. After termination of the reaction, the reaction,solution was cooled to room temperature and crystallized in 3L of a mix solvent of distilled water/isopropyl alcohol=1/1, and the resin (1) being a white powder which was precipitated was recovered.

The polymer composition ratio which was determined from C$^{13}$NMR was 46/54. Furthers the weight average molecular weight converted to a standard polystyrene which was determined by GPC measurement was 10700.

The resins (2) to (12), (26) to (31) were synthesized in like manner as the above-mentioned Synthesis Example 1.

The structures and molecular weights of the resins (1) to (12), (26) to (31) are shown below.

-continued

| | Molecular Weight |
|---|---|
| (5) | 8900 |
| (6) | 11300 |
| (7) | 8900 |
| (8) | 11700 |
| (9) | 9800 |

-continued

| | Molecular Weight |
|---|---|
| (10) | 8700 |
| (11) | 13400 |
| (12) | 10900 |
| (26) | 9300 |
| (27) | 7600 |

-continued

| | Molecular Weight |
|---|---|
| (28) [structures] | 7300 |
| (29) [structures] | 7600 |
| (30) [structures] | 8400 |
| (31) [structures] | 6500 |

Synthesis Example 2

Synthesis of Resin (13) (Main Chain Type)

Tert-butyl norbornenecarboxylate, butyrolactone norbornenecarboxylate and maleic anhydride (molar ratio=40/10/50) and THF (reaction concentration=60% by weight) were charged in a separable flask, and the mixture was heated at 60° C. under nitrogen flow. When the reaction temperature came to be stable, a radical initiator V-601 which was manufactured by Wako Pure Chemicals Co. was added by 2% by mol to initiate the reaction. After the resultant reaction mixture was diluted to 2-fold by tetrahydrofuran, it was charged in a mix solvent of hexane/isopropyl alcohol=1/1 to precipitate a white powder. The precipitated powder was filtered to be taken out and dried, and the resin (13) being an objective product was recovered, When the molecular weight analysis of the resultant resin (13) was tried, the molecular weight converted to a polystyrene was 8300 (weight average). Further, it was confirmed that the molar ratio of the repeating unit of tert-butyl norbornene carboxylate/butyrolactone norbornene carboxylate/maleic anhydride of the resin (1) was 42/8/50 by NMR spectrum.

The resins (14) to (19) were synthesized in like manner as Synthesis Example 2.

The structures and molecular weights of the resins (13) to (19) are shown below.

| | | | Molecular Weight |
|---|---|---|---|
| (13) | structures | | 8300 |
| (14) | structures | | 8200 |
| (15) | structures | | 9600 |
| (16) | structures | | 5800 |
| (17) | structures | | 4700 |
| (18) | structures | | 8500 |

-continued

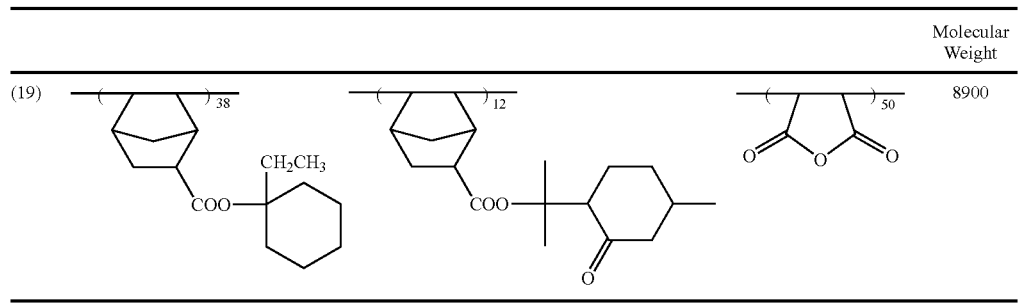

Synthesis Example 3

Synthesis of Resin (20) (Hybrid Type)

Norbornene, maleic anhydride, tert-butyl acrylate and 2-methylcyclohexyl-2-propylacrylate were charged in a reaction vessel at a molar ratio of 35/35/20/10, and dissolved in tetrahydrofuran to prepare a solution having a solid content of 60%. This was heated at 65° C. under nitrogen flow. When the reaction temperature came to be stable, a radical initiator V-601 which was manufactured by Wako Pure Chemical Industries, Ltd. was added by 1% by mol to initiate the reaction. After being heated for 8 hours, the reaction mixture was diluted to 2-fold by tetrahydrofuran, and then it was charged in 5-fold volume of hexane to precipitate a white powder. The precipitated powder was filtered to be taken out, and precipitated again in 5-fold volume of a mix solvent of hexane/tert-butyl methyl ether=1/1. The precipitated powder was filtered and dried to obtain the resin (20) being an objective product.

When the molecular weight analysis by GPC of the resultant resin (20) was tried, the molecular weight converted to a polystyrene was 12100 (weight average). Further, the composition of the resin (1) was the molar ratio of norbornene/maleic anhydride/tert-butyl acrylate/2-methylcyclohexyl-2-propylacrylate=32/39/19/10 by NMR spectrum.

The resins (21) to (25) were synthesized in like manner as Synthesis Example 3.

The structures and molecular weights of the resins (20) to (25) are shown below.

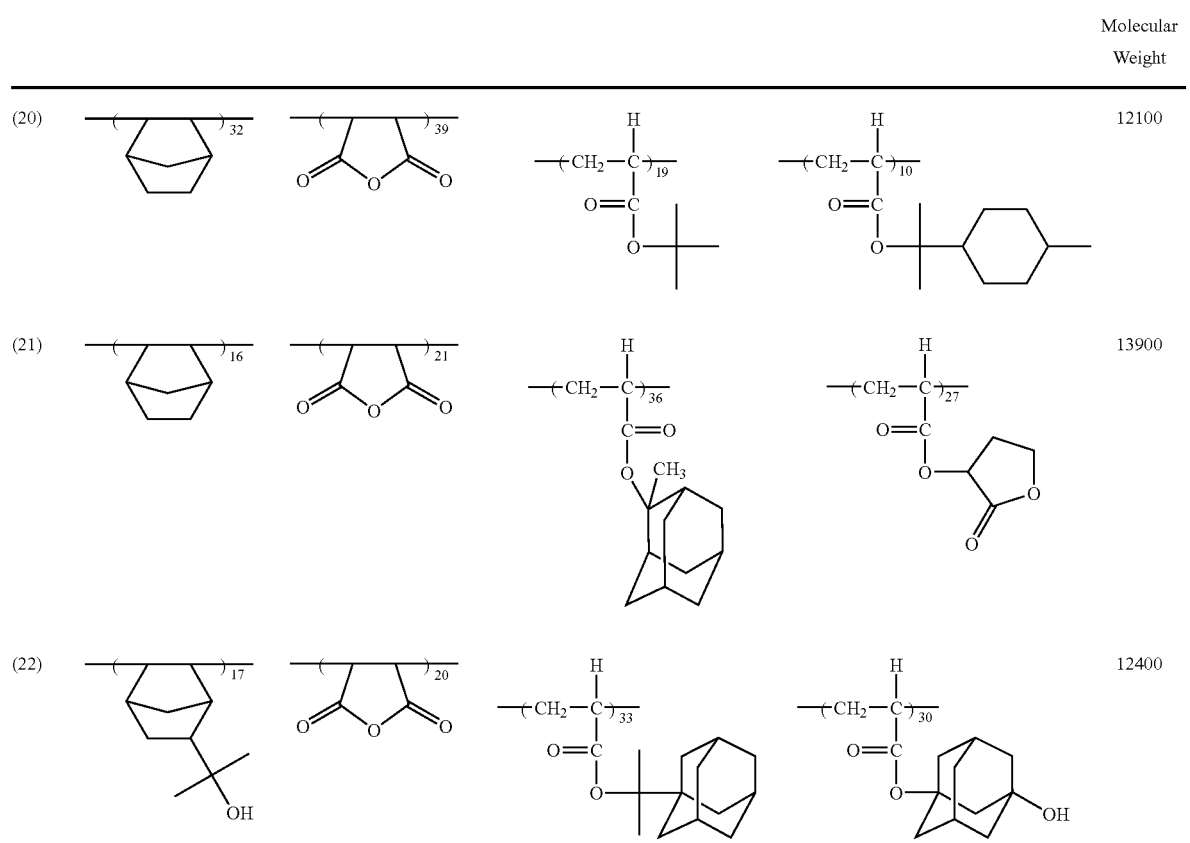

-continued

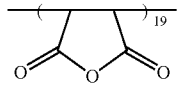
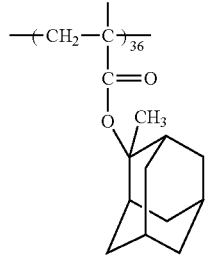

Synthesis Example 4

Synthesis of Resin (FII-1)

20 g of tert-butyl α-trifluoromethylacrylate and 20 g of 3-(2-hydroxymethyl-2,2-bistrifluoromethylethyl)norbornene were dissolved in 40 g of tetrahydrofuran and the mixture was heated at 70° C. under nitrogen flow. Thereto, 2.0 g of a polymerization initiator V-65 which was manufactured by Wako Pure Chemical Industries, Ltd. was added thereto, and the mixture was stirred for 6 hours as it is. After being left alone to room temperature, 300 ml of hexane was added to the reaction solution, and the precipitated resin was recovered. After the resultant resin was dissolved in acetone, hexane was added again to remove an unreacted monomer and an oligomer component, and the resin (FII-1) used for the present invention was obtained.

The resins (FII-2) to (FII-24) were synthesized in like manner as Synthesis Example 4.

The structures of the resins (FII-1) to (FII-24) are shown below.

Further, the weight average molecular weights and the like of the resins (FII-1) to (FII-24) are shown the under-mentioned Table 1.

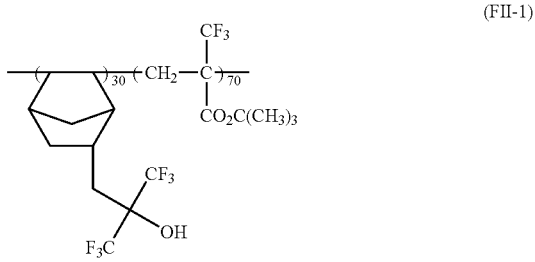

(FII-1)

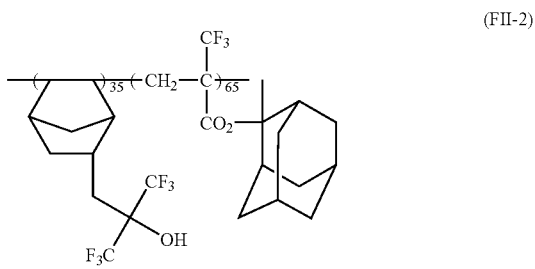

(FII-2)

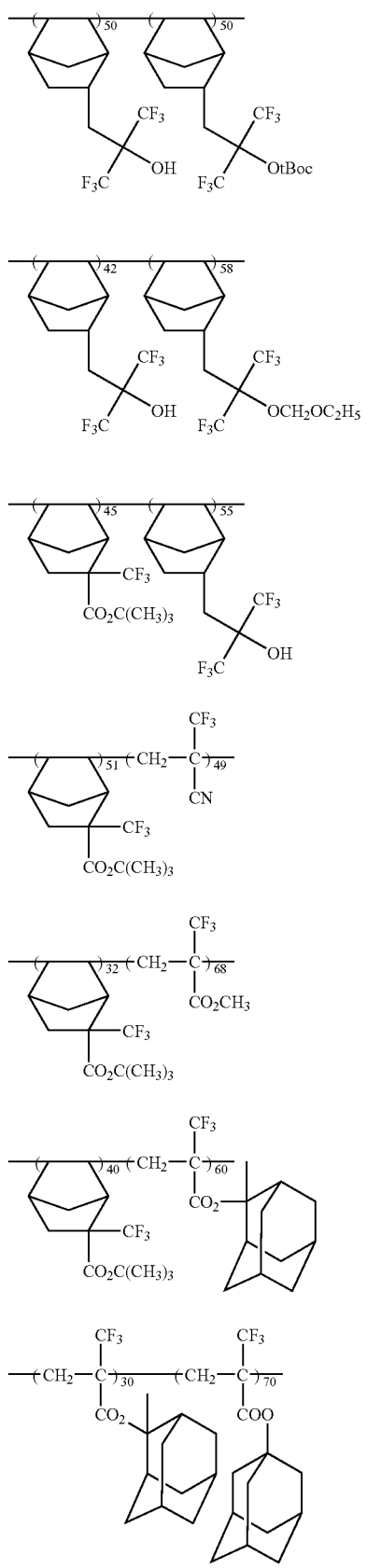
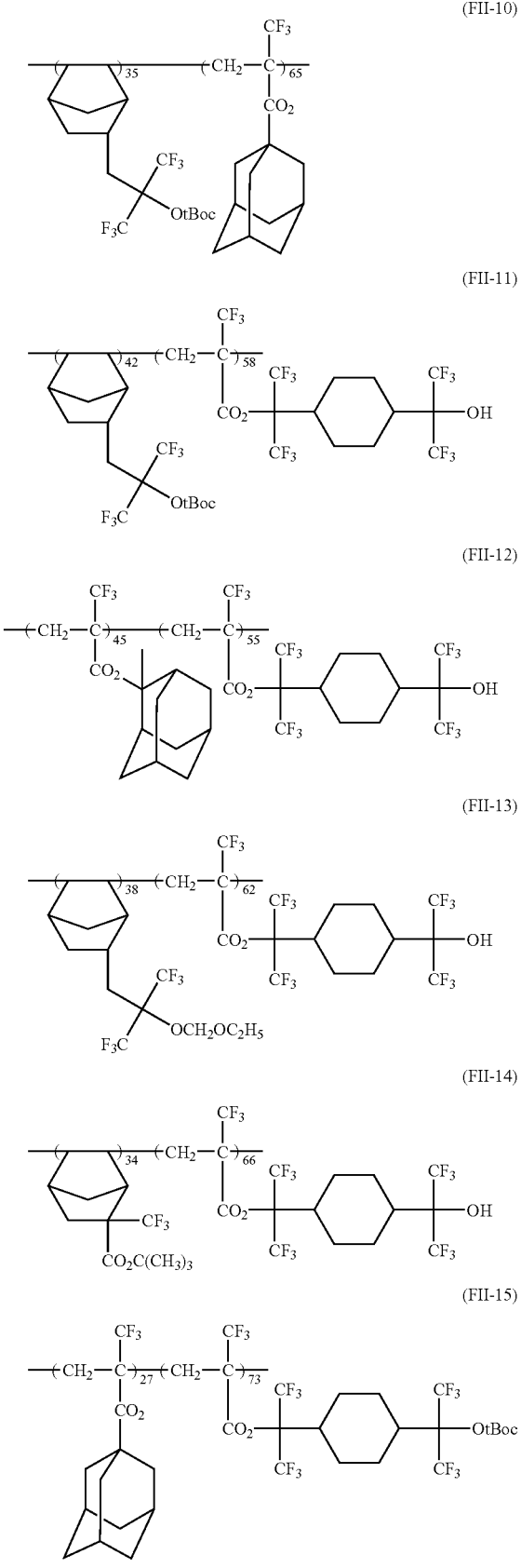

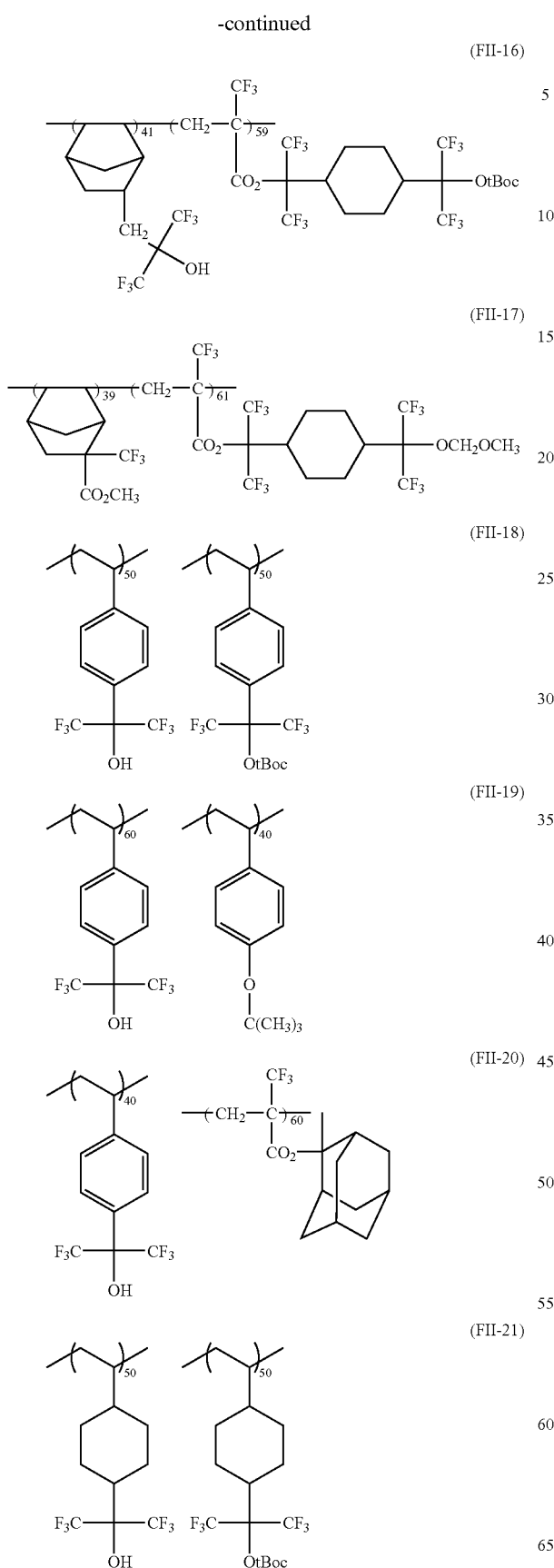
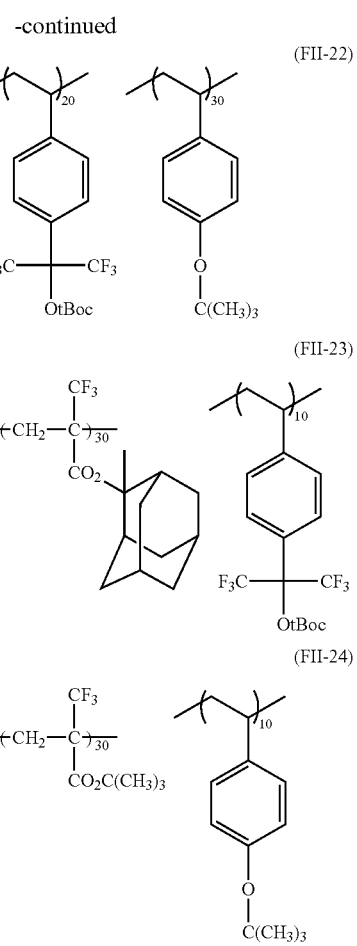
TABLE 1
| Resin | Weight average molecular weight Mw | Degree of distribution | Content rate of oligomer having molecular weight of 1000 or less |
|---|---|---|---|
| (FII-1) | 15200 | 1.45 | 5 |
| (FII-2) | 24000 | 1.75 | 8 |
| (FII-3) | 18200 | 1.85 | 7 |
| (FII-4) | 16500 | 1.46 | 6 |
| (FII-5) | 9500 | 1.58 | 8 |
| (FII-6) | 19500 | 2.02 | 8 |
| (FII-7) | 6500 | 1.85 | 7 |
| (FII-8) | 28400 | 1.68 | 9 |
| (FII-9) | 28600 | 1.44 | 5 |
| (FII-10) | 12800 | 1.65 | 8 |
| (FII-11) | 16800 | 1.68 | 9 |
| (FII-12) | 28400 | 1.58 | 6 |
| (FII-13) | 19800 | 1.69 | 8 |
| (FII-14) | 8700 | 1.95 | 8 |
| (FII-15) | 15200 | 1.46 | 7 |
| (FII-16) | 19500 | 1.65 | 4 |
| (FII-17) | 16900 | 1.42 | 8 |
| (FII-18) | 15900 | 1.85 | 9 |
| (FII-19) | 15000 | 1.55 | 4 |
| (FII-20) | 12500 | 1.88 | 8 |
| (FII-21) | 25000 | 1.68 | 9 |
| (FII-22) | 16000 | 1.54 | 7 |
| (FII-23) | 14600 | 1.95 | 5 |
| (FII-24) | 17500 | 1.48 | 5 |

<Resin (D)>

The structures, molecular weights and molecular weight distributions of the resins (D) used in Examples are shown below.

| | Mw | Mw/Mn |
|---|---|---|
| P-1 (structure) | 17000 | 2.15 |
| P-2 (structure) | 16000 | 2.30 |
| P-3 (structure) | 19000 | 2.2 |
| P-4 (structure) | 12000 | 1.2 |
| P-5 (structure) | 21000 | 2.1 |
| P-6 (structure) | 6000 | 1.2 |

VP-5000 manufactured by Nippon Soda Co., Ltd.

<Crosslinking Agent (E)>

The structures of the crosslinking agents used in Examples are shown below.

CL-1

CL-2

CL-3

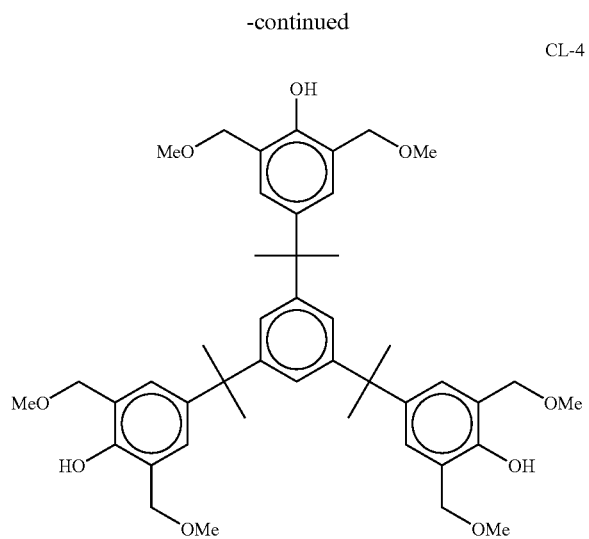

CL-4

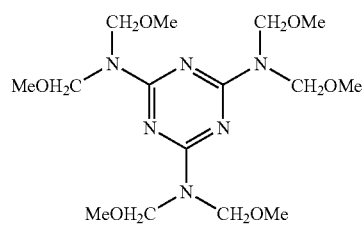

CL-5

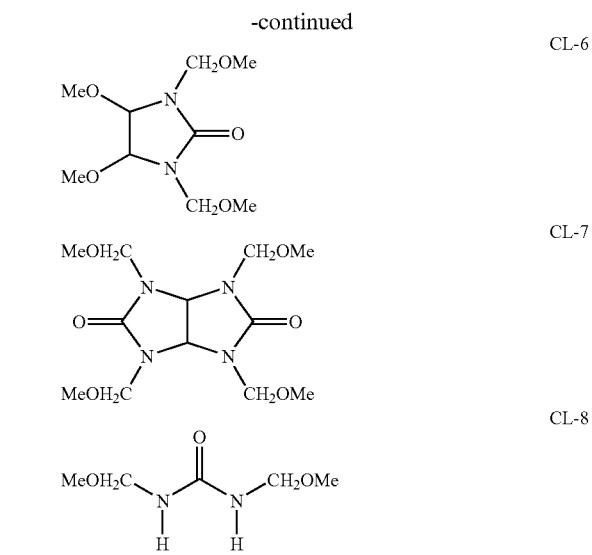

CL-6

CL-7

CL-8

Examples 1 to 36 and Comparative Example 1

<Preparation of Resist>

The components shown in the under-mentioned Tables 2 and 3 were dissolved in solvents to prepare solutions having a solid concentration of 12% by weight, and this was filtered by a polytetrafluoroethylene filter or a polyethylene filter of 0.1 μm to prepare positive type resist solutions. The prepared positive type resist solutions were evaluated by the under-mentioned method, and results were shown in Tables 4 and 5.

TABLE 2

| | Resin (B) (10 g) | Acid generating agent (g) | Basic compound (g) | Surfactant (0.03 g) | Solvent (weight ratio) | Component (C) (g) |
|---|---|---|---|---|---|---|
| Example 1 | (1) | I-1 (0.4) | DBN (0.02) | W-1 | A1 = 100 | — |
| Example 2 | (2) | I-3 (0.3) | TMEA (0.02) | W-1 | A1 = 100 | — |
| Example 3 | (3) | I-5 (0.3) | TPSA (0.02) | W-2 | A1 = 100 | — |
| Example 4 | (4) | I-11 (0.3) | HEP (0.01) | W-2 | A3/B1 = 80/20 | — |
| Example 5 | (5) | I-13 (0.6) | TOA (0.03) | W-3 | A2/B1 = 90/10 | — |
| Example 6 | (6) | I-1 (0.3) Z33 (0.15) | TBAH (0.01) | W-3 | A4/B1 = 90/10 | LCB (1) |
| Example 7 | (7) | I-38 (0.3) Z31 (0.1) | TPA (0.007) | W-4 | A1/B1 = 50/50 | — |
| Example 8 | (8) | I-14 (0.5) | DBN (0.02) | W-4 | A1/B1 = 90/10 | — |
| Example 9 | (9) | I-30 (0.3) Z3 (0.075) | TPI (0.03) | W-1 | A5/B2 = 90/10 | — |
| Example 10 | (10) | I-33 (0.4) Z34 (0.2) | TPI (0.02) | W-1 | A1/B1 = 95/5 | — |
| Example 11 | (11) | I-17 (0.4) Z1 (0.05) Z26 (0.1) | DIA (0.02) | W-2 | A1/B1 = 90/10 | — |
| Example 12 | (12) | I-39 (0.4) | DIA (0.01) HAP (0.01) | W-2 | A1/B1 = 95/5 | — |
| Example 13 | (13) | I-16 (0.3) Z14 (0.1) | TPI (0.03) | W-3 | A1/B1 = 95/5 | — |
| Example 14 | (14) | I-15 (0.3) Z21 (0.3) Z33 (0.075) | DBN (0.02) | W-3 | A1/B1 = 95/5 | — |

TABLE 2-continued

| | Resin (B) (10 g) | Acid generating agent (g) | Basic compound (g) | Surfactant (0.03 g) | Solvent (weight ratio) | Component (C) (g) |
|---|---|---|---|---|---|---|
| Example 15 | (15) | I-18 (0.2) Z7 (0.05) Z2 (0.1) | DIA (0.02) | W-4 | A1/B1 = 80/20 | — |
| Example 16 | (16) | I-25 (0.1) Z33 (0.2) | TPA (0.01) | W-4 | A1 = 100 | — |
| Example 17 | (17) | I-35 (0.3) Z33 (0.1) | TPI (0.03) | W-4 | A1 = 100 | — |
| Example 18 | (18) | I-39 (0.2) Z22 (0.2) | DCMA (0.01) | W-4 | A1 = 100 | — |
| Example 19 | (19) | I-1 (0.7) Z12 (0.1) | TPI (0.02) | W-4 | A1/B1 = 95/5 | — |
| Example 20 | (20) | I-40 (0.2) Z17 (0.2) | TPI (0.03) | W-4 | A1/B1 = 95/5 | — |

TABLE 3

| | Resin (10 g) | Acid generating agent (g) | Basic compound (g) | Surfactant (0.03 g) | Solvent (weight ratio) | Component (C) (g) |
|---|---|---|---|---|---|---|
| Example 21 | (21) | I-1 (0.2) Z32 (0.2) | DBN (0.02) | W-1 | A1/B1 = 95/5 | — |
| Example 22 | (22) | I-41 (0.5) Z8 (0.1) | DIA (0.01) HAP (0.01) | W-1 | A1/B1 = 80/20 | — |
| Example 23 | (23) | I-35 (0.4) Z33 (0.15) | TPSA (0.02) | W-2 | A1/B1 = 90/10 | — |
| Example 24 | (24) | I-38 (0.3) Z5 (0.05) | HEP (0.01) | W-2 | A3/B2 = 80/20 | — |
| Example 25 | (25) | I-26 (0.3) Z29 (0.1) Z35 (0.2) | DIA (0.02) | W-3 | A2/B1 = 90/10 | — |
| Example 26 | (26) | I-37 (0.15) Z13 (0.15) | DIA (0.03) | W-3 | A4/B1 = 90/10 | — |
| Example 27 | (27) | I-35 (0.4) Z33 (0.1) | TPA (0.007) | W-4 | A1/B1 = 50/50 | LCB (1) |
| Example 28 | (2) (5 g) (7) (5 g) | I-42 (0.7) | DIA (0.02) PEA (0.02) | W-4 | A1/B1 = 60/40 | — |
| Example 29 | (1) (3 g) (7) (7 g) | I-57 (0.3) Z35 (0.6) | DIA (0.01) PEA (0.02) | W-4 | A1/B1 = 60/40 | — |
| Example 30 | (6) (5 g) (7) (5 g) | I-42 (0.3) Z30 (0.3) | DIA (0.02) PEA (0.01) | W-4 | A1/B1 = 60/40 | — |
| Example 31 | (7) (5 g) (23) (5 g) | I-51 (0.3) Z40 (0.2) | DIA (0.03) PEA (0.02) | W-4 | A1/B1 = 60/40 | — |
| Example 32 | (6) (7 g) (25) (3 g) | I-53 (0.4) Z33 (0.2) | DIA (0.01) TMEA (0.01) | W-4 | A1/B1 = 60/40 | — |
| Example 33 | (7) (5 g) (15) (5 g) | I-57 (0.3) Z32 (0.3) | DIA (0.01) DCMA (0.005) | W-4 | A1/B1 = 60/40 | — |
| Example 34 | (6) (7 g) (21) (3 g) | I-54 (0.3) Z33 (0.075) | PEA (0.02) | W-4 | A1/B1 = 60/40 | — |
| Example 35 | (7) (6 g) (16) (4 g) | I-39 (0.5) Z5 (0.1) | PEA (0.01) DCMA (0.005) | W-4 | A1/B1 = 60/40 | — |
| Example 36 | (2) (3 g) (13) (7 g) | I-61 (0.5) Z33 (0.075) | DIA (0.01) PEA (0.01) | W-4 | A1/B1 = 60/40 | — |
| Example 37 | (28) | I-42 (0.7) | DIA (0.02) PEA (0.02) | W-4 | A1/B1 = 60/40 | — |
| Example 38 | (29) | I-57 (0.3) Z35 (0.6) | DIA (0.01) PEA (0.02) | W-4 | A1/B1 = 60/40 | — |
| Example 39 | (30) | I-42 (0.3) Z30 (0.3) | DIA (0.02) PEA (0.01) | W-4 | A1/B1 = 60/40 | — |
| Example 40 | (31) | I-51 (0.3) Z40 (0.2) | DIA (0.03) PEA (0.02) | W-4 | A1/B1 = 60/40 | — |
| Comparative Example 1 | (1) | Z31 (0.4) | DBN (0.02) | W-1 | A1 = 100 | — |

Codes as for acid generating agent in the respective Tables correspond to the compounds exemplified as a compound represented by the general formula (I), and the compounds exemplified as an acid generating agent which may be used in combination.

Abbreviation codes in the respective Tables are as follow.
DBN; 1,5-diazabicyclo[4,3,0]nona-5-en
TPI; 2,4,5-triphenylimidazole
TPSA; triphenylsulfonium acetate
HEP; N-hydroxyethylpiperidine
DIA; 2,6-diisopropylaniline
DCMA; dicyclohexylmethylamine
TPA; tripentylamine
TOA; tri-n-otylamine
HAP; hydroxyantipirine
TBAH; tetrabutylammonium hydroxide
TMEA; tris(methoxyethoxyethyl)amine
PEA; N-phenyldiethanolamine
W-1; MEGAFAC F176 (manufactured by Dainippon Ink and Chemicals, Incorporated) (fluorine-base)
W-2; MEGAFAC $R_{08}$ (manufactured by Dainippon Ink and Chemicals, Incorporated) (fluorine-base and silicon-base)
W-3; POLYSILOXANE POLYMER KP-341 (manufactured by Shin-Etsu Chemical Co., Ltd.) (silicon-base)
W-4; TOROYSOL S-366 (manufactured by Troy Chemical Industries, Inc.)
A1; propyleneglycolmethyl ether acetate
A2; 2-heptanone
A3; ethyl ethoxypropionate
A4; γ-butyrolactone
A5; cyclohexanone
B1; propyleneglycol methyl ether
B2; ethyl lactate
LCB; tert-butyl lithpcholate Further, the ratios when a plural number of resins or solvents were used in the respective Tables are weight ratio.

<Evaluation of Resist>

A reflection protective film DUV-42 manufactured by Brewer Science, Inc. was uniformlycoated at a thickness of 600 angstrom by a spin coater on a silicon substrate on which hexamethylsilazane treatment was carried out and dried at 100° C. for 90 seconds on a hot plate, and drying by heating was carried out at 190° C. for 240 seconds. Then, the respective positive type resist solutions were coated by a spin coater, drying was carried out at 120° C. for 90 seconds, and resist films of 0.30 μm were formed.

The resist films were exposed by an ArF eximer laser stepper (manufactured by Integrated Solutions Inc., NA=0.6) through a mask, and they were heated at 120° C. for 90 seconds on a hot plate immediately after exposure. Further, they were developed at 23° C. for 60 seconds by a 2.38% tetramethylammonium hydroxide aqueous solution, rinsed with pure water for 30 seconds and dried to obtain line patterns.

(1) Sensitivity

It represents exposure amount which reproduces a mask pattern of 1/1 line and space of 0.15 μm.

(2) Profile

The profile of 1/1 line and space of 0.15 μm was observed by a scanning microscope, and it was evaluated that a rectangular profile is ○, a profile having a slightly taper form or a slightly trailing form is Δ, and a profile having a perfectly taper form or a perfectly trailing form is X.

(3) Particle

After the positive type resist prepared was left alone at 4° C. for one week, the particle numbers having a particle diameter of 0.2 μm which exist in the solution were counted by a particle counter manufactured by Rion Co., Ltd.

(4) Pitch dependency

The range of duplicating the respective focus depths permitting 0.18 μm±10% was determined in a pattern of line and space having a line width of 0.18 μm (a dense pattern: line and space=1/1) and an isolated pattern (a sparseness pattern: line and space=1/5).

TABLE 4

|  | Sensitivity (mJ/cm$^2$) | Profile | Particle | Pitch dependency (nm) |
|---|---|---|---|---|
| Example 1 | 12 | ○ | 4 | 6.7 |
| Example 2 | 14 | ○ | 7 | 9.5 |
| Example 3 | 11 | ○ | 9 | 5.8 |
| Example 4 | 13 | ○ | 5 | 6.5 |
| Example 5 | 13 | ○ | 6 | 7.5 |
| Example 6 | 10 | ○ | 3 | 5.3 |
| Example 7 | 14 | ○ | 8 | 8.3 |
| Example 8 | 13 | ○ | 4 | 9.5 |
| Example 9 | 15 | ○ | 2 | 8.4 |
| Example 10 | 13 | ○ | 8 | 6.8 |
| Example 11 | 11 | ○ | 7 | 9.2 |
| Example 12 | 14 | ○ | 10 | 6.9 |
| Example 13 | 13 | ○ | 3 | 5.7 |
| Example 14 | 12 | ○ | 2 | 9.2 |
| Example 15 | 10 | ○ | 6 | 8.3 |
| Example 16 | 14 | ○ | 8 | 9.8 |
| Example 17 | 12 | ○ | 5 | 8.7 |
| Example 18 | 11 | ○ | 3 | 6.8 |
| Example 19 | 14 | ○ | 7 | 6.5 |
| Example 20 | 13 | ○ | 4 | 5.8 |
| Example 21 | 15 | ○ | 7 | 7.8 |
| Example 22 | 14 | ○ | 9 | 5.3 |
| Example 23 | 13 | ○ | 8 | 7.6 |
| Example 24 | 14 | ○ | 6 | 5.3 |
| Fxample 25 | 11 | ○ | 10 | 7.5 |
| Example 26 | 15 | ○ | 7 | 6.5 |
| Example 27 | 13 | ○ | 6 | 8.3 |

TABLE 5

|  | Sensitivity (mJ/cm$^2$) | Profile | Particle | Pitch dependency (nm) |
|---|---|---|---|---|
| Example 28 | 11 | ○ | 5 | 6.7 |
| Example 29 | 14 | ○ | 3 | 8.4 |
| Example 30 | 13 | ○ | 7 | 7.8 |
| Example 31 | 11 | ○ | 2 | 5.7 |
| Example 32 | 15 | ○ | 5 | 9.2 |
| Example 33 | 12 | ○ | 4 | 8.4 |
| Example 34 | 14 | ○ | 8 | 6.3 |
| Example 35 | 12 | ○ | 3 | 7.5 |
| Example 36 | 11 | ○ | 7 | 8.7 |
| Example 37 | 10 | ○ | 2 | 6.3 |
| Example 38 | 13 | ○ | 6 | 8.2 |
| Example 39 | 11 | ○ | 3 | 7.6 |
| Example 40 | 12 | ○ | 8 | 8.0 |
| Comparative Example 1 | 27 | Δ | 68 | 17.2 |

It is clear from Tables 4 and 5 that the positive type resist compositions of Examples 1 to 40 are excellent in the sensitivity, pattern profile, and the pitch dependency, and particles are hardly generated at preservation at the lapse of time.

Examples 41 to 52 and Comparative Example 2

<Preparation of Resist>

The components shown in the under-mentioned Table 6 were dissolved in solvents, and the solutions were filtered by a 0.1 μm poly(tetrafluoroethylene) filter to prepare the positive type resist solutions having a solid concentration of 14% by weight, The positive type resist solutions which were prepared were evaluated by the under-mentioned method, and results were shown in Table 8.

TABLE 6

| | Acid generating agent (g) | Resin (10 g) (weight ratio) | Basic compound (g) | Surfactant (0.03 g) | Solvent (weight ratio) | Dissolution inhibiting compound (g) |
|---|---|---|---|---|---|---|
| Example 41 (65) | I-1 (0.4) | R-2 | DBN (0.02) | W-1 | A1 = 100 | — |
| Example 42 (66) | I-3 (0.3) | R-7 | TPI (0.03) | W-1 | A1 = 100 | — |
| Example 43 (67) | I-5 (0.3) Z4 (0.1) | R-8 | TPSA (0.01) | W-2 | A1 = 100 | — |
| Example 44 (68) | I-11 (0.4) Z1 (0.05) | R-9 | HEP (0.02) | W-2 | A3/B1 = 80/20 | — |
| Example 45 (69) | I-13 (0.6) Z15 (0.2) | R-17 | DIA (0.05) | W-3 | A2/B1 = 90/10 | — |
| Example 46 (70) | I-12 (0.4) Z12 (0.3) | R-23 | DCMA (0.03) | W-4 | A4/B1 = 90/10 | — |
| Example 47 (71) | I-8 (0.3) Z33 (0.1) | R-24 | TPA (0.01) | W-4 | A1/B1 = 50/50 | — |
| Example 48 (72) | I-21 (0.3) Z22 (0.1) | R-2/R-23 = 50/50 | TOA (0.005) | W-4 | A1/B1 = 90/10 | — |
| Example 49 (73) | I-35 (0.3) Z29 (0.2) | R-17/R-2 = 30/70 | TBAH (0.0015) | W-4 | A5/B2 = 90/10 | — |
| Example 50 (74) | I-39 (0.2) Z26 (0.5) | R-2/R-22 = 50/50 | TMEA (0.02) | W-4 | A1/B1 = 95/5 | — |
| Example 51 (75) | I-25 (0.39) | PHS* | HAP (0.01) | W-1 | A1/B1 = 90/10 | C-1 (2) |
| Example 42 (76) | I-22 (0.2) | R-2 | DBN (0.002) | W-2 | A1/B1 = 95/5 | C-2 (1) |
| Comparative Example 2 (4) | Z31 (0.4) | R-2 | DBN (0.02) | W-1 | A1 = 100 | — |

PHS: polyhydroxystyrene (manufactured by Nippon Soda Co., Ltd.)

The molar ratios and weight average molecular weights of the resins (R-2) to (R-24) in Table 6 are shown in the under-mentioned Table 7.

TABLE 7

| Resin | Repeating unit molar ratio (corresponding in order from left) | Weight average molecular weight |
|---|---|---|
| R-2 | 60/40 | 12000 |
| R-7 | 60/30/10 | 18000 |
| R-8 | 60/20/20 | 12000 |
| R-9 | 10/50/40 | 13000 |
| R-17 | 10/70/20 | 15000 |
| R-22 | 70/30 | 12000 |
| R-23 | 10/60/30 | 8000 |
| R-24 | 50/20/30 | 16000 |

The structures of the dissolution inhibiting compounds, (C-1) and (C-2) in Table 6 are as described below.

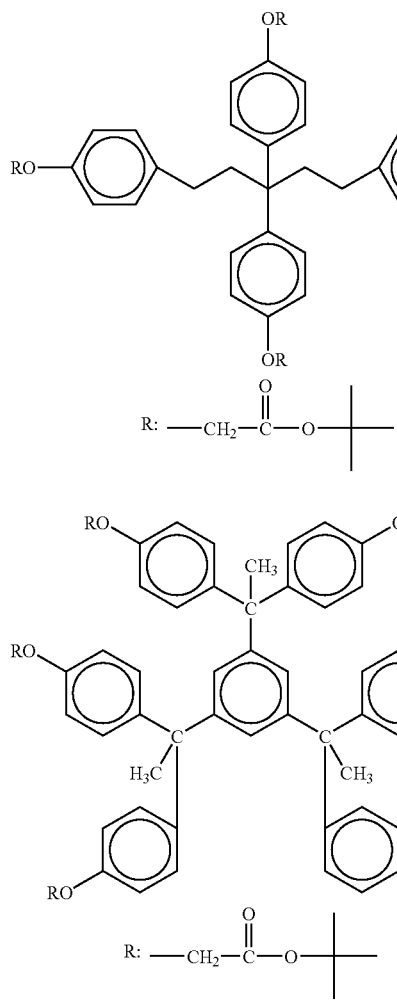

<Evaluation of Resist>

The positive type resist solutions prepared were uniformly coated on a silicon substrate on which hexamethylsilazane treatment was carried out, using a spin coater, drying was carried out by heating at 120° C. for 90 seconds, and resist films of 0.6 μm were formed.

A pattern was exposed to the resist films by using a KrF eximer laser stepper (NA=0.63) using a mask for for 90 seconds, and resist films of 0.6 μm were formed. on a hot plate immediately after exposure. Further, they were developed at 23° C. for 60 seconds by a 2.38% tetramethylammonium hydroxide aqueous solution, rinsed with pure water for 30 seconds and dried to form line patterns. The sensitivity, profile, particle and the pitch dependency were evaluated in like manner as Example 1.

TABLE 8

|  | Sensitivity (mJ/cm$^2$) | Profile | Particle | Pitch dependency (nm) |
|---|---|---|---|---|
| Example 41 | 11 | ○ | 8 | 6.3 |
| Example 42 | 13 | ○ | 4 | 7.8 |
| Example 43 | 12 | ○ | 7 | 5.3 |
| Example 44 | 18 | ○ | 2 | 7.7 |
| Example 45 | 20 | ○ | 9 | 6.7 |
| Example 46 | 16 | ○ | 3 | 7.5 |
| Example 47 | 14 | ○ | 4 | 7.2 |
| Example 48 | 19 | ○ | 6 | 7.8 |
| Example 49 | 15 | ○ | 5 | 6.5 |
| Example 50 | 13 | ○ | 10 | 5.5 |
| Example 51 | 10 | ○ | 9 | 7.2 |
| Example 52 | 17 | ○ | 6 | 6.5 |
| Comparative Example 2 | 33 | x | 84 | 15.6 |

It is clear from Table 8 that the positive type resist compositions of Examples 41 to 52 are excellent in the sensitivity, pattern profile and the pitch dependency, and particles are hardly generated at preservation at the lapse of time.

Examples 53 to 64 and Comparative Example 3

Preparation of Resist>

The compositions shown in the under-mentioned Table 9 were mixed, and the solutions were filtered by a 0.1 μm poly(tetrafluoroethylene) filter to prepare the negative type resist solutions having a solid concentration of 12% by weight.

The negative type resist solutions which were prepared were evaluated by the similar method as Example 37, and results were shown in Table 10.

TABLE 9

|  | Acid generating agent (g) | Resin (10 g) (weight ratio) | Basic compound (g) | Surfactant (0.03 g) | Solvent (weight ratio) | Crosslinking agent (g) |
|---|---|---|---|---|---|---|
| Example 53 (77) | I-1 (0.4) | P-1 | DIA (0.05) | W-1 | A1 = 100 | CL-1 (2) |
| Example 54 (78) | I-3 (0.3) | P-2 | TPI (0.03) | W-1 | A1 = 100 | CL-2 (3) |
| Example 55 (79) | I-5 (0.3) Z4 (0.1) | P-3 | TOA (0.005) | W-2 | A1 = 100 | CL-3 (2.5) |

TABLE 9-continued

| | Acid generating agent (g) | Resin (10 g) (weight ratio) | Basic compound (g) | Surfactant (0.03 g) | Solvent (weight ratio) | Crosslinking agent (g) |
|---|---|---|---|---|---|---|
| Example 56 (80) | I-11 (0.4) Z1 (0.05) | P-4 | HEP (0.02) | W-2 | A3/B1 = 80/20 | CL-4 (3) |
| Example 57 (81) | I-13 (0.6) Z15 (0.2) | P-5 | DBN (0.03) | W-3 | A2/B1 = 90/10 | CL-5 (1.5) |
| Example 58 (82) | I-12 (0.4) Z12 (0.3) | P-6 | DCMA (0.03) | W-4 | A4/B1 = 90/10 | CL-6 (3) |
| Example 59 (83) | I-8 (0.3) Z33 (0.1) | P-1 | TPA (0.01) | W-4 | A1/B1 = 50/50 | CL-7 (2.5) |
| Example 60 (84) | I-21 (0.3) Z22 (0.1) | P-2/P-6 (80/20) | TPSA (0.1) | W-4 | A1/B1 = 90/10 | CL-8 (2.5) |
| Example 61 (85) | I-35 (0.3) Z29 (0.2) | P-3 | TBAH (0.015) | W-4 | A5/B2 = 90/10 | CL-1(2) CL-5(2) |
| Example 62 (86) | I-39 (0.2) Z26 (0.5) | P-4 | TMEA (0.02) | W-4 | A1/B1 = 95/5 | CL-2(1) CL-7(2) |
| Example 63 (87) | I-25 (0.39) | P-5 | HAP (0.01) | W-1 | A1/B1 = 90/10 | CL-1 (2.5) |
| Example 64 (88) | I-22 (0.2) | P-6 | DBN (0.002) | W-2 | A1/B1 = 95/5 | CL-2 (2.5) |
| Comparative Example 3 (5) | Z31 (0.4) | P-1 | DIA (0.05) | W-1 | A1 = 100 | CL-1 (2) |

TABLE 10

| | Sensitivity (mJ/cm²) | Profile | Particle | Pitch dependency (nm) |
|---|---|---|---|---|
| Example 53 | 18 | ○ | 8 | 7.8 |
| Example 54 | 13 | ○ | 3 | 5.8 |
| Example 55 | 10 | ○ | 5 | 6.3 |
| Example 56 | 18 | ○ | 8 | 5.2 |
| Example 57 | 17 | ○ | 7 | 7.2 |
| Example 58 | 19 | ○ | 2 | 6.7 |
| Example 59 | 11 | ○ | 9 | 7.2 |
| Example 60 | 20 | ○ | 6 | 6.8 |
| Example 61 | 16 | ○ | 10 | 5.7 |
| Example 62 | 19 | ○ | 8 | 6.2 |
| Example 63 | 14 | ○ | 4 | 7.6 |
| Example 64 | 18 | ○ | 7 | 7.3 |
| Comparative Example 3 | 28 | Δ | 43 | 19.1 |

It is clear from Table 10 that the negative type resist compositions of Examples 53 to 64 are excellent in the sensitivity, pattern profile and the pitch dependency, and particles are hardly generated at preservation at the lapse of time.

Examples 65 to 76 and Comparative Example 4

<Preparation of Resist>

The components shown in the fore-mentioned Table 6 were dissolved, and the solutions were filtered by a 0.1 μm poly(tetrafluoroethylene) filter to prepare the positive type resist solutions having a solid concentration of 12% by weight.

The positive type resist solutions which were prepared were evaluated by the under-mentioned method, and results were shown in Table 11.

<Evaluation of Resist>

The positive type resist solutions prepared were uniformly coated on a silicon substrate on which hexamethylsilazane treatment was carried out, using a spin coater, drying was carried out by heating at 120° C. for 60 seconds, and resist films of 0.3 μm were formed.

The resist films were irradiated by an electron beam projection lithography equipment manufactured by Nikon Corporation (acceleration voltage=100 keV), and they were heated at 110° C. for 90 seconds on a hot plate immediately after exposure. Further, they were developed at 23° C. for 60 seconds by a 2.38% tetramethylammonium hydroxide aqueous solution, rinsed with pure water for 30 seconds and then dried to form line patterns. The sensitivity, profile and particle were evaluated in like manner as Example 1 except that the sensitivity was set at a 1/1 line and space of 0.10 μm

TABLE 11

| | Sensitivity (μC/cm²) | Profile | Particle |
|---|---|---|---|
| Example 65 | 3.6 | ○ | 4 |
| Example 66 | 4.2 | ○ | 8 |
| Example 67 | 2.2 | ○ | 6 |
| Example 68 | 3.7 | ○ | 2 |
| Example 69 | 4.8 | ○ | 7 |
| Example 70 | 2.7 | ○ | 9 |
| Example 71 | 3.8 | ○ | 3 |
| Example 72 | 4.2 | ○ | 10 |
| Example 73 | 3.2 | ○ | 4 |

TABLE 11-continued

| | Sensitivity (μC/cm²) | Profile | Particle |
|---|---|---|---|
| Example 74 | 4.6 | ○ | 8 |
| Example 75 | 2.4 | ○ | 5 |
| Example 76 | 3.3 | ○ | 3 |
| Comparative Example 4 | 9.2 | Δ (inverted taper) | 84 |

It is clear from Table 11 that the positive type resist compositions of Examples 65 to 76 are excellent in the sensitivity and pattern profile, and particles are hardly generated at preservation at the lapse of time.

Examples 77 to 88 and Comparative Example 5

<Preparation of Resist>
The compositions shown in the fore-mentioned Table 9 were mixed, and the solutions were filtered by a 0.1 μm poly(tetrafluoroethylene) filter to prepare the negative type resist solutions having a solid concentration of 12% by weight.

The negative type resist solutions which were prepared were evaluated by the similar method as Example 65, and results were shown in Table 12.

TABLE 12

| | Sensitivity (μC/cm²) | Profile | Particle |
|---|---|---|---|
| Example 77 | 4.2 | ○ | 8 |
| Example 78 | 3.5 | ○ | 3 |
| Example 79 | 2.3 | ○ | 5 |
| Example 80 | 2.8 | ○ | 10 |
| Example 81 | 3.8 | ○ | 4 |
| Example 82 | 4.5 | ○ | 7 |
| Example 83 | 3.2 | ○ | 2 |
| Example 84 | 4.6 | ○ | 6 |
| Example 85 | 2.6 | ○ | 8 |
| Example 86 | 2.8 | ○ | 5 |
| Example 87 | 3.6 | ○ | 2 |
| Example 88 | 4.9 | ○ | 6 |
| Comparative Example 5 | 7.8 | Δ | 43 |

Examples 89 to 112 and Comparative Example 6

<Preparation of Resist>
The compositions shown in the under-mentioned Table 13 were mixed, and the solutions were filtered by a 0.1 μm poly(tetrafluoroethylene) filter to prepare the positive type resist solutions having a solid concentration of 10% by weight.

TABLE 13

| | Resin (B) (10 g) | Acid generating agent (g) | Basic compound (g) | Surfactant (0.03 g) | Solvent (weight ratio) | Component (C) (g) |
|---|---|---|---|---|---|---|
| Example 89 | (FII-1) | I-1 (0.4) | DBN (0.02) | W-1 | A1 = 100 | — |
| Example 90 | (FII-2) | I-3 (0.3) | TMEA (0.02) | W-1 | A1 = 100 | — |
| Example 91 | (FII-3) | I-5 (0.3) | TPSA (0.02) | W-2 | A1 = 100 | — |
| Example 92 | (FII-4) | I-11 (0.3) | HEP (0.01) | W-2 | A3/B1 = 80/20 | — |
| Example 93 | (FII-5) | I-13 (0.6) | TOA (0.03) | W-3 | A2/B1 = 90/10 | — |
| Example 94 | (FII-6) | I-1 (0.3) Z33 (0.15) | TBAH (0.01) | W-3 | A4/B1 = 90/10 | LCB (1) |
| Example 95 | (FII-7) | I-38 (0.3) Z31 (0.1) | TPA (0.007) | W-4 | A1/B1 = 50/50 | — |
| Example 96 | (FII-8) | I-14 (0.5) | DBN (0.02) | W-4 | A1/B1 = 90/10 | — |
| Example 97 | (FII-9) | I-30 (0.3) Z3 (0.075) | TPI (0.03) | W-1 | A5/B2 = 90/10 | — |
| Example 98 | (FII-10) | I-33 (0.4) Z34 (0.2) | TPI (0.02) | W-1 | A1/B1 = 95/5 | — |
| Example 99 | (FII-11) | I-17 (0.4) Z1 (0.05) Z26 (0.1) | DIA (0.02) | W-2 | A1/B1 = 90/10 | — |
| Example 100 | (FII-12) | I-39 (0.4) | DIA (0.01) HAP (0.01) | W-2 | A1/B1 = 95/5 | — |
| Example 101 | (FII-13) | I-16 (0.3) Z14 (0.1) | TPI (0.03) | W-3 | A1/B1 = 95/5 | — |
| Example 102 | (FII-14) | I-15 (0.3) Z21 (0.3) Z33 (0.075) | DBN (0.02) | W-3 | A1/B1 = 95/5 | — |
| Example 103 | (FII-15) | I-18 (0.2) Z7 (0.05) Z2 (0.1) | DIA (0.02) | W-4 | A1/B1 = 80/20 | — |
| Example 104 | (FII-16) | I-25 (0.1) Z33 (0.2) | TPA (0.01) | W-4 | A1 = 100 | — |
| Example 105 | (FII-17) | I-35 (0.3) Z33 (0.1) | TPI (0.03) | W-4 | A1 = 100 | — |
| Example 106 | (FII-18) | I-39 (0.2) Z22 (0.2) | DCMA (0.01) | W-4 | A1 = 100 | — |

TABLE 13-continued

| | Resin (B) (10 g) | Acid generating agent (g) | Basic compound (g) | Surfactant (0.03 g) | Solvent (weight ratio) | Component (C) (g) |
|---|---|---|---|---|---|---|
| Example 107 | (FII-19) | I-1 (0.7) Z12 (0.1) | TPI (0.02) | W-4 | A1/B1 = 95/5 | — |
| Example 108 | (FII-20) | I-40 (0.2) Z17 (0.2) | TPI (0.03) | W-4 | A1/B1 = 95/5 | — |
| Example 109 | (FII-21) | I-1 (0.2) Z32 (0.2) | DBN (0.02) | W-1 | A1/B1 = 95/5 | — |
| Example 110 | (FII-22) | I-41 (0.5) Z8 (0.1) | DIA (0.01) HAP (0.01) | W-1 | A1/B1 = 80/20 | — |
| Example 111 | (FII-23) | I-35 (0.4) Z33 (0.15) | TPSA (0.02) | W-2 | A1/B1 = 90/10 | — |
| Example 112 | (FII-24) | I-38 (0.3) Z5 (0.05) | HEP (0.01) | W-2 | A3/B2 = 80/20 | — |
| Comparative Example 6 | (FII-1) | I-31 (0.4) Z29 (0.1) Z35 (0.2) | DBN (0.02) | W-1 | A1 = 100 | — |

<Evaluation of Resist>

The respective positive type resist solutions were coated on a silicon substrate on which hexamethylsilazane treatment was carried out, by a spin coater, drying was carried out by heating at 120° C. for 90 seconds on a vacuum adherent type hot plate, and resist films of 0.1 µm were formed.

The resist films obtained were exposed using a laser exposure•dissolution behavior analysis equipment VUVES-4500 (manufactured by Litho Tech Japan Corporation), and they were heated at 120° C. for 90 seconds on a hot plate immediately after exposure. They were developed for 60 seconds by a 2.38% tetramethylammonium hydroxide aqueous solution, and rinsed with pure water to obtain sample wafers. Exposure dose resolving a large pattern was determined. Results were shown in Table 14.

TABLE 14

| | Sensitivity (mJ/cm$^2$) |
|---|---|
| Example 89 | 4 |
| Example 90 | 2 |
| Example 91 | 4 |
| Example 92 | 3 |
| Example 93 | 1 |
| Example 94 | 2 |
| Example 95 | 2 |
| Example 96 | 3 |
| Example 97 | 3 |
| Example 98 | 1 |
| Example 99 | 4 |
| Example 100 | 2 |
| Example 101 | 2 |
| Example 102 | 1 |
| Example 103 | 4 |
| Example 104 | 2 |
| Example 105 | 1 |
| Example 106 | 1 |
| Example 107 | 3 |
| Example 108 | 1 |
| Example 109 | 4 |
| Example 110 | 4 |
| Example 111 | 3 |
| Example 112 | 2 |
| Comparative Example 6 | 8 |

It is clear from Table 14 that the positive type resist compositions of Examples 89 to 112 are excellent in the sensitivity.

Examples 113 to 115

(1) Forming the Lower Resist Layer

FHi-028DD resist (i-ray resist made by Fuji Film Olin Co.) was coated on a 6-inch wafer using Spin Coater Mark 8 made by Tokyo Electron Co., and a uniform film with a thickness of 0.55 µm was obtained by baking at 90° C. for 90 seconds.

The layer was further heated at 200° C. for 3 minutes to obtain a lower resist layer with a thickness of 0.40 µm.

(2) Forming the Upper Resist Layer

The components shown in the under-mentioned Table 17 were dissolved in solvents, and the solutions having a solid concentration of 11% by weight were prepared. The solution obtained was precisely filtered with a membrane filter with a pore diameter of 0.1 µm, and the upper resist composition of the invention was prepared.

The upper resist composition was coated on the lower resist layer, and the upper resist layer with a thickness of 0.20 µm was obtained by heating at 130° C. for 90 seconds.

(3) Evaluation of Resist

The wafer thus obtained was exposed while changing the amount of exposure by attaching a resolution mask to the ArF eximer stepper 9300 manufactured by Integrated Solutions Inc.

After heating at 120° C. for 90 seconds, the wafer was developed with a tetrahydroammonium hydroxide developer (2.38%) for 60 seconds, and a pattern (upper pattern) was obtained by drying after rinsing with distilled water. The wafer having the upper wafer layer was etched (dry etching) using a parallel plate type reactive ion etching apparatus DES-245R made by Plasma System Co, thereby a pattern is formed on the lower layer. The etching gas was oxygen with a pressure of 20 mTorr, and the applied power was 100 mW/cm$^2$. The resist pattern obtained was observed under a scanning electron microscope (SEM) The sensitivity, profile, particle and the pitch dependency were evaluated in like manner as Example 1. Results were shown in Table 18.

TABLE 17

| | Resin (10 g) | Acid generating agent (g) | Basic compound (g) | Surfactant (0.03 g) | Solvent (weight ratio) | Component (C) (g) |
|---|---|---|---|---|---|---|
| Example 113 | (SI-1) | I-42 (0.7) | DIA (0.02) PEA (0.02) | W-4 | A1/B1 = 60/40 | — |
| Example 114 | (SI-2) | I-57 (0.3) Z35 (0.6) | DIA (0.01) PEA (0.02) | W-4 | A1/B1 = 60/40 | — |
| Example 115 | (SI-3) | I-42 (0.3) Z30 (0.3) | DIA (0.02) PEA (0.01) | W-4 | A1/B1 = 60/40 | — |

The structures of the resins (SI-1) to (SI-3) in Table 17 are as described below.

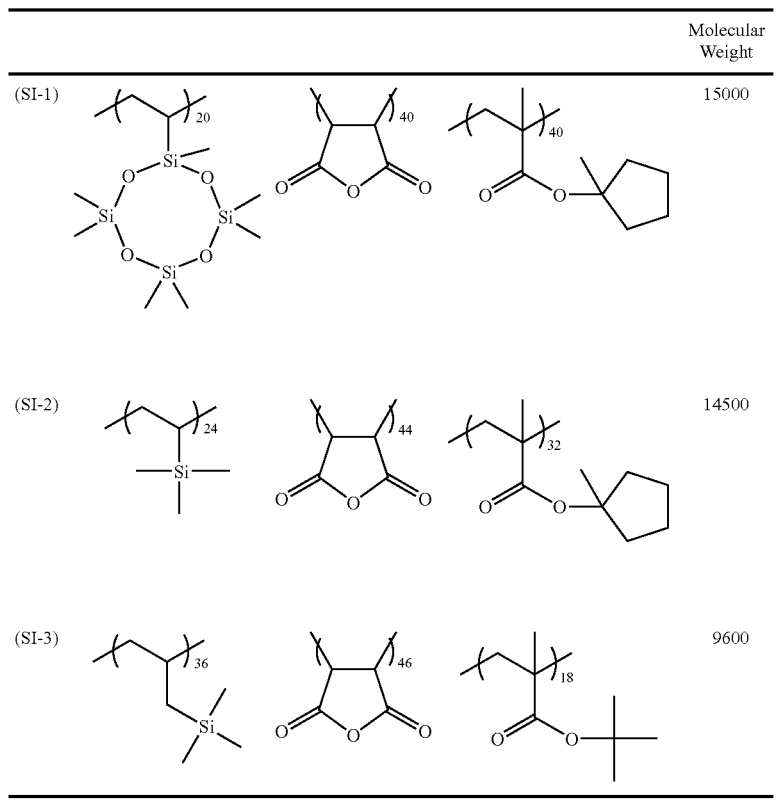

TABLE 18

| | Sensitivity (mJ/cm$^2$) | Profile | Particle | Pitch dependency (nm) |
|---|---|---|---|---|
| Example 113 | 11 | ○ | 5 | 7.3 |
| Example 114 | 12 | ○ | 8 | 8.8 |
| Example 115 | 10 | ○ | 6 | 7.2 |

It is clear from Table 18 that the positive type resist compositions of Examples 113 to 115 are excellent in the sensitivity, pattern profile and the pitch dependency, and particles are hardly generated at preservation at the lapse of time.

Further, ArF eximer laser beam, KrF eximer laser beam, electron beam and F$_2$ eximer laser beam are used as stimulation from the external in the above-mentioned Examples, but it is anticipated that the resist compositions of the present invention exhibits the similar effect for EUV beam.

The stimulation sensitive composition related to the present invention is excellent in the sensitivity, pattern profile and the pitch dependency, and particles are hardly generated at preservation at the lapse of time.

What is claimed is:

1. A positive type photosensitive or heat sensitive composition comprising:
    (A) a compound represented by formula (I) which is capable of generating an acid by irradiation of actinic ray or by heat, and
    (B) a resin increasing the solubility in an alkali developing solution by the action of an acid, wherein the resin has a hydroxystyrene unit:

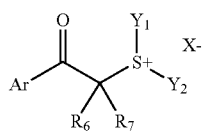

(I)

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a non-nucleophilic anion.

2. A positive type photosensitive or heat sensitive composition comprising:
(A) a compound represented by formula (I) which is capable of generating an acid by irradiation of actinic ray or by heat,
(D) a resin which is soluble in an alkali developing solution, and
(C) a compound having a molecular weight of not more than 3000 which is capable of decomposing by the action of acid to increase solubility in an alkali developing solution:

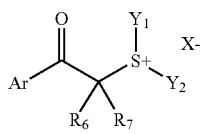

wherein Ar represents an aryl group or an aromatic group containing a hetero atom, $R_6$ represents a cyano group, an alkyl group or an aryl group, $R_7$ represents a monovalent organic group selected from the group consisting of an alkyl group, a cyano group, an alkoxy group, an alkylthio group, an alkoxycarbonyl group and an oxoalkyl group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a non-nucleophilic anion.

3. A negative type photosensitive or heat sensitive composition comprising:
(A) a compound represented by formula (I) which is capable of generating an acid by irradiation of actinic ray or by heat,
(D) a resin which is soluble in an alkali developing solution, and
(E) a crosslinking agent which is capable of crosslinking with the alkali-soluble resin by the action of an acid:

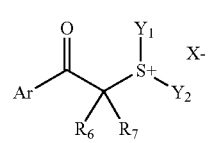

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a non-nucleophilic anion.

4. A positive type photosensitive or heat sensitive composition comprising:
(A) a compound represented by formula (I) which is capable of generating an acid by irradiation of actinic ray or by heat, and
(B) a resin increasing the solubility in an alkali developing solution by the action of an acid, wherein the resin has a fluorine atom:

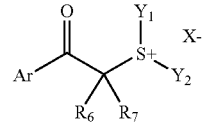

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a non-nucleophilic anion.

5. A positive type photosensitive or heat sensitive composition comprising:
(A) a compound represented by formula (I) which is capable of generating an acid by irradiation of actinic ray or by heat, and (B) a resin increasing the solubility in an alkali developing solution by the action of an acid, wherein the resin has a silicon atom:

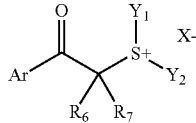

(I)

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a non-nucleophilic anion.

6. A positive type photosensitive or heat sensitive composition comprising:

(A) a compound represented by formula (I) which is capable of generating an acid by irradiation of actinic ray or by heat, and (B) a resin and increasing the solubility in an alkali developing solution by the action of an acid, wherein the resin has a monocyclic or polycyclic alicyclic hydrocarbon structure:

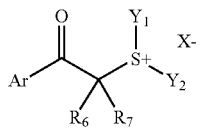

(I)

wherein Ar represents an aryl group or an aromatic group containing a hetero atom, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, Ar and at least one of $Y_1$ and $Y_2$ may be bonded to each other to form a ring, Ar and $R_6$ may be bonded to each other to form a ring, $R_6$ and $R_7$ may be bonded to each other to form a ring, Ar, $R_6$, $R_7$, $Y_1$ or $Y_2$ may be bonded at any one position through a linking group, so that the component (A) may have 2 or more of the structures of formula (I), and $X^-$ represents a carboxylic acid anion, a sulfonyl imide anion, a bis(alkylsulfonyl)imide anion, a tris(alkylsulfonyl)methyl anion, an arylsulfonic acid anion or a camphorsulfonic acid anion.

7. The photosensitive composition according to claim 6, wherein the formula (I) satisfies at least one of the following (a) to (b):

(a) $R_6$ and $R_7$ both represent an alkyl group, and (b) $R_6$ represents a hydrogen atom and $R_7$ represents an alkyl group having 4-20 carbon atoms.

8. A positive type photosensitive or heat sensitive composition comprising:

(A) a compound represented by formula (Ia) which is capable of generating an acid by irradiation of actinic ray or by heat, and (B) a resin increasing the solubility in an alkali developing solution by the action of an acid, wherein the resin has a monocyclic or polycyclic alicyclic hydrocarbon structure:

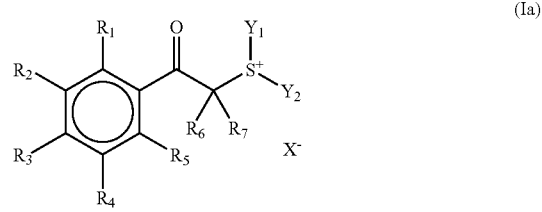

(Ia)

wherein $R_1$ to $R_5$ may be the same or different, and each represents a hydrogen atom, a nitro group, a halogen atom, an alkyl group, an alkoxy group, an alkoxycarbonyl group, an aryl group or an acylamino group, $R_6$ represents a hydrogen atom, a cyano group, an alkyl group or an aryl group, $R_7$ represents a monovalent organic group, $Y_1$ and $Y_2$ may be the same or different, and represents an alkyl group, an aryl group, an aralkyl group or an aromatic group containing a hetero atom, $Y_1$ and $Y_2$ may be bonded to each other to form a ring, at least 2 of $R_1$ to $R_5$ may be bonded to each other to form a ring, at least one of $R_1$ to $R_5$ is a linear, branched or cyclic alkyl group, at least one of $R_1$ to $R_5$ and at least one of $Y_1$ and $Y_2$ may be bonded to each other to form a ring, at least one of $R_1$ to $R_5$ and $R_6$ may be bonded to each other to form a ring, $R_6$ and $R_7$ may be bonded to each other to form a ring, $R_1$, $R_2$, $R_3$, $R_4$, $R_5$, $R_6$, $R_7$, $Y_1$ or $Y_2$ may be bonded at any one position through a linking group, so that the component (A) may have 2 or more of the structures of formula (Ia), and $X^-$ represents a non-nucleophilic anion.

9. The positive type photosensitive or heat sensitive composition according to any one of claims 1 and 4-8, further comprising (C) a compound having a molecular weight of not more than 3000 which is capable of decomposing by the action of acid to increase solubility in an alkali developing solution.

10. The composition according to claim 9, further comprising (F) a basic compound and/or (G) a surfactant containing at least one of a group consisting of a fluorine atom and a silicon atom.

11. The composition according to claim 10, wherein the compound (F) is a compound having a structure selected from the group consisting of an imidazole structure, a diazabicyclo structure, an oniumhydroxy structure, an oniumcarboxylate structure, a trialkylamine structure, an aniline structure and a pyridine structure, or an alkylamine derivative having a hydroxy group and/or an ether bond, or an aniline derivative having a hydroxy group and/or an ether bond.

12. The composition according to any one of claims 1, 3 and 4-8, further comprising (F) a basic compound and/or (G) a surfactant containing at least one of a group consisting of a fluorine atom and a silicon atom.

13. The composition according to claim 12, wherein the compound (F) is a compound having a structure selected from the group consisting of an imidazole structure, a diazabicyclo structure, an oniumhydroxy structure, an oniumcarboxylate structure, a trialkylamine structure, an aniline structure and a pyridine structure, or an alkylamine derivative having a hydroxy group and/or an ether bond, or an aniline derivative having a hydroxy group and/or an ether bond.

14. The photosensitive or heat sensitive composition according to any one of claims 1, 3, 4-5 and 8, wherein the formula (I) or (Ia) satisfies at least one of the following (a) to (c):
    (a) $R_6$ and $R_7$ both represent an alkyl group,
    (b) $R_6$ represents a hydrogen atom and $R_7$ represents an alkyl group having 4-20 carbon atoms, and
    (c) $X^-$ represents a non-nucleophilic anion selected from the group consisting of a sulfonic acid anion, a carboxylic acid anion, a sulfonyl imide anion, a bis(alkylsulfonyl)imide anion, and a tris(alkylsulfonyl)methyl anion.

15. The positive type photosensitive or heat sensitive composition according to claim 6 or 8, wherein the resin (B) has further a repeating unit having a lactone structure.

16. The composition according to claim 15, further comprising (F) a basic compound and/or (G) a surfactant containing at least one of a group consisting of a fluorine atom and a silicon atom.

17. The composition according to claim 16, wherein the compound (F) is a compound having a structure selected from the group consisting of an imidazole structure, a diazabicyclo structure, an oniumhydroxy structure, an oniumcarboxylate structure, a trialkylamine structure, an aniline structure and a pyridine structure, or an alkylamine derivative having a hydroxy group and/or an ether bond, or an aniline derivative having a hydroxy group and/or an ether bond.

18. A compound represented by formula (I):

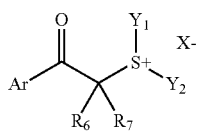

(I)

wherein Ar represents an aryl group or an aromatic group containing a hetero atom,
$R_6$ represents a hydrogen atom, a cyano group, an alkyl group or an aryl group,
$R_7$ represents a monovalent organic group,
$Y_1$ and $Y_2$ may be the same or different, and each represents an alkyl group, an aryl group, an aralkyl group or an aromatic group containing a hetero atom, provided that $Y_1$ and $Y_2$ may be bonded to each other to form a ring,
Ar and at least one of $Y_1$ and $Y_2$ may be bonded to each other to form a ring,
Ar and $R_6$ may be bonded to each other to form a ring,
$R_6$ and $R_7$ may be bonded to each other to form a ring,
Ar, $R_6$, $R_7$, $Y_1$ or $Y_2$ may be bonded at any one position through a linking group, so that the compound may have 2 or more of the structures of formula (I), and $X^-$ represents a carboxylic acid anion, a sulfonyl imide anion, a bis(alkylsulfonyl)imide anion, a tris(alkylsulfonyl)methyl anion, an arylsulfonic acid anion substituted by a fluorine atom or a group containing a fluorine atom or a camphorsulfonic acid anion.

19. A compound represented by formula (Ia):

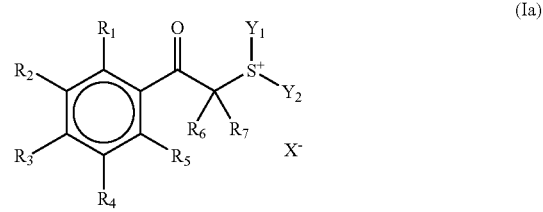

(Ia)

wherein $R_1$ to $R_5$ may be the same or different, and each represents a hydrogen atom, a nitro group, a halogen atom, an alkyl group, an alkoxy group, an alkoxycarbonyl group, an aryl group or an acylamino group,
$R_6$ represents a hydrogen atom, a cyano group, an alkyl group or an aryl group,
$R_7$ represents a monovalent organic group,
$Y_1$ and $Y_2$ may be the same or different, and each represents an alkyl group, an aryl group, an aralkyl group or an aromatic group containing a hetero atom, provided that $Y_1$ and $Y_2$ may be bonded to each other to form a ring,
at least 2 of $R_1$ to $R_5$ may be bonded to each other to form a ring,
at least one of $R_1$ to $R_5$ is a linear, branched or cyclic alkyl group,
at least one of $R_1$ to $R_5$ and at least one of $Y_1$ and $Y_2$ may be bonded to each other to form a ring,
at least one of $R_1$ to $R_5$ and $R_6$ may be bonded to each other to form a ring,
$R_1$, $R_2$, $R_3$, $R_4$, $R_5$, $R_6$, $R_7$, $Y_1$ or $Y_2$ may be bonded at any one position through a linking group, so that the component (A) may have 2 or more of the structures of formula (Ia), and
$X^-$ represents a non-nucleophilic anion.

20. The compound according to claim 19, wherein both $R_6$ and $R_7$ represent an alkyl group.

21. A compound represented by formula (I):

(I)

wherein Ar represents an aryl group or an aromatic group containing a hetero atom,
$R_6$ represents a hydrogen atom,
$R_7$ represents an alkyl group,
$Y_1$ and $Y_2$ may be the same or different, and each represents an alkyl group, an aryl group, an aralkyl group or an aromatic group containing a hetero atom provided that $Y_1$ and $Y_2$ are bonded to each other to form a ring,
Ar and at least one of $Y_1$ and $Y_2$ may be bonded to each other to form a ring,
Ar, $R_7$, $Y_1$ or $Y_2$ may be bonded at any one position through a linking group, so that the compound may have 2 or more of the structures of formula (I), and $X^-$ represents a non-nucleophilic anion selected from the group consisting of a sulfonic acid anion substituted with a fluorine atom at the α position of the sulfonic acid, an arylsulfonic acid anion substituted with a fluorine atom or a group having a fluorine atom, a bis(alkylsulfonyl)imide anion in which the alkyl group is substituted with a fluorine atom, and a tris(alkylsulfonyl)methyl anion in which the alkyl group is substituted with a fluorine atom.

* * * * *